United States Patent
Ueda et al.

(10) Patent No.: US 12,292,363 B2
(45) Date of Patent: May 6, 2025

(54) METHOD FOR PREPARING BIOLOGICAL MATERIAL HAVING EXCELLENT LIGHT-TRANSMITTING PROPERTY

(71) Applicant: RIKEN, Saitama (JP)

(72) Inventors: Hiroki Ueda, Saitama (JP); Kazuki Tainaka, Saitama (JP); Tatsuya Murakami, Tokyo (JP)

(73) Assignee: RIKEN, Saitama (JP)

( * ) Notice: Subject to any disclaimer, the term of this patent is extended or adjusted under 35 U.S.C. 154(b) by 143 days.

(21) Appl. No.: 17/868,721

(22) Filed: Jul. 19, 2022

(65) Prior Publication Data

US 2022/0381657 A1    Dec. 1, 2022

Related U.S. Application Data

(63) Continuation of application No. 16/096,130, filed as application No. PCT/JP2017/016410 on Apr. 25, 2017, now Pat. No. 11,656,159.

(30) Foreign Application Priority Data

Apr. 28, 2016 (JP) .................. 2016-092025

(51) Int. Cl.
*G01N 1/00* (2006.01)
*G01N 1/28* (2006.01)
(Continued)

(52) U.S. Cl.
CPC .............. *G01N 1/30* (2013.01); *G01N 1/28* (2013.01); *G01N 33/48* (2013.01); *G01N 33/4833* (2013.01)

(58) Field of Classification Search
CPC ....................................................... G01N 1/30
(Continued)

(56) References Cited

U.S. PATENT DOCUMENTS

2013/0045503 A1    2/2013  Miyawaki
2014/0087419 A1    3/2014  Riken
(Continued)

FOREIGN PATENT DOCUMENTS

EP          2926658 A1      10/2015
JP          2003-066035      3/2003
(Continued)

OTHER PUBLICATIONS

A. K. L. Liu et al. "Bringing CLARITY to the human brain: visualization of Lewy pathology in three dimensions" Neuropathology and Applied Neurobiology (2016), 42, 573-587—First Published 2015 (Year: 2015).*

(Continued)

*Primary Examiner* — Paul S Hyun
*Assistant Examiner* — Emily R. Berkeley
(74) *Attorney, Agent, or Firm* — Kristina Castellano; CASTELLANO PLLC

(57) ABSTRACT

The present invention relates to a clearing technique which uses a solution containing at least one of a compound having a delipidation ability, a compound having a biochrome decoloring ability, a compound having a decalcification ability, a compound having a refractive index adjusting ability, and a compound having a tissue swelling ability. The clearing technique is suitable for use in high-throughput and low-magnification imaging which involves a simple process.

11 Claims, 41 Drawing Sheets

(51) Int. Cl.
*G01N 1/30* (2006.01)
*G01N 33/48* (2006.01)
*G01N 33/483* (2006.01)

(58) Field of Classification Search
USPC .......................................................... 436/17
See application file for complete search history.

(56) References Cited

U.S. PATENT DOCUMENTS

| | | | |
|---|---|---|---|
| 2014/0178927 | A1 | 6/2014 | Riken |
| 2015/0285718 | A1 | 10/2015 | Hatta et al. |
| 2016/0011086 | A1 | 1/2016 | Onodera |
| 2016/0266016 | A1 | 9/2016 | Riken |
| 2018/0180520 | A1 | 6/2018 | Riken |

FOREIGN PATENT DOCUMENTS

| | | | |
|---|---|---|---|
| JP | 2015-049101 | | 3/2015 |
| JP | 2017108684 | | 6/2017 |
| WO | 2012147965 | | 11/2012 |
| WO | 2012161143 | | 11/2012 |
| WO | 2013191274 | | 12/2013 |
| WO | 2014069519 | | 5/2014 |
| WO | 2014115206 | | 7/2014 |
| WO | 2015022883 | | 2/2015 |
| WO | 2015041755 | A1 | 3/2015 |
| WO | 2016004563 | A1 | 1/2016 |

OTHER PUBLICATIONS

Office Action in U.S. Appl. No. 16/096,130 dated Sep. 23, 2021.
Office Action in U.S. Appl. No. 16/096,130 dated Jan. 11, 2022.
ISR in PCT/JP2017/016410 dated Aug. 1, 2017.
International Preliminary Report on Patentability (in English, containing Written Opinion) in PCT/JP2017/016410, dated Oct. 30, 2018.
EP Office Action for EP application No. 17789546.3, dated Feb. 14, 2022.
Susaki Etsuo A et al: "Whole-body and Whole-Organ Clearing and Imaging Techniques with Single Cell Resolution: Toward Organism-Level Systems Biology in Mammals", Cell Chem Bio vol. 23, No. 1, Jan. 21, 2016.
Treweek et al. "Whole-body tissue stabilization and selective extractions via tissue-hydrogel hybrids for high-resolution intact circuit mapping and phenotyping" Nature Protocols vol. 10, pp. 1860-1896 (2015).
Susaki et al. "Whole-Brain Imaging with Single-Cell Resolution Using Chemical Cocktails and Computational Analysis" Cell 157, 726-739, Apr. 24, 2014—"Extended Experimental Procedures" accessed from http://dx.doi.org/10.1016/j.cell.2014.03.042 on Sep. 21, 2021 (year: 2014).
Hans-Ulrich Dodt et al. "Ultramicroscopy: three-dimensional visualization of neuronal networks in the whole mouse brain", Nature Methods, vol. 4, No. 4, pp. 331-336 (2007).
Klaus Becker et al.: "Chemical Clearing and Dehydration of GFP Expressing Mouse Brains," PLoS ONE, vol. 7, Issue 3, e33916 (May 1, 2012).
Meng-Tsen Ke et al: "SeeDB: a simple and morphology-preserving optical clearing agent for neuronal circuit reconstruction", Nature Neuroscience, vol. 16, No. 8, pp. 1154-1161 (Jun. 23, 2013).
Hiroshi Hama et al: "Scale: a chemical approach for fluorescence imaging and reconstruction of transparent mouse brain", Nature Neuroscience, vol. 14, No. 11, pp. 1481-1490 (Aug. 30, 2011).
Kwanghun Chung et al.: "Structural and Molecular Interrogation of Intact Biological Systems", Nature, vol. 497, pp. 332-339 (May 16, 2013).
Bin Yang et al.: "Single-Cell Phenotypying within Transparent Intact Tissue through Whole-Body Clearing" Cell, vol. 158, pp. 945-958 (Aug. 14, 2014).
Evan Murray et al.: "Simple, Scalable Proteomic Imaging for High Dimensional Profiling of Intact Systems," Cell vol. 163, pp. 1500-1514 (Dec. 3, 2015).
Kazuki Tainaka et al.: "Whole-Body Imaging with Single-Cell Resolution by Tissue Decolorization", Cell, vol. 159, pp. 911-924 (Nov. 6, 2014).
Etsuo a Susaki et al. "Advanced CUBIC protocols for whole-brain and whole-body clearing and imaging", Nature Protocols, vol. 10, No. 11, pp. 1709-1727 (2015).
Etsuo A. Susaki et al. "Whole-Brain Imaging with Single Cell Resolution Using Chemical Cocktails and Computational Analysis", Cell, vol. 157, pp. 1-14 (Apr. 24, 2014).
Etsuo A. Susaki et al. "Whole-Brain Imaging with Single Cell Resolution Using Chemical Cocktails and Computational Analysis", Cell, vol. 157, No. 3, pp. 726-739 (Apr. 1, 2014).
Pan et al. "Shrinkage-mediated imaging of entire organs and organisms using uDISCO", Nature Methods, vol. 13, No. 10, pp. 859-867 (Oct. 1, 2016).
EESR for 17789546.3, dated Dec. 9, 2019.
Office Action in JP application 2023-076864, dated Oct. 29, 2024.

\* cited by examiner

FIG. 3

PL: PHOSPHOLIPID CONTENT (%)
CL: CHOLESTEROL CONTENT (%)

FIG. 9
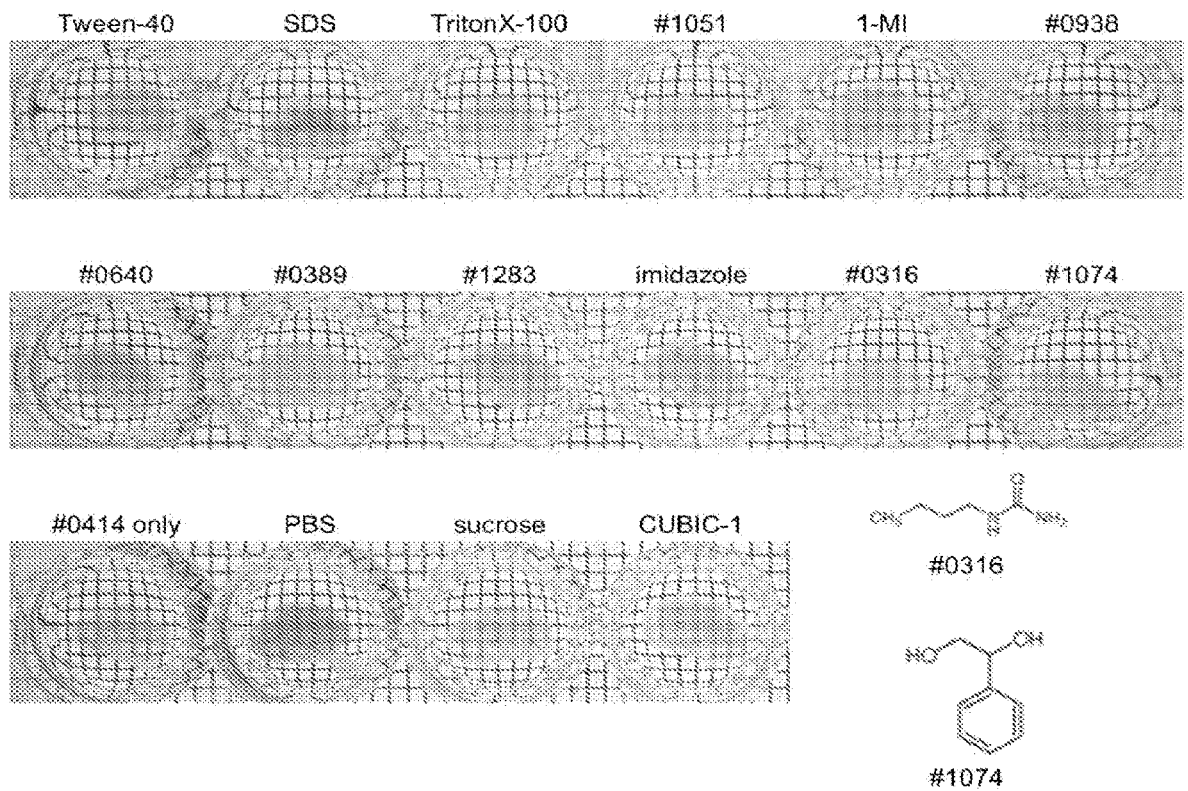
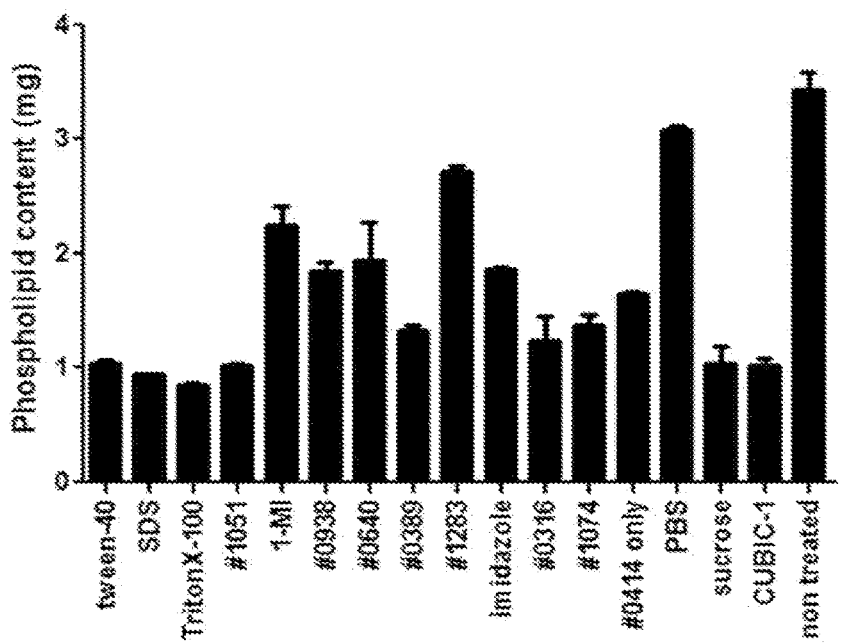
Kidney phospholipid content

FIG. 11
Optimization of delipidation (brain)
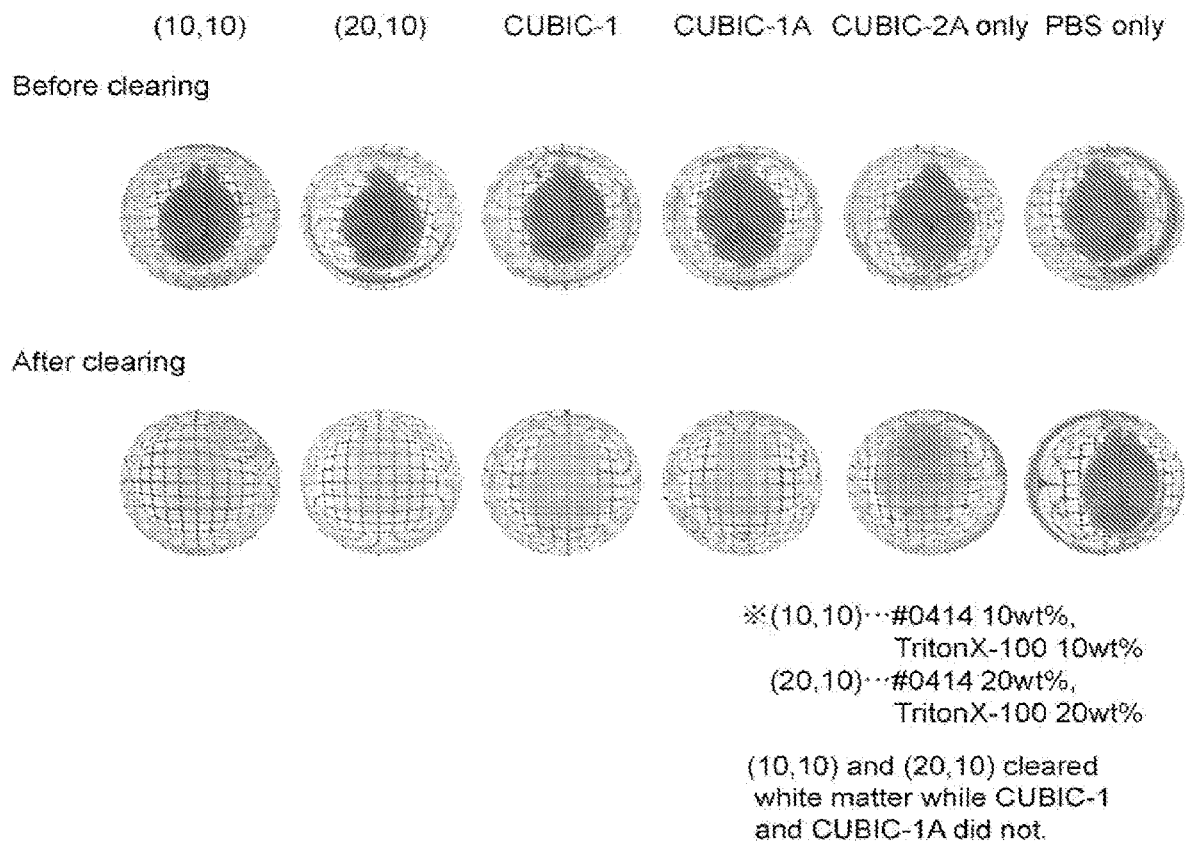
※(10,10)···#0414 10wt%,
TritonX-100 10wt%
(20,10)···#0414 20wt%,
TritonX-100 20wt%
(10,10) and (20,10) cleared
white matter while CUBIC-1
and CUBIC-1A did not.
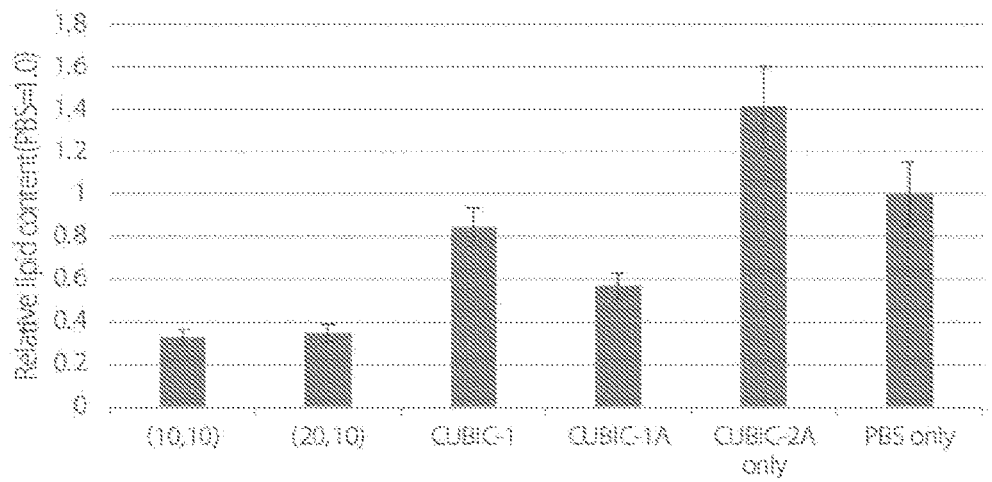

FIG. 12
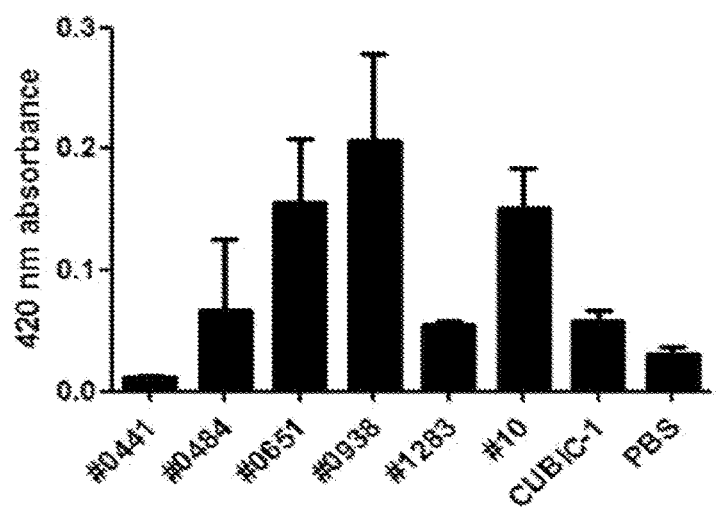
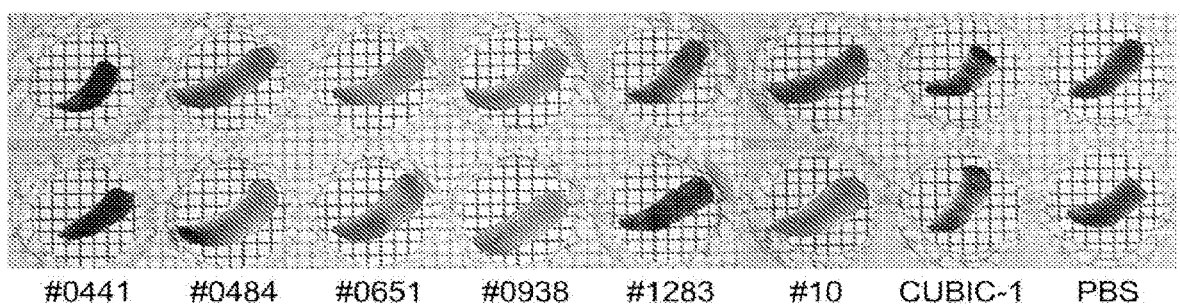

FIG.13
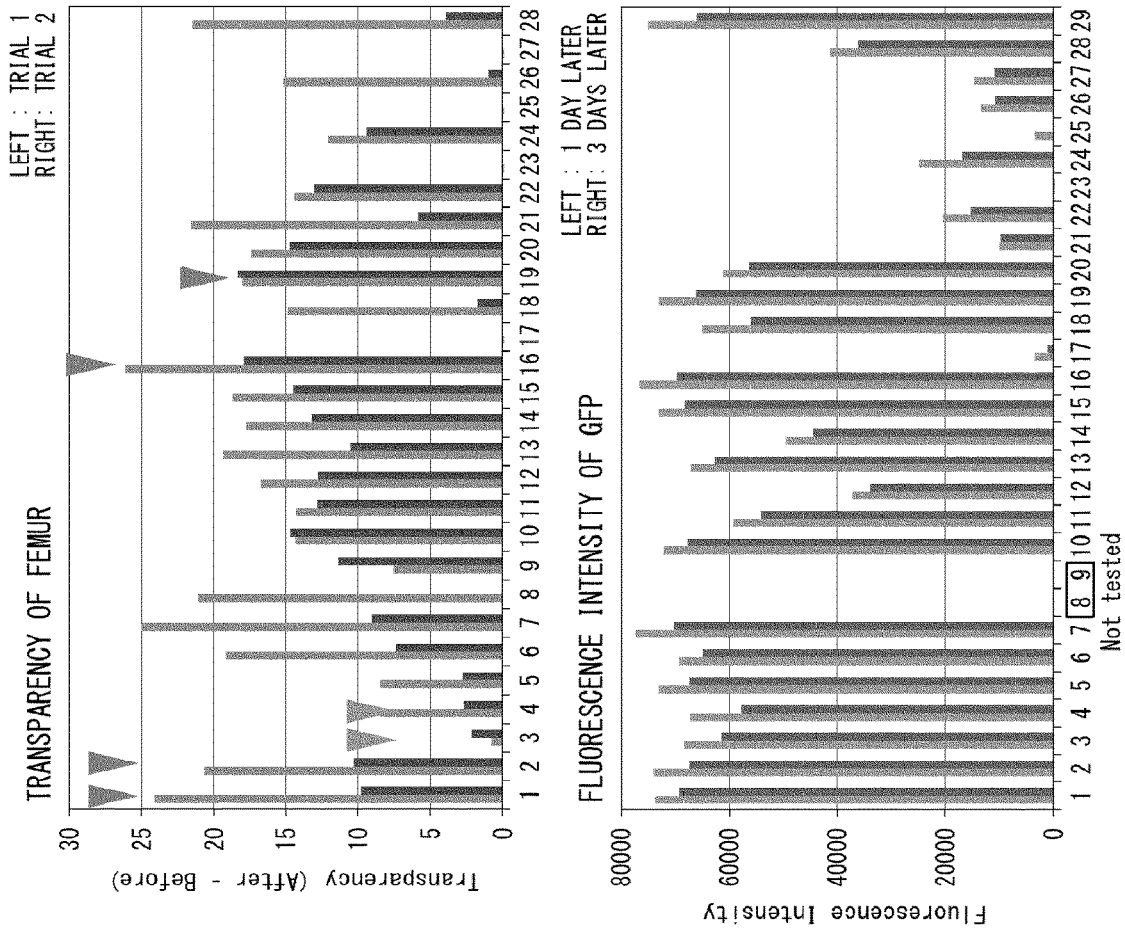
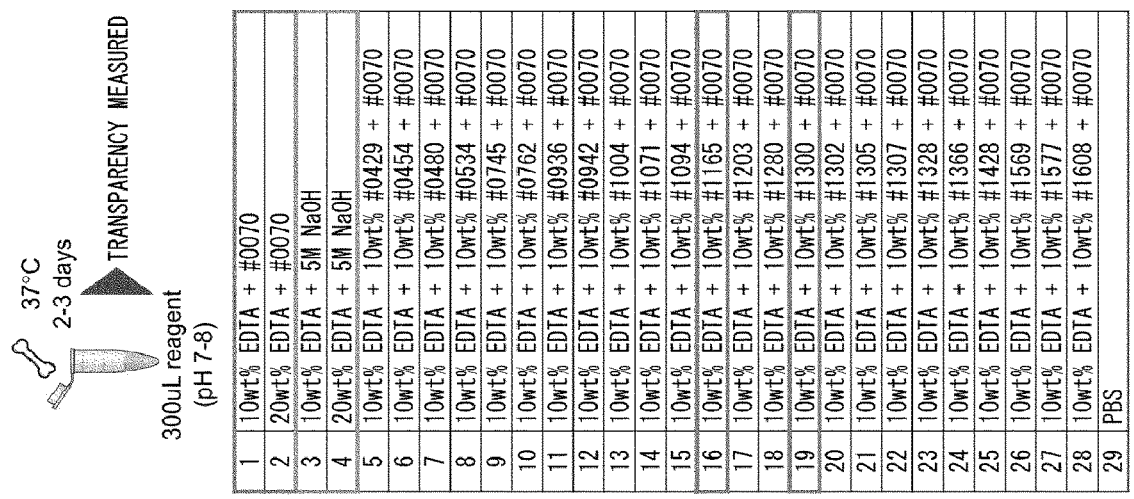

FIG.14
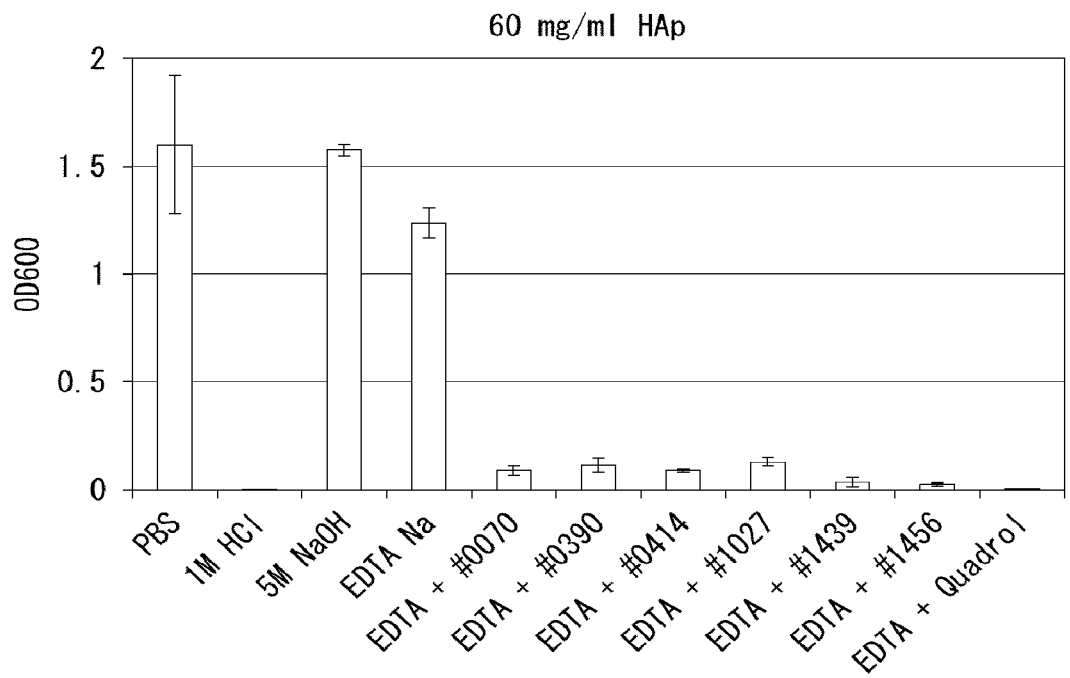
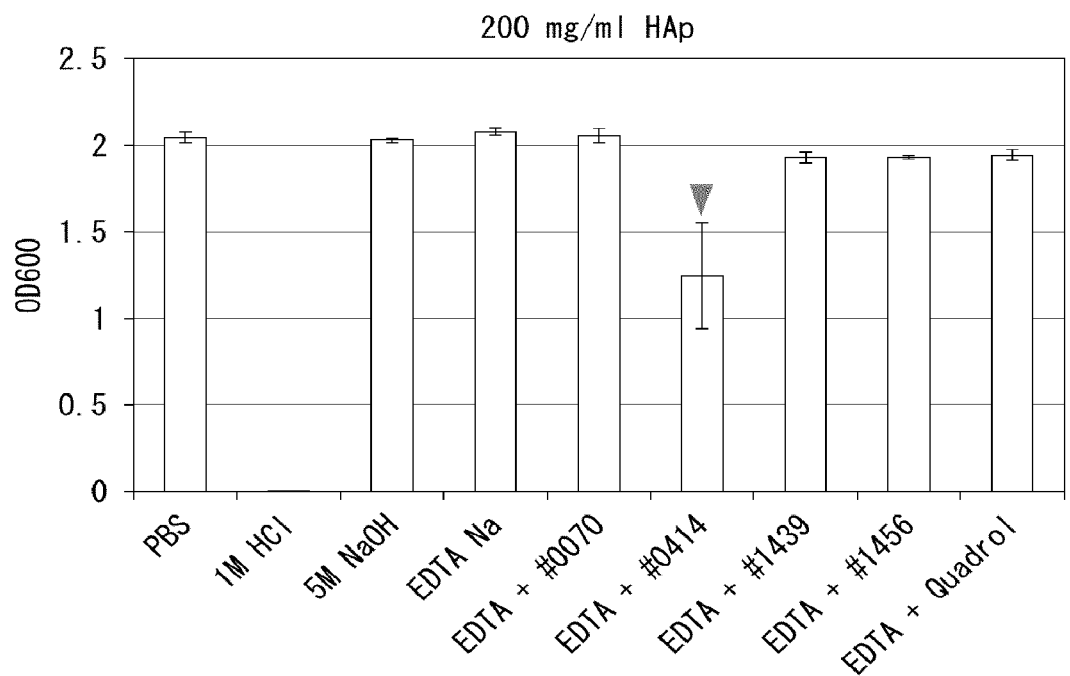

FIG.15
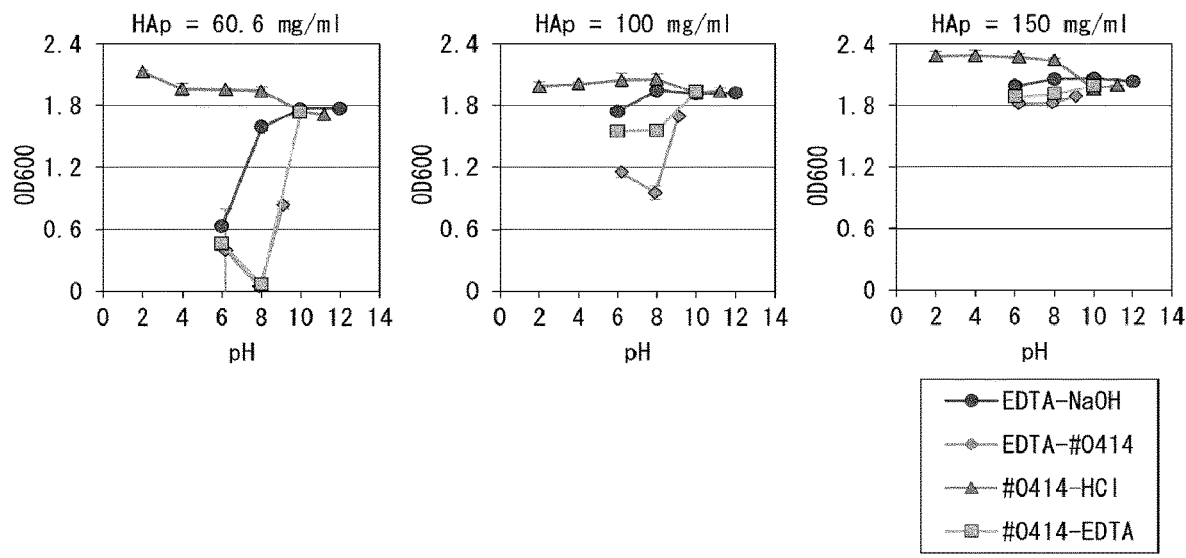
FIG.16
TEMPERATURE DEPENDENCY
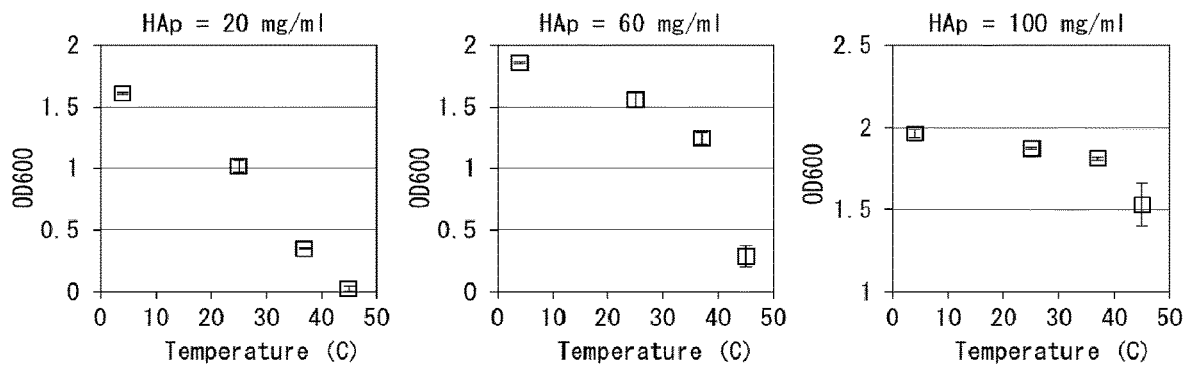
EDTA CONCENTRATION DEPENDENCY
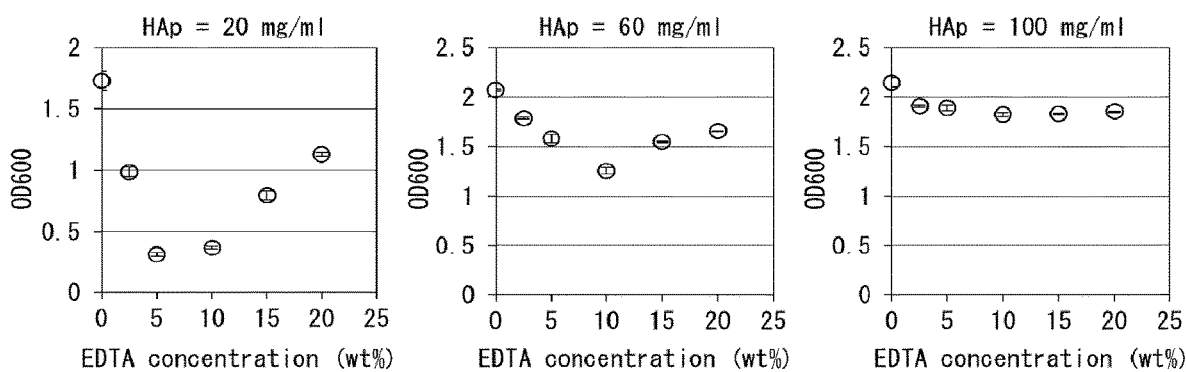

FIG. 18
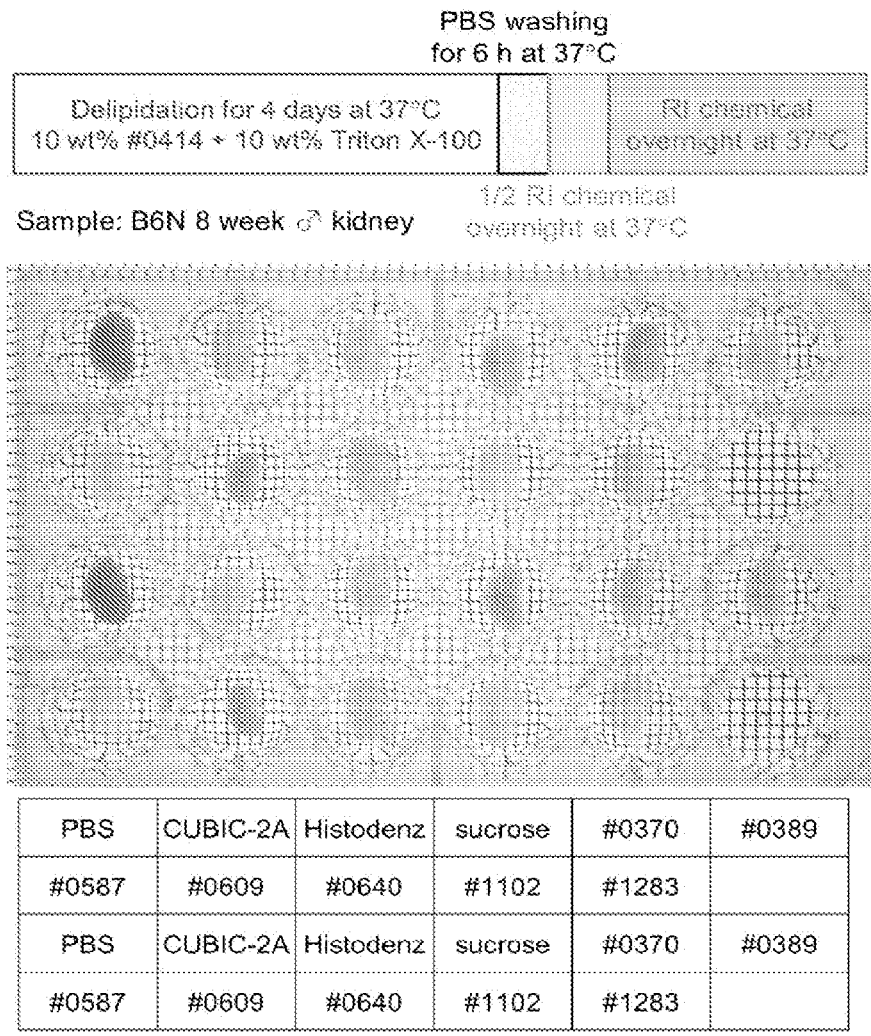
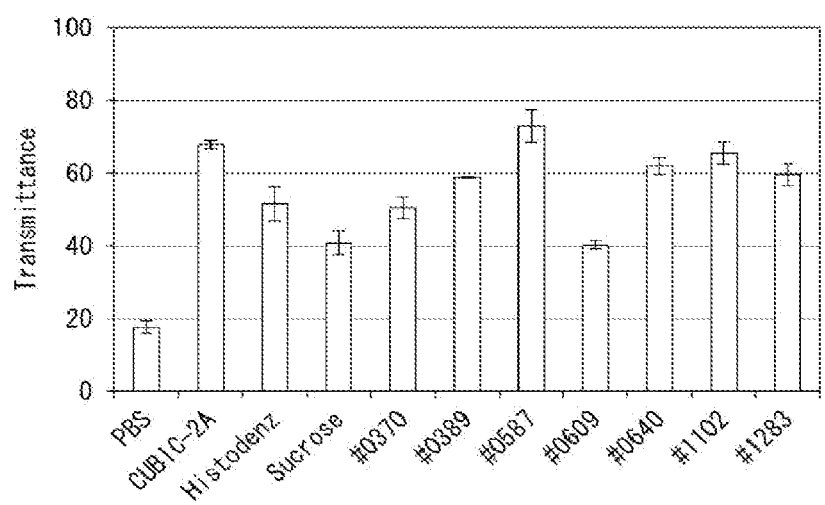

FIG.19

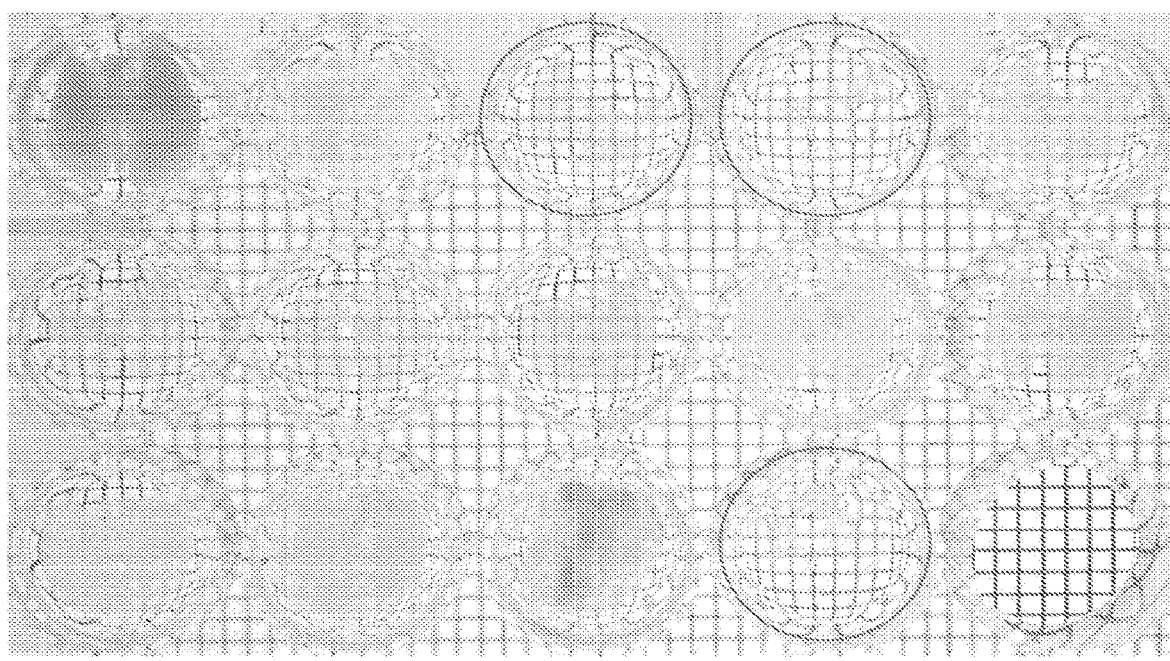

| PBS | CUBIC-2A (pH 10.3, RI = 1.45) | 46 wt% #0640 + 30 wt% #1283 (pH 6.9, RI = 1.52) | 46 wt% #0640 + 30 wt% Nicotinamide (pH 6.5, RI = 1.53) | 46 wt% #0640 + 30 wt% 3-Picolylamine (pH 12.1, RI = 1.52) |
|---|---|---|---|---|
| 46 wt% #0640 + 30 wt% N,N-Diethylnicotinamide (pH 7.2, RI = 1.51) | 46 wt% #0640 + 30 wt% Isonicotinamide (pH 7.2, RI = 1.52) | 46 wt% #0640 + 30 wt% N,N-Diethylisonicotinamide (pH 6.6, RI = 1.51) | 46 wt% #0640 + 30 wt% Histodenz (pH 7.3, RI = 1.53) | 46 wt% sucrose + 30 wt% #1283 (pH 6.8, RI = 1.50) |
| 46 wt% 3-Picolylamine + 30 wt% #1283 (pH 11.9, RI = 1.51) | 46 wt% N,N-Diethylnicotinamide + 30 wt% #1283 (pH 6.5, RI = 1.49) | 46 wt% Nicotinamide + 30 wt% #1283 (pH 6.4, RI = 1.51) | 46 wt% Histodenz + 30 wt% #1283 (pH 6.7, RI = 1.52) | |

FIG.20
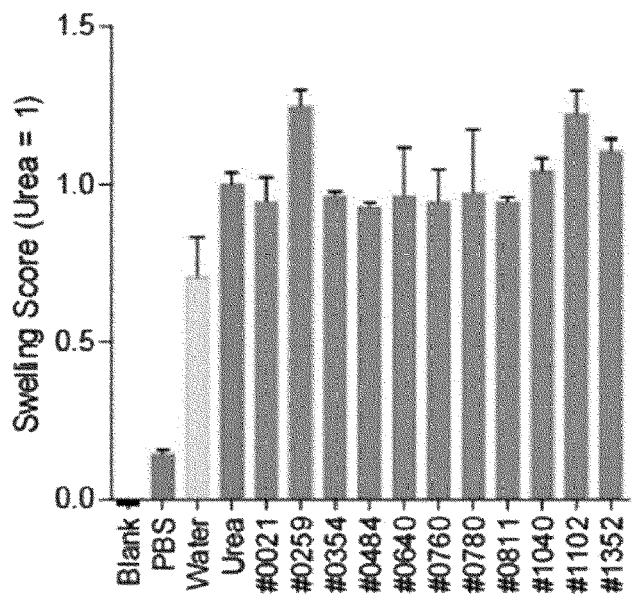
0021
β-Alanine
0259
2-Aminoethanol
0354
Adipic Dihydrazide
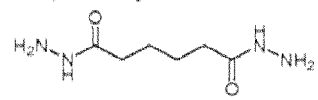
0484
1-(3-Aminopropyl)
imidazole
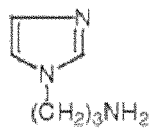
0640
2,3-Dimethyl-1-phenyl-
5-pyrazolone
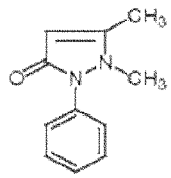
0760
Methyl Carbazate
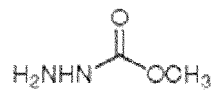
0780
Diethylenetriamine
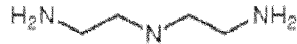
0811
1,3-Dimethylurea
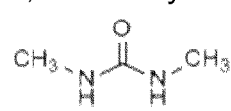
1040
2-Imidazolidinone
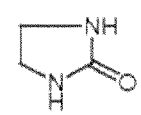
1102
3-Picolylamine
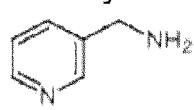
1352
Imidazole
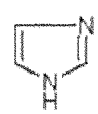

FIG.21
BRAIN TREATED WITH CUBIC-1
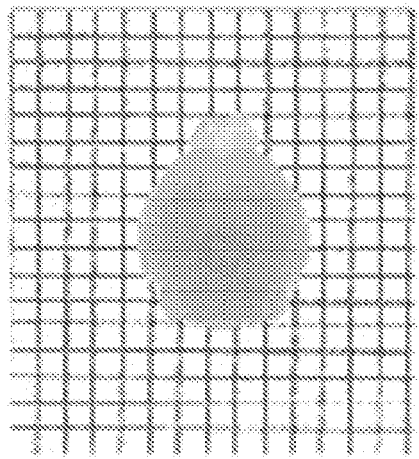
BRAIN TREATED WITH #1352
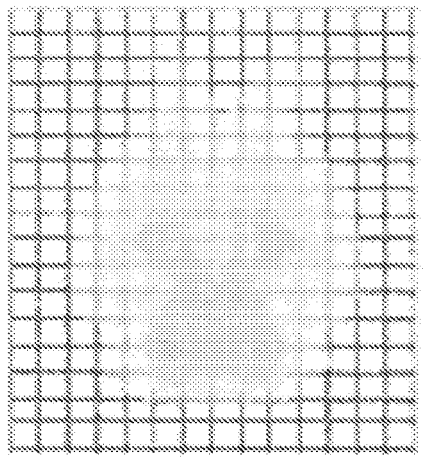
FIG.22
BRAIN TREATED WITH #0640 #1352 MIXED SOLUTION
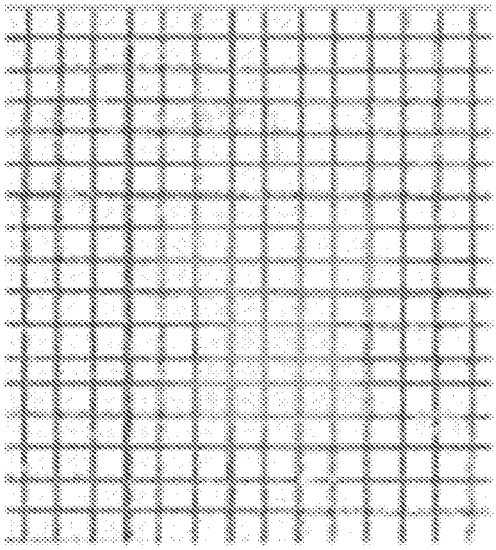

FIG.23
10 wt% #0070
+ 10 wt% #0631
| Delipidation 2 days at 50°C | Wash 6 h | RI matching overnight at 50°C |
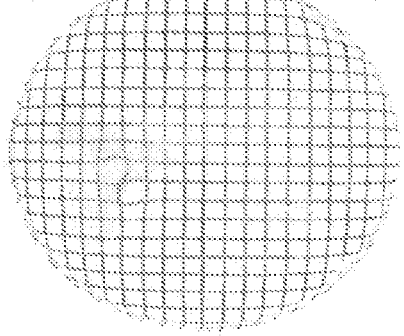
Mouse Liver
20 wt% #0070
+ 10 wt% SDS
| Delipidation 4 days at 37°C | Wash 6 h | RI matching overnight at 50°C |
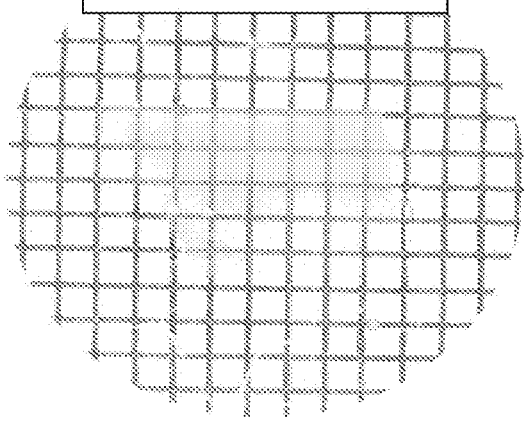
Human Brain Brain

FIG. 30

Table 1. A list of top 50 chemicals with highest delipidation

| CUBIC ID | Chemical name | Group | CAS no. | Chemical structure | 1st delipidation assay Relative OD600 | S.D. | 1st quenching assay Relative Fluorescence of Sirius | S.D. | 2nd delipidation assay | 2nd quenching assay EGFP fluorescence | S.D. | OD400 | pH | Catalog no. | Cost/unit (1 g or 1 mL/yen) |
|---|---|---|---|---|---|---|---|---|---|---|---|---|---|---|---|
| Detergents | | | | | | | | | | | | | | | |
| #1455 | Tween® 40 | Polyether | 9005-66-7 | 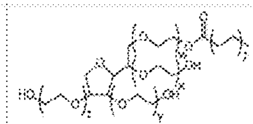 | 0.073 | 0.010 | 0.84 | 0.05 | | | | 0.083 | 6.4 | T0544 | 5.6 |
| #1460 | Tween® 80 | Polyether | 9005-65-6 | 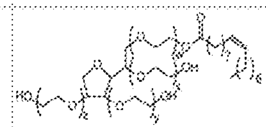 | 0.095 | 0.145 | 0.91 | 0.01 | | | | 0.065 | 5.7 | T0546 | 5.4 |
| #1035 | Sodium dodecyl sulfate | Anionic detergent | 151-21-3 | 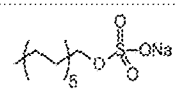 | 0.106 | 0.030 | 1.15 | 0.05 | | | | 0.048 | 6.3 | I0352 | 23.4 |
| #1419 | Sodium 1-undecanesulfonate | Anionic detergent | 5838-34-6 | 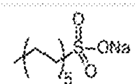 | 0.124 | 0.041 | 1.03 | 0.00 | | | | 0.056 | 5.9 | U0031 | 484 |
| #0872 | Dodecene-1 LAS | Anionic detergent | 25155-30-0 | 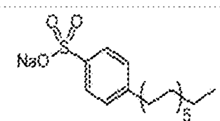 | 0.152 | 0.015 | 1.08 | 0.05 | | | | 0.081 | 5.9 | D1428 | 7500 |
| #1310 | Lithium dodecyl sulfate | Anionic detergent | 2044-56-6 | 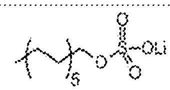 | 0.155 | 0.020 | 1.13 | 0.01 | | | | 0.047 | 6.7 | L0254 | 632 |
| #0865 | Sodium nonanoate | Anionic detergent | 14047-60-0 | 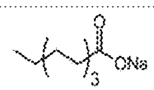 | 0.155 | 0.030 | 1.03 | 0.02 | | | | 0.051 | 6.9 | N0291 | 220 |

FIG. 30 (CONT.)

| ID | Name | Type | CAS | Structure | | | | | | | | |
|---|---|---|---|---|---|---|---|---|---|---|---|---|
| #0631 (=#0672) | Sodium dodecylbenzenesulfonate | Anionic detergent | 25155-30-0 | | 0.163 | 0.020 | 0.69 | 0.01 | | 0.09 | 6.0 | D0989 | 11 |
| #0562 | Sodium deoxycholate | Anionic detergent | 302-95-4 | | 0.170 | 0.010 | 1.08 | 0.01 | | 0.054 | 8.3 | C0316 | 268 |
| #1103 | Polyethylene glycol mono-4-octylphenyl ether | Polyether | 9002-93-1 | | 0.184 | 0.080 | 1.28 | 0.13 | | 0.051 | 5.6 | P0873 | 14.2 |
| #1511 | Nonidet P-40 | Polyether | 9016-45-9 | | 0.193 | 0.015 | 1.05 | 0.01 | | 0.057 | 5.8 | Nacalai, @@@ | 39 |
| #1021 | Dodecyltrimethylammonium chloride | Cationic detergent | 112-00-5 | | 0.194 | 0.025 | 1.11 | 0.00 | | 0.048 | 7.5 | I0453 | 105.4 |
| #0703 | Decanoylsarcosine sodium salt | Anionic detergent | 30377-07-2 | | 0.223 | 0.055 | 1.03 | 0.03 | | 0.047 | 7.0 | D2469 | 2180 |
| #1466 | Sodium N-lauroylsarcosinate | Anionic detergent | 137-16-6 | | 0.237 | 0.015 | 1.02 | 0.00 | | 0.05 | 6.1 | S0597 | 204 |
| | Triton™ X-100 | Polyether | 9002-93-1 | | 0.240 | 0.120 | 1.04 | 0.02 | | 0.051 | 5.8 | Nacalai, @@@ | 14.2 |
| #0651 | Decyldimethyl(3-sulfopropyl)ammonium | Amphiphilic detergent | 15163-36-7 | | 0.244 | 0.075 | 0.97 | 0.00 | | 0.048 | 7.5 | D4246 | 1260 |
| #0870 | Sodium 1-nonanesulfonate | Anionic detergent | 35192-74-6 | | 0.247 | 0.110 | 1.05 | 0.03 | | 0.047 | 6.8 | N0311 | 464 |

FIG. 30 (CONT.)

| # | Name | Type | CAS | Structure | | | | | | | |
|---|---|---|---|---|---|---|---|---|---|---|---|
| #0566 | Sodium Cholate | Anionic detergent | 361-09-1 | | 0.254 | 0.040 | 1.07 | 0.06 | | 0.052 | 6.7 | C0325 | 84.4 |
| #0661 | Dodecyldimethyl(3-sulfopropyl)am monium | Amphiphilic detergent | 14933-08-5 | | 0.258 | 0.015 | 1.13 | 0.02 | | 0.051 | 6.5 | D3860 | 352 |
| #1507 (=#0562) | Sodium deoxycholate | Anionic detergent | 302-95-4 | | 0.303 | 0.005 | 1.03 | 0.00 | | 0.054 | 7.9 | C0316 | 268 |
| #0635 | 1-Dodecylpyridinium chloride | Cationic detergent | 104-74-5 | | 0.304 | 0.020 | 1.04 | 0.02 | | 0.053 | 8.9 | D0995 | 45 |
| #1162 | Ammonium pentadecafluor ooctanoate | Anionic detergent | 3825-26-1 | | 0.318 | 0.020 | 1.43 | 0.02 | | 0.048 | 5.2 | P1449 | 356 |
| #0825 | Sodium 1-decanesulfonate | Anionic detergent | 13419-61-9 | | 0.325 | 0.020 | 0.93 | 0.25 | | 0.046 | 5.9 | D1181 | 424 |
| #0627 | Dodecylamine acetate | Cationic detergent | 2016-56-0 | | 0.329 | 0.035 | 1.05 | 0.01 | | 0.053 | 10.3 | D0981 | 384 |
| #1235 | Hexadecyltrime thylammonium chloride | Cationic detergent | 112-02-7 | | 0.332 | 0.090 | 1.06 | 0.01 | | 0.048 | 6.6 | H0082 | 58.8 |
| Hydrophilic molecules | | | | | | | | | | | | |
| #1444 | 1,1,3,3-Tetramethylgua nidine | Amine | 80-70-6 | | 0.124 | 0.010 | 0.14 | | | 0.072 | 12.4 | T0148 | 49.6 |
| #1456 | N,N,N',N'-Tetramethyl-1,6-diaminohexane | Amine | 111-18-2 | | 0.135 | 0.005 | 0.63 | 0.02 | | 0.058 | 12.7 | T0537 | 18.4 |

FIG. 30 (CONT.)

| # | Name | Type | CAS | Structure | | | | | | | |
|---|---|---|---|---|---|---|---|---|---|---|---|
| #1097 | Piperidine | Amine | 110-89-4 | | 0.166 | 0.015 | 0.33 | 0.00 | 0.051 | 13.2 | P0453 | 11.6 |
| #1602 | Isophoronediamine | Amine | 2855-13-2 | | 0.190 | 0.010 | 0.53 | 0.01 | 0.051 | 10.8 | I0228 | 12.2 |
| #1093 | Propylamine | Amine | 107-10-8 | | 0.206 | 0.005 | 0.60 | 0.03 | 0.052 | 13.1 | P0520 | 9.4 |
| #1027 | N-Isopropyl-1,3-diaminopropane | Amine | 3360-16-5 | | 0.219 | 0.000 | 0.55 | 0.02 | 0.061 | 13.4 | I0420 | 392 |
| #1267 | 2-Methyl-1,5-diaminopentane | Amine | 15520-10-2 | | 0.244 | 0.025 | 0.51 | 0.01 | 0.08 | 12.9 | M0205 | 8.2 |
| #1036 | Isoamylamine | Amine | 107-85-7 | | 0.247 | 0.080 | 0.30 | 0.03 | 0.055 | 9.6 | I0082 | 76.4 |
| #1043 | Isobutylamine | Amine | 78-81-9 | | 0.251 | 0.005 | 0.48 | 0.03 | 0.049 | 12.0 | I0095 | 11.2 |
| #0387 | Benzyltrimethylammonium Hydroxide | Amine | 100-85-6 | | 0.268 | 0.005 | 0.00 | 0.00 | 0.054 | 13.8 | B1071 | 39.4 |
| #0414 | N-Butyldiethanolamine | Aminoalcohol | 102-79-4 | | 0.281 | 0.000 | 0.70 | 0.04 | 0.05 | 12.7 | B0725 | 15 |
| #0070 | 1,3-Bisaminomethylcyclohexane | Amine | 2579-20-6 | | 0.286 | 0.015 | 0.52 | 0.01 | 0.079 | 13.0 | B1005 | 18.8 |
| #1462 | Tropine | Aminoalcohol | 120-29-6 | | 0.292 | 0.000 | 0.56 | 0.02 | 0.053 | 12.9 | T0534 | 524 |
| #1051 | 1,2-Hexanediol | Polyalcohol | 6920-22-5 | | 0.300 | 0.015 | 0.84 | 0.05 | 0.048 | 9.3 | H0888 | 67 |
| #1541 | Allylamine | Amine | 107-11-9 | | 0.303 | 0.015 | 0.56 | 0.01 | 0.068 | 10.7 | A0219 | 14.2 |

FIG. 30 (CONT.)

| # | Name | Category | CAS | Structure | | | | | | | |
|---|---|---|---|---|---|---|---|---|---|---|---|
| #0422 | N-Butylethylenediamine | Amine | 19522-69-1 | | 0.307 | 0.085 | 0.68 | 0.00 | | | |
| #0441 | Benzethonium Chloride | Detergent like aromatic ether | 121-54-0 | 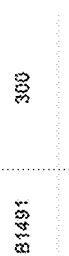 | 0.307 | 0.105 | 1.08 | 0.03 | | B1491 | 41.2 |
| #1008 | 2,6-Lutidine | Pyridine | 108-48-5 | 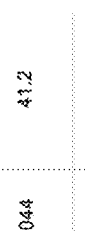 | 0.314 | 0.095 | 0.71 | 0.02 | 0.063 | 9.9 | L0067 | 19 |
| #0664 | 6-Dimethylamino-1-hexanol | Aminoalcohol | 1862-07-3 |  | 0.314 | 0.085 | 0.69 | 0.04 | 0.062 | 13.1 | D1664 | 396 |
| #0390 | N-tert-Butyldiethanolamine | Aminoalcohol | 2160-93-2 | 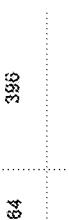 | 0.318 | 0.030 | 0.72 | 0.01 | 0.052 | 12.7 | B1194 | 18.4 |
| #0071 | 1,4-Bis(aminomethyl)cyclohexane | Amine | 2549-93-1 | 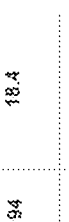 | 0.318 | 0.040 | 0.56 | 0.00 | 0.054 | 13.3 | B1083 | 432 |
| #1006 | Isopropylamine | Amine | 75-31-0 |  | 0.325 | 0.050 | 0.58 | 0.00 | 0.047 | 13.1 | I0165 | 6.2 |
| #1312 | 2,4-Lutidine | Pyridine | 108-47-4 | 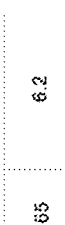 | 0.325 | 0.020 | 0.84 | 0.01 | 0.051 | 7.6 | L0085 | 32.8 |
| #1295 | 1-Methylpyrrolidin e | Amine | 120-94-5 | 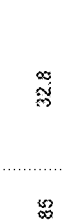 | 0.336 | 0.010 | 0.66 | 0.02 | 0.085 | 10.5 | M0415 | 32.4 |
| #1074 | 1-Phenylethane-1,2-diol | Polyalcohol | 93-56-1 | 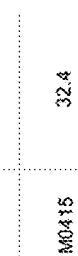 | 0.336 | 0.005 | 0.58 | 0.00 | 0.05 | 9.5 | P0686 | 203.6 |
| | Quadrol® (ScaleCUBIC-1) | | 102-60-3 |  | 0.569 | 0.105 | 0.57 | 0.01 | 0.048 | 12.4 | T0781 | 8.6 |

FIG. 30 (CONT.)
| | | | | | | | | | |
|---|---|---|---|---|---|---|---|---|---|
| Triethanolamine (TEA, ScaleCUBIC-2) | 102-71-6 |  | 0.664 | 0.030 | 0.65 | 0.05 | 0.048 | 12.0 | S0377 (Wako, 145-05605) |
| Urea (Scale) | 57-13-6 | 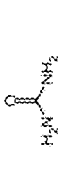 | 0.781 | 0.025 | 0.81 | 0.06 | 0.048 | 7.5 | U0077 |
| PBS | | | 1.000 | 0.015 | 1.00 | 0.00 | 0.046 | 7.9 | 660 (Wako, 3) 4.7 |

FIG. 31

Table 2. A list for 65 chemicals with highest decolorization

| CUBIC ID | Chemical name | Group | CAS no. | Chemical structure | Fluorescence quench 400 nm | | | 700 nm calibrated 420 nm | | integrated value 500 - 700 nm | | Catalog no. | Cost/unit |
|---|---|---|---|---|---|---|---|---|---|---|---|---|---|
| | | | | | Average | S.D. | pH | Average | S.D. | Average | S.D. | | |
| #0936 | 1-Ethylimidazole | Alkylimidazole | 7098-07-9 | | 0.053 | 0.01 | 12.1 | 6.19 | 0.36 | 3.41 | 0.48 | E0132 | 176 |
| #0484 | 1-Methylimidazole | Alkylimidazole | 616-47-7 | | 0.05 | | | | | | | M0508 | |
| #0197 | 1-(3-Aminopropyl)imidazole | Alkylimidazole | 5036-48-6 | | 0.047 | 0.03 | 12.9 | 4.81 | 0.02 | 2.64 | 0.03 | A1185 | 60.6 |
| #0470 (=#1240) | Tris(2-carboxyethyl)phosphine hydrochloride | Phosphine | 51805-45-9 | | 0.064 | 0.06 | 2.3 | 4.28 | 0.05 | 3.89 | 0.06 | T1656 | 3480 |
| #1240 (=#0470) | Cetylpyridinium chloride monohydrate | Detergent | 6004-24-6 | | 0.05 | 0.01 | 8.0 | 4.20 | 0.04 | 3.80 | 0.03 | A5161 (=H0078) | 600 |
| #0635 | Hexadecylpyridinium chloride monohydrate | Detergent | 6004-24-6 | | 0.053 | 0.03 | 6.9 | 4.18 | 0.14 | 3.84 | 0.17 | H0078 (A5161) | 35.2 |
| #0651 | 1-Dodecylpyridinium chloride | Detergent | 104-74-5 | | 0.048 | 0.02 | 8.9 | 3.86 | 0.11 | 3.57 | 0.11 | D0995 | 45 |
| #0441 | Decyldimethyl(3-sulfopropyl)ammonium hydroxide | Detergent | 15163-36-7 | | 0.049 | 0.00 | 7.5 | 3.73 | 0.15 | 3.28 | 0.18 | D4246 | 1260 |
| | Benzethonium chloride | Detergent | 121-54-0 | | 0.049 | 0.03 | 6.4 | 3.40 | 0.24 | 2.80 | 0.14 | B0044 | 41.2 |

FIG. 31 (CONT.)

| | | | | | | | | | | | | |
|---|---|---|---|---|---|---|---|---|---|---|---|---|
| #0394 | Bis(3-aminopropyl) ether | Amine | 2157-24-6 | (structure) | 0.067 | 0.54 | 0.07 | 13.2 | 3.27 | 0.10 | 1.85 | 0.00 | B1268 | 3540 |
| #0071 | 1,4-Bis(aminomethyl) cyclohexane | Amine | 2549-93-1 | (structure) | 0.054 | 0.56 | 0.00 | 13.3 | 3.25 | 0.30 | 1.90 | 0.21 | B1063 | 432 |
| #0070 | 1,3-Bis(aminomethyl) cyclohexane | Amine | 2579-20-6 | (structure) | 0.079 | 0.52 | 0.01 | 13.0 | 3.15 | 0.04 | 1.91 | 0.03 | B1005 | 18.8 |
| #0387 (=#0398) | Benzyltrimethyla mmonium hydroxide | Amine | 100-85-6 | (structure) | 0.054 | 0.00 | 0.00 | 13.8 | 3.14 | 0.02 | 2.58 | 0.03 | B1071 (=B0448) | 39.4 |
| #0594 | 1,8-Diazabicyclo[5.4.0]-7-undecene | Amine | 6674-22-2 | (structure) | 0.05 | 0.54 | 0.00 | 13.5 | 3.13 | 0.15 | 1.94 | 0.12 | D1270 | 31.4 |
| #1283 | N-Methylnicotinamid e | Pyridine | 114-33-0 | (structure) | 0.063 | 0.71 | 0.03 | 10.7 | 2.98 | 0.16 | 2.81 | 0.11 | M0374 | 356 |
| #1235 | Hexadecyltrimeth ylammonium Chloride | Detergent | 112-02-7 | (structure) | 0.048 | 1.06 | 0.01 | 6.6 | 2.85 | 0.28 | 2.71 | 0.47 | H0082 | 58.8 |
| #0389 | N-Benzylethanolami ne | Aminoalcohol | 104-63-2 | (structure) | 0.063 | 0.57 | 0.01 | 10.9 | 2.73 | 0.02 | 2.42 | 0.05 | B1130 | 21.6 |
| #0807 | 6-Amino-1-hexanol | Aminoalcohol | 4048-33-3 | (structure) | 0.093 | 0.22 | 0.20 | 11.9 | 2.66 | 0.05 | 1.76 | 0.05 | A1027 | 756 |
| #0370 | 2-Amino-6-methylpyridine | Pyridine | 1824-81-3 | (structure) | 0.064 | 0.67 | 0.01 | 11.3 | 2.66 | 0.28 | 2.57 | 0.26 | A0403 | 30.6 |
| #0664 | 6-Dimethylamino-1-hexanol | Aminoalcohol | 1862-07-3 | (structure) | 0.062 | 0.69 | 0.04 | 13.1 | 2.64 | 0.07 | 2.72 | 0.08 | D1664 | 396 |

FIG. 31 (CONT.)

| # | Name | Category | CAS | Structure | | | | | | | | | |
|---|---|---|---|---|---|---|---|---|---|---|---|---|---|
| #0855 | Nicotinamide | Pyridine | 98-92-0 | | 0.052 | 0.75 | 0.01 | 10.4 | 2.63 | 0.05 | 2.45 | 0.07 | N0078 | 12.8 |
| #0380 | 3,3'-Diamino-N-methyldipropylamine | Amine | 105-83-9 | | 0.065 | 0.62 | 0.03 | 13.0 | 2.62 | 0.05 | 1.58 | 0.03 | B0821 | 16.6 |
| #1312 | 2,4-Lutidine | Pyridine | 108-47-4 | | 0.051 | 0.84 | 0.01 | 7.6 | 2.47 | 0.02 | 2.59 | 0.01 | L0085 | 32.8 |
| #1102 | 3-Picolylamine | Pyridine | 3731-52-0 | | 0.056 | 0.77 | 0.02 | 11.8 | 2.46 | 0.05 | 1.32 | 0.04 | P0762 | 42.4 |
| #1575 | 2-Diethylaminoethanol | Aminoalcohol | 100-37-8 | | 0.06 | 0.61 | 0.00 | 12.8 | 2.41 | 0.22 | 1.21 | 0.10 | D0465 | 5.8 |
| #0587 | 1,5-Diazabicyclo[4.3.0]-5-nonene | Amine | 3001-72-7 | | 0.049 | 0.72 | 0.01 | 12.6 | 2.41 | 0.04 | 1.38 | 0.03 | D1313 | 156.8 |
| #0694 (=#0661) | Dodecyldimethyl-3-sulfopropylammonium hydroxide | Detergent | 14933-08-5 | | 0.055 | 1.09 | 0.03 | 8.4 | 2.24 | 0.09 | 2.53 | 0.72 | D2332 (=D3860) | 137.2 |
| #0783 | 1,4-Diaminobutane | Amine | 110-60-1 | | 0.05 | 0.60 | 0.00 | 14.0 | 2.21 | 0.00 | 1.42 | 0.02 | D0239 | 22.75 |
| #0627 | Dodecylamine acetate | Detergent | 2016-56-0 | | 0.053 | 1.05 | 0.01 | 10.3 | 2.21 | 0.03 | 1.74 | 0.02 | D9981 | 384 |
| #1228 | 1-(2-Hydroxyethyl)-4-(3-hydroxypropyl)piperidine | Aminoalcohol | 19780-85-9 | | 0.05 | 0.78 | 0.01 | 14.1 | 2.20 | 0.08 | 2.29 | 0.14 | H0360 | 368 |
| #1456 | N,N,N',N'-Tetramethyl-1,6-diaminohexane | Amine | 111-18-2 | | 0.058 | 0.63 | 0.02 | 12.7 | 2.17 | 0.48 | 2.11 | 0.47 | T0537 | 18.4 |

FIG. 31 (CONT.)

| | | | | | | | | | | | | |
|---|---|---|---|---|---|---|---|---|---|---|---|---|
| #0362 | Benzyldimethyltetradecylammonium chloride hydrate | Detergent | 1139-08-2 | | 0.053 | 1.07 | 0.00 | 6.6 | 2.13 | 0.12 | 1.74 | 0.06 | A0208 | 32.6 |
| #0661 (=#0694) | Dodecyldimethyl-3-sulfopropylammonium hydroxide | Detergent | 14933-08-5 | | 0.061 | 1.13 | 0.02 | 6.5 | 2.10 | 0.10 | 1.70 | 0.11 | D3880 (=D2332) | 352 |
| #0785 | 3,3'-Diaminodipropylamine | Amine | 56-18-8 | | 0.05 | 0.62 | 0.01 | 13.8 | 2.09 | 0.05 | 1.48 | 0.04 | D0090 | 17.4 |
| #0398 (=#0387) | Benzyltrimethylammonium hydroxide | | 100-85-6 | | 0.054 | 0.00 | 0.00 | 12.9 | 2.09 | 0.03 | 1.77 | 0.05 | B0446 (=B1071) | 16.4 |
| #1602 | Isophoronediamine | Amine | 2855-13-2 | | 0.051 | 0.53 | 0.01 | 10.8 | 2.08 | 0.32 | 1.26 | 0.18 | I0228 | 12.2 |
| #0652 | 1,1'-Dimethyl-4,4'-bipyridinium dichloride | Pyridine | 1910-42-5 | | 0.082 | 0.42 | 0.01 | 6.0 | 2.01 | 0.12 | 2.01 | 0.14 | D3685 | 2480 |
| #1008 | 2,6-Lutidine | Pyridine | 108-48-5 | | 0.063 | 0.71 | 0.02 | 9.9 | 2.00 | 0.10 | 2.16 | 0.07 | L0067 | 19 |
| #1021 | Dodecyltrimethylammonium chloride | Detergent | 112-00-5 | | 0.048 | 1.11 | 0.00 | 7.5 | 1.96 | 0.08 | 1.70 | 0.11 | I0453 | 105.4 |
| #0003 | 5-Amino-1-pentanol | Aminoalcohol | 2508-29-4 | | 0.052 | 0.63 | 0.01 | 12.5 | 1.83 | 0.22 | 1.21 | 0.17 | A0875 | 182.8 |
| #0678 | 1,3-Diaminopentane | Amine | 589-37-7 | | 0.049 | 0.60 | 0.01 | 13.6 | 1.71 | 0.04 | 1.15 | 0.04 | D2252 | 23.8 |
| #1027 | N-Isopropyl-1,3-diaminopropane | Amine | 3380-16-5 | | 0.061 | 0.55 | 0.02 | 13.4 | 1.52 | 0.07 | 1.24 | 0.11 | I0420 | 392 |
| #0467 | 4-Aminomethyltetrahydropyran | Amine | 130290-79-8 | | 0.049 | 0.65 | 0.01 | 12.9 | 1.52 | 0.14 | 1.13 | 0.19 | A2550 | 4400 |

FIG. 31 (CONT.)

| # | Name | Category | CAS | Structure | | | | | | | | Code | |
|---|---|---|---|---|---|---|---|---|---|---|---|---|---|
| #1267 | 2-Methyl-1,5-diaminopentane | Amine | 15520-10-2 | | 0.08 | 0.51 | 0.01 | 12.9 | 1.48 | 0.09 | 1.09 | 0.09 | M0205 | 8.2 |
| #1367 | 5-Bromo-1-pentanol | Alcohol | 34626-51-2 | | 0.055 | -0.01 | 0.00 | 2.9 | 1.48 | 0.00 | 0.06 | 0.06 | B1848 | 920 |
| #1422 | Veratryl alcohol | Alcohol | 93-03-8 | | 0.05 | 0.89 | 0.04 | 6.1 | 1.46 | 0.52 | 1.28 | 0.56 | V0020 | 308 |
| #0672 | Dodecene-1 LAS (JIS K 3363-1990) | Detergent | 25155-30-0 | | 0.081 | 1.08 | 0.05 | 5.9 | 1.45 | 0.04 | 1.41 | 0.04 | D1428 | 7500 |
| #1086 | Pyrazine | Pyridine | 290-37-9 | | 0.051 | 0.67 | 0.01 | 8.6 | 1.41 | 0.13 | 1.39 | 0.15 | P0544 | 64.8 |
| #0779 | N,N'-Diethylethylenediamine | Amine | 100-36-7 | | 0.051 | 0.70 | 0.02 | 13.6 | 1.39 | 0.04 | 0.81 | 0.01 | D0505 | 21.6 |
| #1167 | 1-(2-Pyrimidyl)piperazine | Amine | 20980-22-7 | | 0.084 | 0.01 | 0.01 | 12.5 | 1.39 | 0.06 | 1.09 | 0.07 | P1110 | 412 |
| #1455 | Tween®40 | Detergent | 9005-66-7 | | 0.083 | 0.64 | 0.05 | 6.4 | 1.38 | 0.45 | 1.21 | 0.40 | T0544 | 5.8 |
| #1444 | 1,1,3,3-Tetramethylguanidine | Amine | 80-70-6 | | 0.072 | 0.14 | 0.01 | 12.4 | 1.38 | 0.12 | 1.15 | 0.08 | T0148 | 49.6 |
| #0414 | N-Butyldiethanolamine | Aminoalcohol | 102-79-4 | | 0.05 | 0.70 | 0.04 | 12.7 | 1.30 | 0.00 | 1.45 | 0.08 | B0725 | 15 |
| #1537 | N,N,N',N'-Tetrakis(2-hydroxyethyl)ethylenediamine | Aminoalcohol | 140-07-8 | | 0.048 | 0.66 | 0.01 | 11.7 | 1.29 | 0.11 | 1.63 | 0.18 | T0120 | 184 |

FIG. 31 (CONT.)

| # | Name | Type | CAS | Structure | | | | | | | | | | | |
|---|---|---|---|---|---|---|---|---|---|---|---|---|---|---|---|
| #1035 | Sodium dodecyl sulfate | Detergent | 151-21-3 | | 0.048 | 1.15 | 0.05 | 6.3 | 1.28 | 0.34 | 1.32 | 0.42 | I0352 | 23.4 |
| #1507 (=#0562) | Sodium deoxycholate | Detergent | 302-95-4 | | 0.054 | 1.03 | 0.00 | 7.9 | 1.27 | 0.01 | 1.03 | 0.04 | C0316 | 268 |
| #0788 | N,N-Dimethylbenzamide | Benzyl amide | 611-74-5 | | 0.049 | 0.76 | 0.00 | 10.7 | 1.26 | 0.16 | 1.08 | 0.16 | D0256 | 66.8 |
| #0840 | 2,3-Dimethyl-1-phenyl-5-pyrazolone | Pyrazolone | 60-80-0 | | 0.048 | 0.84 | 0.01 | 7.5 | 1.22 | 0.27 | 0.93 | 0.25 | D1876 | 27.2 |
| #0006 | 4-Amino-1-butanol | Aminoalcohol | 13325-10-5 | | 0.06 | 0.64 | 0.03 | 12.3 | 1.22 | 0.00 | 0.82 | 0.02 | A1013 | 1172 |
| #1105 | N,N,N',N'-Pentakis(2-hydroxypropyl)ethylenetriamine | Aminoalcohol | 17121-34-5 | | 0.057 | 0.74 | 0.04 | 13.2 | 1.20 | 0.10 | 1.05 | 0.11 | P0832 | 49.6 |
| #0277 | N,N'-Bis(3-aminopropyl)ethylenediamine | Amine | 10563-26-5 | | 0.053 | 0.71 | 0.01 | 13.1 | 1.20 | 0.02 | 0.83 | 0.01 | B1952 | 16.6 |
| #0562 (=#1507) | Sodium deoxycholate | Detergent | 302-95-4 | | 0.054 | 1.08 | 0.01 | 8.3 | 1.18 | 0.04 | 0.98 | 0.03 | C0316 | 268 |
| #1061 | 1-(2-Hydroxyethyl)ethyleneimine | Aminoalcohol | 1072-52-2 | | 0.048 | 0.80 | 0.02 | 13.1 | 1.14 | 0.04 | 0.91 | 0.02 | H0567 | 444 |
| #0425 | Benzyltriphenylphosphonium chloride | Phosphine | 1100-88-5 | | 0.048 | 0.35 | 0.01 | 9.3 | 1.14 | 0.02 | 0.83 | 0.01 | B0824 | 43.2 |

FIG. 32

Table 3. A list of top 27 chemicals with highest RI and water-solubility

| CUBIC ID | Chemical name | Group | CAS no. | Chemical structure | 1st RI evaluation assay RI of 10% chemical | 1st quenching assay Relative Fluorescence of Sirius | S.D. | Chemical conc. (wt%) | 2nd quenching assay RI | EGFP fluorescence | S.D | OD 400 | pH | Catalog no. | Cost/unit (1g or 1 mL/yen) |
|---|---|---|---|---|---|---|---|---|---|---|---|---|---|---|---|
| #0640 | 2,3-Dimethyl-1-phenyl-5-pyrazolone | Benzyl amine | 60-80-0 | | 1.3549 | 0.84 | 0.01 | 60 | 1.4966 | quench free | | 0.048 | 7.5 | D1876 | 27.2 |
| #1612 | Xylazine hydrochloride | Benzyl amine | 23076-35-9 | | 1.3519 | 0.97 | 0.00 | 70 | 1.4956 | | | 0.053 | 5.8 | X0059 | 1460 |
| #0370 | 2-Amino-6-methylpyridine | Pyridine | 1824-81-3 | | 1.3555 | 0.67 | 0.01 | 70 | 1.4822 | | | 0.064 | 11.3 | A0403 | 30.6 |
| #1140 | 2-Methylpyridine N-oxide | Pyridine | 931-19-1 | | 1.3511 | 1.04 | 0.00 | 70 | 1.4919 | | | 0.049 | 6.2 | P0418 | 74 |
| #0930 | S-(2-(Dimethylamino)ethyl)is othiourea dihydrochloride | Amine | 16111-27-6 | | 1.3527 | 1.06 | 0.02 | 70 | 1.5021 | | | 0.047 | 5.4 | D0852 | 510 |
| #1181 | Phthalimide DBU salt | Amine | 119812-51-0 | | 1.3526 | 0.94 | 0.00 | 60 | @ | | | 0.049 | 6.0 | P1235 | 404 |
| #0809 | Diphenhydramine hydrochloride | Benzyl amine | 147-24-0 | | 1.3525 | 0.90 | 0.00 | 70 | 1.4990 | | | 0.048 | 7.0 | D0423 | 59.4 |
| #0450 | Benzyldimethylphenyla mmonium chloride | Benzyl amine | 3204-68-0 | | 1.3525 | 0.72 | 0.02 | 70 | 1.5002 | quench free | | 0.052 | 6.7 | B0416 | 308 |
| #1142 | DL-Phenylephrine hydrochloride | Benzyl aminoalcohol | 154-86-9 | | 1.3539 | 0.93 | 0.04 | 70 | 1.4854 | | | 0.066 | 5.7 | P0397 | 432 |
| #1145 | 4-Methylpyridine N-oxide | Pyridine | 1003-67-4 | | 1.3535 | 0.98 | 0.03 | 70 | 1.5073 | | | 0.059 | 7.3 | P0420 | 252 |
| #1283 | N-Methylnicotinamide | Pyridine | 114-33-0 | | 1.3532 | 0.71 | 0.03 | 70 | 1.4802 | quench free | | 0.063 | 10.7 | M0374 | 356 |

FIG. 32 (CONT.)

| | | | | | | | | | | | | |
|---|---|---|---|---|---|---|---|---|---|---|---|---|
| #1382 | Tolperisone hydrochloride | Benzyl amine | 3644-61-9 | | 1.3522 | 0.69 | 0.01 | 70 | 1.4939 | | 0.056 | 5.2 | T1319 | 164 |
| #0299 | Bis(2-dimethylaminoethyl) disulfide dihydrochloride | Amine | 17339-60-5 | | 1.3523 | 1.04 | 0.01 | 70 | 1.4937 | | 0.047 | 5.3 | B2272 | 184 |
| #1102 | 3-Picolylamine | Pyridine | 3731-52-0 | | 1.3527 | 0.77 | 0.02 | 70 | 1.4895 | | 0.056 | 11.6 | P0762 | 42.4 |
| #0864 | Neostigmine bromide | Benzyl amine | 114-80-7 | | 1.3503 | 0.99 | 0.02 | 70 | 1.4830 | quench free | 0.051 | 6.0 | N0358 | 704 |
| #1052 | Hydrazine carbonate | Hydrazine | 112077-84-6 | | 1.3510 | 1.04 | 0.03 | 70 | 1.4799 | quench free | 0.047 | 10.2 | H0854 | 15.4 |
| #0788 | N,N-Dimethylbenzamide | Benzyl amide | 611-74-5 | | 1.3505 | 0.76 | 0.00 | 70 | 1.4833 | quench free | 0.049 | 10.7 | D0256 | 66.8 |
| #0389 | N-Benzylethanolamine | Benzyl aminoalcoho... | 104-63-2 | | 1.3524 | 0.57 | 0.01 | 70 | 1.4814 | quench free | 0.063 | 10.9 | B1130 | 21.6 |
| #0307 | Benzyltributylammonium chloride | Benzyl amine | 23616-79-7 | | 1.3507 | 0.90 | 0.03 | 80 | 1.4939 | | 0.048 | 7.0 | B1384 | 27.8 |
| #0587 | 1,5-Diazabicyclo[4.3.0]-5-nonene | Amine | 3001-72-7 | | 1.3501 | 0.72 | 0.01 | 75 | 1.4836 | | 0.049 | 12.6 | D1313 | 156.8 |
| #0338 | N-(2-Aminoethyl)piperazine | Amine | 140-31-8 | | 1.3507 | 0.86 | 0.02 | 75 | 1.4794 | | 0.062 | 12.4 | A0304 | 9.8 |
| #0315 | 1-Butylpyridinium bromide | Pyridine | 874-80-6 | | 1.3504 | 1.11 | 0.01 | 85 | 1.5090 | | 0.048 | 5.6 | B1743 | 488 |
| #0609 | N,N-Diethylnicotinamide | Pyridine | 59-26-7 | | 1.3502 | 1.03 | 0.01 | 80 | 1.4928 | | 0.056 | 6.4 | D0514 | 62.8 |
| #1076 | Pyridine N-oxide | Pyridine | 694-59-7 | | 1.3518 | 0.98 | 0.00 | 60 | 1.4795 | | 0.064 | 6.1 | P0557 | 55.8 |
| #0785 | 3,3'-Diaminodipropylamine | Amine | 56-18-8 | | 1.3502 | 0.62 | 0.01 | 100 | 1.4895 | | 0.050 | 13.8 | D0090 | 17.4 |

FIG. 32 (CONT.)

| ID | Name | Subcategory | CAS | Structure | Val1 | Val2 | Val3 | Val4 | Val5 | Val6 | Val7 | Catalog | Val8 |
|---|---|---|---|---|---|---|---|---|---|---|---|---|---|
| #0415 | 1-Butylpyridinium chloride | Pyridine | 1124-64-7 | (structure) | 1.3505 | 0.99 | 0.00 | 90 | 1.4824 | 0.055 | 5.5 | B1329 | 566 |
| #0637 | 1,3-Dimethylthiourea | Urea | 534-13-4 | (structure) | 1.3555 | 1.05 | 0.01 | | | 0.049 | 6.8 | D0804 | 38.8 |
| | Diatrizoic acid (FocusClear™) | | 737-31-5 | (structure) | | #DIV/0! | #DIV/0! | | | | | D1462 | 296 |
| #0956 | D-Glucamine (FocusClear™) | | 488-43-7 | (structure) | 1.3475 | 0.42 | 0.01 | | | 0.260 | 12.3 | G0252 | 800 |
| | D-(-)-Fructose (SeeDB) | | 57-48-7 | (structure) | | #DIV/0! | #DIV/0! | | | | | F0060 | 6.6 |
| | D-(+)-Sucrose (CUBIC-2) | | 57-50-1 | (structure) | 1.3472 | 0.92 | 0.01 | | | 0.048 | 6.5 | S0111 | 4.8 |
| | Histodenz™ (RIMS) | | 66108-95-0 | (structure) | 1.3490 | 0.84 | 0.03 | | | 0.054 | 7.3 | D2158 (SIGMA) | 501 |
| | PBS | | | | 1.3350 | 1.00 | 0.00 | | | 0.046 | 7.9 | | |

METHOD FOR PREPARING BIOLOGICAL MATERIAL HAVING EXCELLENT LIGHT-TRANSMITTING PROPERTY

CROSS REFERENCE TO RELATED APPLICATIONS

This is a Continuation application of U.S. application Ser. No. 16/096,130 filed on Oct. 24, 2018, which is a U.S. National Stage application of PCT/JP2017/016410 filed on Apr. 25, 2017, which claims priority to Japanese Patent Application, Tokugan, No. 2016-092025 filed on Apr. 28, 2016, the contents of each of which are hereby incorporated herein by reference.

TECHNICAL FIELD

The present invention relates to a composition for preparing a biological material having an excellent light-transmitting property and to use of the composition.

BACKGROUND ART

For high-level observations of gene expression within tissue, intracellular localization, and cell morphology, a pretreatment (clearing treatment) for increasing the light-transmitting property of tissue has been performed with use of a clearing reagent in recent years. Various clearing reagents and pretreatment methods have thus been developed.

For example, Non Patent Literatures 1 and 2 each disclose a clearing treatment technique involving use of benzylbenzoate/benzylalcohol (BABB method). The BABB method is a classic tissue clearing method involving use of an organic solvent, and has been applied as a method for preparing a cleared sample to be observed through a light-sheet macrozoom microscope.

Non Patent Literature 3 discloses a technique (SeeDB method) of adjusting the refractive index with use of fructose. The SeeDB method is primarily intended to minimize a change caused to biological tissue during the treatment, and thus the biological tissue substantially completely maintains the molecular-level structure, membrane structure, axon shape, and the like. The SeeDB method, in a case where it uses a two-photon microscope and an optimized lens, allows observation at a level of the whole brain.

Non Patent Literature 4 and Patent Literature 1 each disclose a technique (Scale method) that uses a water-soluble reagent to successfully minimize quenching of fluorescence signals. This technique is also primarily intended to minimize a change caused to biological tissue during the treatment, and is mainly intended for use in axon observation in neuroscience, detection of an amyloid plaque in tissue affected by Alzheimer's disease, and the like.

Non Patent Literature 5 discloses a clearing technique (CLARITY method) based on a physicochemical method involving use of an electrophoresis apparatus. The CLARITY method uses an electrophoresis apparatus to physicochemically treat brain tissue packed with use of an acrylamide polymer for removal of lipid components to make the brain tissue transparent. The CLARITY method allows high-level clearing in approximately two weeks in a state where the molecular-level structure of tissue is maintained. The CLARITY method is applicable to both (i) fluorescent protein labeling and (ii) immunostaining.

Non-patent Literature 6 discloses clearing techniques (PACT method, PARS method) which, as a way of improvement from the difficult physicochemical method involving use of an electrophoresis apparatus in the CLARITY method, involve perfusion with use of an SDS (detergent) solution which is used in the CLARITY method.

Non-patent Literature 7 discloses a clearing technique (SWITCH method) which, as a way of improvement from the difficult physicochemical method involving use of an electrophoresis apparatus in the CLARITY method, involves high-temperature treatment of an SDS (detergent) solution which is used in the CLARITY method.

CITATION LIST

Patent Literature

[Patent Literature 1]
International Publication No. WO2012/161143

Non-Patent Literatures

[Non-patent Literature 1]
Hans-Ulrich Dodt et al., "Ultramicroscopy: three-dimensional visualization of neuronal networks in the whole mouse brain", Nature Methods, vol. 4, No. 4: 331-336 (2007)

[Non-patent Literature 2]
Klaus Becker et al., "Chemical Clearing and Dehydration of GFP Expressing Mouse Brains", PLoS ONE, vol. 7, issue 3: e33916 (2012)

[Non-patent Literature 3]
Meng-Tsen Ke et al., "SeeDB: a simple and morphology-preserving optical clearing agent for neuronal circuit reconstruction", advance online publication (published online 23 Jun. 2013)

[Non-patent Literature 4]
Hiroshi Hama et al., "Scale: a chemical approach for fluorescence imaging and reconstruction of transparent mouse brain", Nature Neuroscience, vol. 14, No. 11: 1481-1490 (2011)

[Non-patent Literature 5]
Kwanghun Chung et al., "Structural and molecular interrogation of intact biological systems", Nature, vol. 497: 332-339 (2013)

[Non-patent Literature 6]
Bin Yang et al., "Single-Cell Phenotyping within Transparent Intact Tissue through Whole-Body Clearing", Cell, vol. 158: 945-958 (2014)

[Non-patent Literature 7]
Evan Murray et al., "Simple, Scalable Proteomic Imaging for High-Dimensional Profiling of Intact Systems", Cell, vol. 163: 1500-1514 (2015)

SUMMARY OF INVENTION

Technical Problem

However, according to the BABB method described in each of Non Patent Literatures 1 and 2, disappearance of a fluorescent protein occurs significantly due to a dehydration process and an organic solvent treatment, and signal detection thus becomes impossible within a short time. In addition, organic solvents in general have a safety concern.

The SeeDB method, described in Non Patent Literature 3, allows observation at a whole-brain level, but requires several days for scanning. Further, the SeeDB method is assumed to be applied to a two-photon microscope, and the transparency of tissue treated (adult brain in particular) is thus not high enough for observation through a microscope of a light-sheet system.

The Scale method described in Non-patent Literature 4 is assumed to be applied to a confocal microscope and a two-photon microscope, and the transparency of tissue treated (adult brain in particular) is thus not high enough for observation through a microscope of a light-sheet system.

The CLARITY method, described in Non Patent Literature 5, and the PACT method and the PARS method, described in Non-patent Literature 6, each involve a complicated process and require a dedicated device. The CLARITY method, the PACT method, and the PARS method are thus not suited for multiple samples.

The SWITCH method described in Non-patent Literature requires a high-temperature treatment with use of a detergent, and disappearance of a fluorescent protein is thus significant.

The present invention has been accomplished to solve the above problems. It is an object of the present invention to provide a clearing technique which uses a simple process and is suitable for use in high-throughput and low-magnification imaging.

Solution to Problem

In order to solve the above problems, the inventors of the present invention conducted a large-scale screening on the basis of various unique viewpoints. As a result, the inventors of the present invention found a plurality of compounds which are capable of making a biological material transparent. Thus, the inventors of the present invention completed the present invention.

That is, a composition in accordance with the present invention is a composition for preparing a biological material having an excellent light-transmitting property, the composition being a solution containing at least one of: (A) a compound having a high delipidation ability; (B) a compound exhibiting a decoloring activity higher than that of N,N,N',N'-tetrakis(2-hydroxypropyl)ethylenediamine; (C) a combination of EDTA, an acid, and a base; (D) a compound which is soluble at a concentration of 60 wt % or more in water and which allows an aqueous solution, in which the compound (D) is contained at a concentration that is at least one value within a range of 60 wt % to 80 wt %, to have a refractive index of 1.47 to 1.50; and (E) a compound exhibiting a swelling activity higher than that of urea.

A method in accordance with the present invention is a method for preparing a biological material having an excellent light-transmitting property, the method comprising the step of: permeating into a biological material a solution containing at least one of the above-described (A) to (E).

A biological material having an excellent light-transmitting property in accordance with the present invention is a biological material which has been permeated with a solution containing at least one of the above-described (A) to (E).

Advantageous Effects of Invention

The present invention is a technique based on a chemical treatment, and does not require employment of specialized equipment and a complicated manipulation. Further, the present invention uses a simple process to make it possible to make a biological material transparent at a level high enough for a high-throughput analysis of multiple samples.

BRIEF DESCRIPTION OF DRAWINGS

FIG. 3 is a view showing clearing of mouse hemispheres and efficiency of delipidation of the mouse hemispheres in an Example of the present invention.

FIG. 9 is a view showing clearing of a mouse kidney and efficiency of delipidation of the mouse kidney in a case of using 10 wt % #0414+each 10 wt % chemical in an Example of the present invention.

FIG. 11 is a view showing clearing of a mouse whole brain with use of 10 wt % #0414+10 wt % TRITON™ X-100 (2-[4-(2,4,4-trimethylpentan-2-yl)phenoxy]ethanol) in an Example of the present invention.

FIG. 12 is a view showing efficiency of decoloring of a mouse spleen in an Example of the present invention.

FIG. 13 is a view showing clearing of a mouse femur and fluorescence quenching of GFP in a case of using each EDTA cocktail in an Example of the present invention.

FIG. 14 is a view showing a solubility test of a hydroxyapatite suspension in an Example of the present invention.

FIG. 15 is a view showing pH-dependency of solubilization of a hydroxyapatite suspension with use of each EDTA+#0414 cocktail in an Example of the present invention.

FIG. 16 is a view showing temperature-dependency and EDTA concentration-dependency of solubilization of a hydroxyapatite suspension with use of each EDTA+#0414 cocktail in an Example of the present invention.

FIG. 18 is a view showing clearing of a mouse kidney in a case of using each kind of refractive index adjusting agent in an Example of the present invention.

FIG. 19 is a view showing clearing of a mouse lung caused in a case of using each kind of refractive index adjusting agent in an Example of the present invention.

FIG. 20 is a view showing top compounds in swelling screening performed with use of gelatin in an Example of the present invention.

FIG. 21 is a view showing swelling of a brain which has been subjected to delipidation with use of a reagent #1352 having a swelling activity in an Example of the present invention.

FIG. 22 is a view showing a swollen brain which has been made transparent with use of a #0640+#1352 mixed solution in an Example of the present invention.

FIG. 23 is a view showing clearing of tissue including human brain white matter and a mouse liver in an Example of the present invention.

FIG. 30 is a view of Table 1 of the present invention.

FIG. 32 is a view of Table 3 of the present invention.

DESCRIPTION OF EMBODIMENTS

Figure 1:
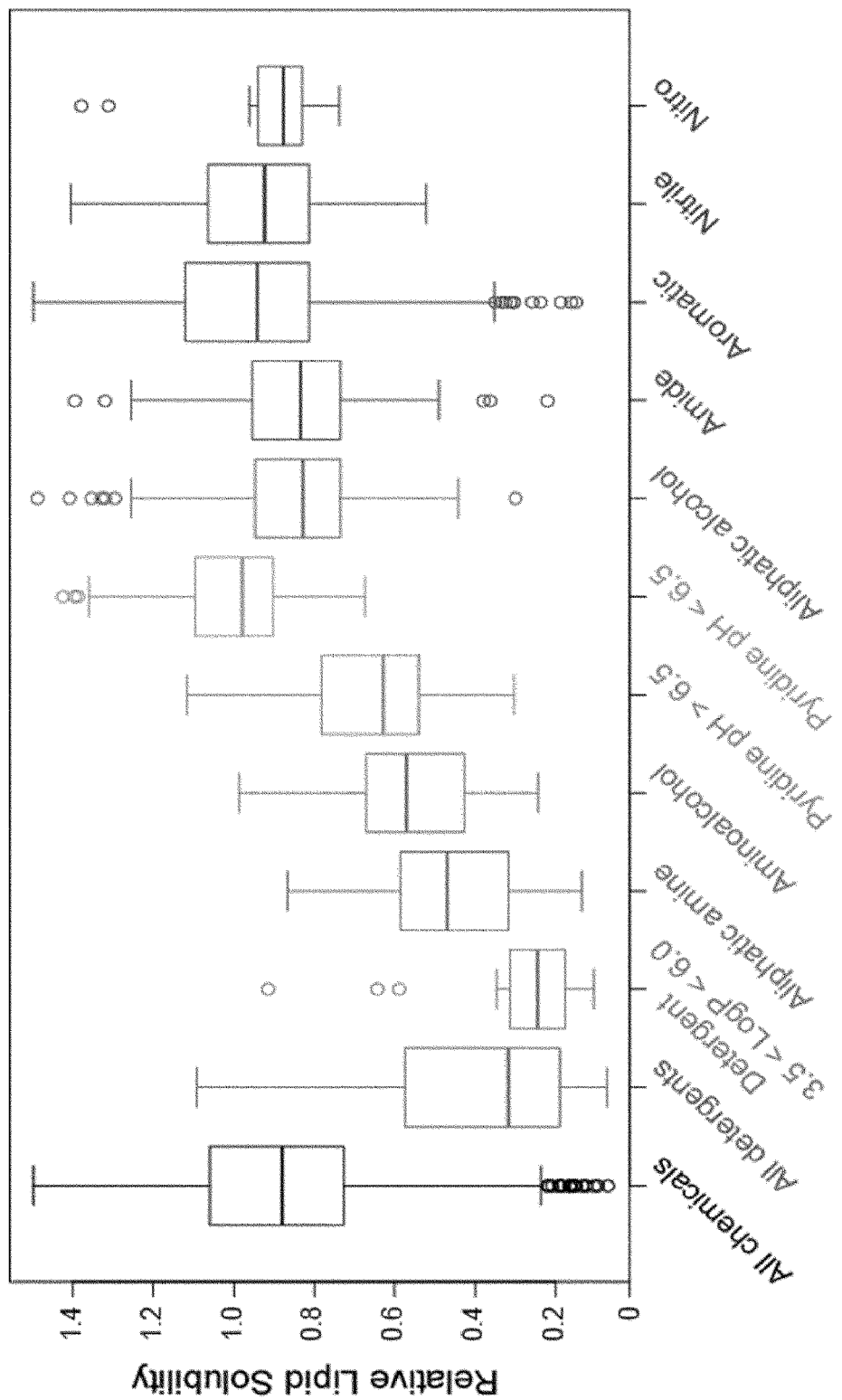
FIG. 1 is a view showing a correlation between delipidation activity and compound category in an Example of the present invention.

The following description will discuss an embodiment of the present invention in detail.

[1. Composition]

The present invention provides a composition for preparing a biological material having an excellent light-transmitting property. A composition in accordance with the present invention is characterized by being a solution containing at least one (one, two, three, four, or five) of (A) to (E), each of which will be described later.

The term "light-transmitting property" as used in the present invention refers to (i) the proportion of transmitted light with respect to incident light or (ii) what proportion of fluorescence generated by excitation light irradiation passes through and how low scattering of the fluorescence light is. The expression "having an excellent light-transmitting property" means, as an example, that the proportion of outgoing light from an observation target (that is, transmitted light) is large with respect to light incident on the observation target. The light-transmitting property can be expressed as, for example, a percentage such that regarding the proportion of transmitted light with respect to incident light, (i) a substance that blocks light (for example, a black and thick plastic, a metal, or the like) has 0% and (ii) a transparent liquid such as water has 100%. For a biological material in accordance with one embodiment having an excellent light-transmitting property, the proportion of transmitted light with respect to incident light is 40% or more, preferably 50% or more, 60% or more, 70% or more, 80% or more, 90% or more, 95% or more, 98% or more, or 99% or more in terms of light transmittance as measured with use of a spectrophotometer.

A biological material to which the present invention is to be applied is not limited to any particular kind. Preferably, the biological material is a material derived from a plant or an animal, more preferably a material derived from an animal such as one selected from fish, amphibians, reptiles, birds, and mammals, particularly preferably a material derived from a mammal. The mammal is not limited to any particular kind and includes: laboratory animals such as mice, rats, rabbits, guinea pigs, and primates except for humans (such as marmosets); pet animals such as dogs and cats; farm animals such as cows and horses; and humans.

Alternatively, the biological material may be an individual itself (except for a living human individual). Further alternatively, the biological material may be an organ, a tissue, a body fluid (for example, blood, saliva, blood serum, blood plasma, urine, synovial fluid, or spinal fluid), or a cell taken from an individual of a multicellular organism. The organism may be an adult or a fetus. The composition in accordance with the present invention has excellent ability to make a subject transparent; therefore, even if the biological material is a tissue or organ (for example, the whole of or part of the bones, brain, heart, lungs, liver, spleen, or kidneys) derived from a multicellular animal or an individual itself (for example, an embryo or an adult) of a multicellular animal which is not a human, the biological material can be subjected to a clearing treatment. Further, the biological material may be either of (i) a material fixed with use of paraformaldehyde or the like and (ii) a non-fixed material.

Specific examples of the biological material may be: a biological tissue having a fluorescent chemical substance injected therein; a biological tissue stained with a fluorescent chemical substance; a biological tissue having a fluorescent protein-expressed cell transplanted therein; and a biological tissue taken from a genetically-modified animal in which a fluorescent protein is expressed.

The present invention can significantly improve the light-transmitting property of a biological material, and thus allows high-throughput imaging. Specifically, the present invention:

minimizes quenching of signals of a fluorescent protein or fluorescent substance;

allows multiple samples (several tens to several hundreds of samples) to be treated simultaneously in parallel;

makes a subject so highly transparent that the subject can be observed under a light-sheet microscope in combination;

minimizes the influence on the structuring of a tissue region; and effectively allows even a large sample (e.g., an adult) made up of various types of tissue to be made transparent.

Further, a clearing treatment that uses the composition in accordance with the present invention is reversible to a certain extent. Specifically, simply immersing, in an equilibrated salt solution, a biological material that has been subjected to the clearing treatment releases the biological material from a clearing state, so that the non-transparent biological material can be preserved or used in, for example, an immunohistochemical assay or biochemical assay. Specific examples of the balanced salt solution include a balanced salt solution (for example, a PBS or HBSS) buffered with a phosphate; a balanced salt solution (TBS) buffered with tris hydrochloride; a population cerebrospinal fluid (ACSF); and a cell-culture basal medium such as MEM, DMEM, and Ham's F-12. The antigenicity of a protein or the like remains unchanged (preserved) before and after the clearing treatment. This makes it possible to perform analyses with use of a normal tissue-staining technique or immunostaining technique.

((A) Compound Having Delipidation Removal Ability)

A compound (A) which may be contained in the composition in accordance with the present invention is a compound having a delipidation ability. In an example, the compound (A) has a high delipidation ability.

In one embodiment, the compound (A) is such a compound that a mixed solution containing the compound has an OD600 of not more than 0.336 as measured by a method described in the Examples. In another embodiment, the compound (A) is at least one of, for example, a polyether, an anionic detergent, a cationic detergent, an amphoteric detergent, an amine, an aminoalcohol, a polyhydric alcohol, a detergent-like aromatic ether, and a pyridine. From the viewpoint of permeability of the compound (A) with respect to tissue, an amine and a polyalcohol are preferable, and an amine is more preferable.

The amine may be any one of primary amine, secondary amine, tertiary amine, and quaternary amine. The number of amine groups contained in the compound may be one, two, three, four, or more. The amine may have a linear, branched, or cyclic hydrocarbon moiety. The amine may have a saturated or unsaturated hydrocarbon moiety. The amine may have an aromatic ring such as a benzene ring. The number of carbon atoms constituting a hydrocarbon moiety of the amine is not particularly limited, and may be, for example, 1 to 20, 1 to 15, 1 to 10, or 2 to 8.

More specific examples of the compound (A) include compounds shown in FIG. 30/Table. 1 and analogs thereof. In one example, #0070 (1,3-bis(aminomethyl)cyclohexane) in FIG. 30/Table 1 and an analog thereof are preferable. Examples of the analog of #0070 include bis(aminoalkyl) cycloalkyl. The number of carbon atoms constituting an alkyl in an aminoalkyl group is not particularly limited, and, for example, the number may be 1 to 8, and is 1 in a preferable example. The number of carbon atoms constituting an alkyl in a cycloalkyl moiety is not particularly limited, and, for example, the number may be 3 to 8, and is 6 in a preferable example. The two aminoalkyl groups may be bonded at any position, for example, at "1,2-", "1,3-", or "1,4-". Among the compounds shown in FIG. 30/Table. 1, and the analogs thereof, #0070 (1,3-bis(aminomethyl)cyclohexane) in FIG. 30/Table. 1 is preferable from the viewpoint of inexpensiveness and less odor.

Further, the compound (A) may be of a single kind or of two or more kinds. In one embodiment, the compound (A) may be a combination of two or more kinds of a polyether, an anionic detergent, a cationic detergent, an amphoteric detergent, an amine, an aminoalcohol, a polyhydric alcohol, a detergent-like aromatic ether, and a pyridine. In one example, it may be preferable to combine an amine and a detergent. Examples of a preferable combination of an amine and a detergent include a combination of #0070 and #0631 and a combination of #0070 and SDS. In particular, the combination of #0070 and #0631 is more preferable.

In a case where the biological material contains a fluorescent protein, it is preferable to use a compound having a pH of 5 to 12, preferably 7 to 11. In particular, from the viewpoint of transparency, #0389 and #0414 are preferable, and #0414 is more preferable. #0414 may be used in combination with another compound. Examples of a preferable combination include a combination of #0414 and TRITON™ X-100 (2-[4-(2,4,4-trimethylpentan-2-yl)phenoxy]ethanol), a combination of #0414 and TWEEN©-40 (Polyoxyethylenesorbitan monopalmitate), a combination of #0414 and #1051, a combination of #0414 and #0694, and a combination of #0414 and sucrose. In particular, the combination of #0414 and TRITON™ X-100 (2-[4-(2,4,4-trimethylpentan-2-yl)phenoxy]ethanol) is more preferable.

The concentration of the compound (A) in the composition is not particularly limited, and, for example, the concentration (in a case where the composition contains two or more compounds, the total concentration of these compounds) is preferably 5 wt % to 60 wt %, more preferably 10 wt % to 40 wt %, further more preferably 15 wt % to 30 wt %. In one example, in a case where an amine and a detergent are combined, the concentration of the amine may be 10 wt % to 20 wt % and the concentration of the detergent may be 5 wt % to 10 wt %.

((B) Compound Having Biochrome Decoloring Ability)

A compound (B) which may be contained in the composition in accordance with the present invention is a compound having a biochrome decoloring ability. In one example, the compound (B) has a high biochrome decoloring ability.

In one embodiment, the compound (B) is a compound exhibiting a decoloring activity higher than that of an aminoalcohol (N,N,N',N'-tetrakis(2-hydroxypropyl)ethylenediamine). The decoloring activity can be measured, for example, by a method described in the Examples.

In another embodiment, the compound (B) is at least one of, for example, phosphine, alkyl imidazole, a detergent, an amine, a pyridine, an aminoalcohol, an alcohol, benzylamide, and pyrazolone.

Figure 31:
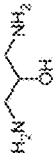
FIG. 31 is a view of Table 2 of the present invention.

More specific examples of the compound (B) include compounds shown in FIG. 31/Table. 2 and analogs thereof. In one example, the compound (B) is preferably one which allows fluorescence of a fluorescent protein to be retained, and examples of such a compound include #0441, #0470, #0484, #0635, #0651, #0938, and #1283 shown in FIG. 31/Table. 2 and analogs thereof.

From the viewpoint of allowing retention of fluorescence of a fluorescent protein and exhibiting a high decoloring activity, #0651, #0938, and analogs thereof are preferable, and #0938 and an analog thereof are more preferable.

Examples of the analog of #0938 include a compound encompassed in alkyl imidazoles. The alkyl group may be linear, branched, or cyclic. The alkyl group may be saturated or unsaturated. The number of carbon atoms constituting the alkyl group is not particularly limited, and may be, for example, 1 to 20, 1 to 15, 1 to 10, 1 to 8, 1 to 6, 1 to 5, 1 to 4, 1 to 3, or 1 to 2. The position at which the alkyl group is bonded is not particularly limited, but is preferably the first position (1-alkyl imidazole). From the viewpoint of inexpensiveness, 1-methylimidazole is preferable.

The compound (B) may be of a single kind or of two or more kinds.

The concentration of the compound (B) in the composition is not particularly limited, and, for example, the concentration (in a case where the composition contains two or more compounds, the total concentration of these compounds) is preferably 5 wt % to 40 wt %, more preferably 5 wt % to 30 wt %, and further more preferably 10 wt % to 20 wt %.

In one example, the compound (B) has high affinity for heme, and allows detaching heme from hemoglobin without destroying a protein.

((C) Compound Having Decalcification Ability)

A compound (C) which may be contained in the composition in accordance with the present invention is a compound having a decalcification ability. In one example, the compound (C) has a high decalcification ability.

In one embodiment, the compound (C) is a combination of EDTA (ethylenediaminetetraacetic acid), an acid, and a base. Combining the EDTA, the acid, and the base enables efficient decalcification. In one example, quenching of signals of a fluorescent protein is minimized.

Examples of the acid include halogenated monocarboxylic acid, hydroxymonocarboxylic acid, aliphatic monocarboxylic acid, alkyl amino monocarboxylic acid, acetylamino monocarboxylic acid, other monocarboxylic acids, dicarboxylic acid, malic acid, thiodicarboxylic acid, tartaric acid, malonic acid, other dicarboxylic acids, polyvalent carboxylic acid, sugars, tetrafluoroborate, phosphoric acids, sulfonic acids, hydrocarbon, acid salts of amines, and acid salts of aromatic amines. In one example, the acid preferably has a pH of 2.0 or more from the viewpoint of tissue damage.

More specific examples of the acid include compounds shown in Table. 4. Examples of preferable acids among the compounds shown in Table. 4 include a compound having a Score value of not more than 0.9 in the Examples. Examples of more preferable acids among the compounds shown in Table. 4 include #1165 and #1300. The acid may be of a single kind or of two or more kinds.

In one example, the base is preferably a compound having a delipidation removal ability. Specific examples of the base include bases (amine, aminoalcohol, and pyridine) having the delipidation removal ability described in (A) above. In particular, aminoalcohol is preferable, and #0414 and an analog thereof are more preferable. Examples of the analog of #0414 include N-alkyl dialcoholamine. The alkyl group of the N-alkyl dialcoholamine may be linear, branched, or cyclic. The alkyl group of the N-alkyl dialcoholamine may be saturated or unsaturated. The number of carbon atoms constituting the alkyl group of the N-alkyl dialcoholamine is not particularly limited, and, for example, the number may be 1 to 8, and is 4 in a preferable example. The two alcohol moieties may each have any number of carbon atoms, and the number may be the same or different between the two alcohol moieties. For example, the number may be 1 to 8, and is two in a preferred example. The base may be of a single kind or of two or more kinds.

In another example, the base is preferably an imidazole analog, more preferably #1352. Other preferable examples of the base include a heterocyclic amine such as #1278 (4-methylmorpholine), and #0370 (2-amino-6-methylpyridine).

A solution containing (C) has a pH which is preferably 6 to 11, more preferably 7 to 9, and further more preferably approximately 8.

The concentration of the EDTA in the solution containing (C) is not particularly limited, and is preferably 5 wt % to 25 wt %, more preferably 7.5 wt % to 20 wt %, and further more preferably approximately 10 wt %. The concentration of the acid in the solution containing (C) is not particularly limited, and is preferably 5 wt % to 25 wt %, more preferably 7.5 wt % to 20 wt %, and further more preferably approximately 10 wt %. The concentration of the base in the solution containing (C) is not particularly limited, provided that the solution has a target pH level. In one example of a method for preparing the solution containing (C), the base is added to a solution which contains the EDTA and the acid.

((D) Compound Having Refractive Index Adjusting Ability)

A compound (D) which may be contained in the composition in accordance with the present invention is a compound having a refractive index adjusting ability. In one example, the compound (D) has a high refractive index adjusting ability.

In one embodiment, the compound (D) is a compound which is soluble at a concentration of 60 wt % or more in water and which allows an aqueous solution, in which the compound (D) is contained at a concentration that is at least one value within a range of 60 wt % to 80 wt %, to have a refractive index of 1.47 to 1.50.

In another embodiment, the compound (D) is at least one of, for example, a benzylamine, a pyridine, an amine, a benzylaminoalcohol, hydrazine, and thiourea.

More specific examples of the compound (D) include compounds shown in FIG. 32/Table. 3 and analogs thereof. From the viewpoint of preventing shrinkage, the compound (D) is preferably a salt-free compound. Examples of such a compound include #0370, #0389, #0587, #0609, #0640, #1102, and #1283 shown in FIG. 32/Table. 3 and analogs thereof. Among these compounds, from the viewpoint of achieving a higher transparency, #0587, #0640, #1102, #1283 and analogs thereof are preferable, and #0587 and an analog thereof is more preferable.

Among the compounds shown in FIG. 32/Table. 3 and analogs thereof, #0640, #0450, #1283, #0864, #1052, #0788, #0389 and analogs thereof are preferable from the viewpoint of allowing retention of fluorescence of a fluorescent protein.

Further, from the viewpoint of achieving a higher transparency, a combination of #0640 and #1283, a combination of #0640 and nicotinamide (#0855), and a combination of Histodenz and #1283 are also preferable.

The compound (D) may be of a single kind or of two or more kinds.

In one example, the concentration of the compound (D) in the composition is preferably a concentration which allows the composition to have a refractive index of 1.47 to 1.53. Specifically, for example, the concentration (in a case where the composition contains two or more compounds, the total concentration of these compounds) is preferably 50 wt % to 90 wt %, more preferably 60 wt % to 85 wt %, and further more preferably 70 wt % to 80 wt %. With respect to the specific combinations described above, for example, it is preferable that the concentration of the former one of each combination be 40 wt % to 50 wt %, and the concentration of the latter one of the each combination be 25 wt % to 35 wt %.

((E) Compound Having Tissue Swelling Ability)

A compound (E) which may be contained in the composition in accordance with the present invention is a compound having a tissue swelling ability. In one example, the compound (E) has a high tissue swelling ability.

In one embodiment, the compound (E) is a compound exhibiting a swelling activity higher than that of urea. The swelling activity may be measured, for example, by a method described in the Examples.

Examples of the compound (E) include compounds shown in FIG. 20, imidazole derivatives, and antipyrine analogs.

The compound (E) may be of a single kind or of two or more kinds.

The concentration of the compound (E) in the composition is not particularly limited, and, for example, the concentration (in a case where the composition contains two or more compounds, the total concentration of these compounds) is preferably 5 wt % to 40 wt %, more preferably 5 wt % to 30 wt %, and more preferably 5 wt % to 25 wt %.

In one example, the compound (B) is capable of swelling a biological material so as to increase the volume of the biological material by 4 times to 10 times, while maintaining the shape of the biological material.

(Combination)

Two or more of (A) to (E) may be contained in a single composition.

In one example, the composition preferably contains at least one of (A) and (E) as an essential component. In a case where a biological material contains plenty of blood or a biochrome such as myoglobin, the composition preferably contains (B). In a case where a biological material contains bone tissue, the composition preferably contains (C).

(Solvent)

A solvent for use in the composition in accordance with the present invention is not limited to any particular kind, as long as the solvent allows the above-described active ingredients to be dissolved therein. Preferably, water is used as a main solvent; particularly preferably, only water is used as the solvent. Note that, in the present invention, what is meant by the expression "water is used as a main solvent" is that the volumetric percentage of water with respect to all solvents used is larger than that of any other solvent, and preferably that water is used in an amount that accounts for more than 50% and not more than 100% of the total volume of all solvents used. The composition in accordance with the present invention, in a case where the composition is prepared with use of water as a main solvent, is referred to as a "reagent in the form of an aqueous solution".

In the case where water is used as a main solvent, dimethyl sulfoxide (DMSO) may be mixed with the water for application to a fixed sample, for example. It is expected that, for example, use of a mixture of DMSO and water to a fixed sample provides effects such as (i) improvement in permeability of the reagent with respect to a biological material and (ii) facilitation of a clearing treatment with respect to a tissue having a keratin surface.

Main advantages of the use of water as the solvent are as follows:

1) The active ingredients of the composition in accordance with the present invention are excellent in solubility in water; therefore, the use of water as the solvent makes it possible to (i) inexpensively prepare the composition in accordance with the present invention and (ii) easily prepare the composition in accordance with the present invention.
2) Compared with a case where an organic solvent is used as a main solvent, the use of water as the solvent does not involve dehydration of a biological material when the biological material is subjected to a clearing treatment; therefore, the use of water as the solvent can prevent the problem of shrinkage of a biological material.
3) Compared with a case where an organic solvent is used as a main solvent, the use of water as the solvent significantly reduces the possibility of damaging a fluorescent protein; this makes it possible to observe, with use of a fluorescent protein, a biological material having been subjected to a clearing treatment.
4) The use of water as the solvent makes it possible to apply the composition in accordance with the present invention not only to a clearing treatment on a fixed material but also to a clearing treatment on a living material.
5) The use of water as the solvent makes a clearing treatment reversible, that is, the use of water as the solvent can as necessary bring a biological sample having been subjected to a clearing treatment back to a state that it had before the clearing treatment.
6) Compared with a case where an organic solvent is used as a main solvent, the use of water as the solvent enhances safety in handling of the composition in accordance with the present invention.

The composition in accordance with the present invention may be a buffer solution that can maintain a pH suitable for a biological material to be subjected to a clearing treatment. Further, the composition in accordance with the present invention may have an osmotic pressure adjusted to such a degree that no deformation is caused of a biological material to be subjected to a clearing treatment and that the active ingredients sufficiently penetrate into the biological material.

(Other Optional Components)

A solution as the composition in accordance with the present invention may contain an optional component as necessary. Examples of the optional component include a pH adjusting agent, an osmotic pressure controlling agent, and the like.

[2. Method]

The present invention provides a method for preparing a biological material having an excellent light-transmitting property. A method in accordance with the present invention is characterized by including the step of: permeating (permeation step) into a biological material a solution containing at least one (one, two, three, four, or five) of the above-described (A) to (E). The solution is as described above.

In one embodiment, the method in accordance with the present invention may include the steps of: permeating (first permeation step) into a biological material a solution (first solution) containing at least one of (A) to (E); and permeating (second permeation step) into the biological material a solution (second solution) containing at least another one of (A) to (E), and may further include at least one (one, two, three, four, or five) of the steps of: permeating (third permeation step) into the biological material a solution (third solution) containing at least still another one of (A) to (E); permeating (fourth permeation step) into the biological material a solution (fourth solution) containing at least still another one of (A) to (E); and permeating (fifth permeation step) into the biological material a solution (fifth solution) containing at least still another one of (A) to (E).

(Permeation Step)

In the permeation step, at least one of: delipidation with use of the compound (A); decoloring with use of the compound (B); decalcification with use of the compound (C); refractive index adjustment with use of the compound (D); and swelling with use of the compound (E) is performed. That is, the method in accordance with the present invention includes at least one (one, two, three, four, or five) of a delipidation step with use of the compound (A), a decoloring step with use of the compound (B), a decalcification step with use of the compound (C), a refractive index adjustment step with use of the compound (D), and a swelling step with use of the compound (E). In a case where the method includes a plurality of steps, the steps may be carried out separately, or two or more of the steps may be carried out simultaneously.

A biological material which has been subjected to the delipidation step exhibits an excellent light-transmitting property due to removal of a light scattering substance (mainly lipids) in the biological material. Accordingly, the delipidation step is particularly effective for a case in which a lipid-rich biological material (e.g., a lipid-rich organ or tissue) is made transparent. The delipidation step may be performed, for example, at 25° C. to 45° C. for approximately 1 day to 10 days.

A biological material which has been subjected to the decoloring step exhibits an excellent light-transmitting property due to decoloring of biochromes (mainly hemoglobin in blood) in the biological material. Accordingly, the decoloring step is particularly effective for a case in which blood is made transparent and for a case in which a blood-rich biological material (e.g., a blood-rich organ or tissue) is made transparent. The decoloring step may be performed, for example, at 25° C. to 45° C. for approximately 1 day to 5 days.

A biological material which has been subjected to the decalcification step exhibits an excellent light-transmitting property due to decalcification of calcium-rich tissue (bones, teeth, etc.) in the biological material. Accordingly, the decalcification step is particularly effective for a case in which a calcium-rich biological material (e.g., a calcium-rich organ or tissue) is made transparent. The decalcification step may be performed, for example, at 25° C. to 45° C. for approximately 3 days to 10 days.

A biological material which has been subjected to the refractive index adjustment step exhibits an excellent light-transmitting property due to a reduced difference between a refractive index of a liquid component and a refractive index of biomolecule such as a protein. Accordingly, the refractive index adjustment step is effective for any biological material. The refractive index adjustment step may be performed, for example, at 25° C. to 37° C. for approximately 1 day to 4 days.

A biological material which has been subjected to the swelling step is swollen, and accordingly exhibits an excellent light-transmitting property. Further, the biological material is observable with an improved optical resolution. The swelling step therefore is effective for any biological material. The swelling step may be performed, for example, at 10° C. to 35° C. for approximately 1 day to 7 days.

The order in which the steps are carried out is not particularly limited, but in a case where all of the five steps are carried out, the five steps are preferably carried out in the order of (1), (2), and (3) below.

(1) Delipidation step, decoloring step
(2) Decalcification step, swelling step
(3) Refractive index adjustment step In (1), the delipidation step and the decoloring step may be carried out separately or simultaneously. In one example, the compound (A) to be used in the delipidation step and the compound (B) to be used in the decoloring step are partially or entirely identical to each other, and the delipidation step and the decoloring step can thus be carried out simultaneously. Alternatively, the delipidation step and the decoloring step may be carried out simultaneously by using a mixture of the compound (A) and the compound (B). In a case of separately carrying out the delipidation step and the decoloring step, either of the delipidation step and the decoloring step may be carried out first, but it is preferable to carry out the delipidation step first. In (2), the order in which the decalcification step and the swelling step are carried out is not particularly limited, and either one of the decalcification step and the swelling step may be carried out first.

Also in a case where at least one of the five steps is not carried out, it is preferable to carry out the other ones of the five steps in the above-described order.

(Other Optional Steps)

The method in accordance with the present invention may include the step of: washing (washing step) of washing a biological material at given timing. The washing step may be carried out at timing such as, for example, before a permeation step, between permeation steps, and/or after completion of a permeation step. The washing may be carried out with use of PBS, distilled water, or the like. The washing may be carried out, for example, 1 to 5 times per washing step.

In the method in accordance with the present invention, a biological material which has been made transparent may be preserved at given timing, for example, in a room temperature or low temperature environment (cleared sample preservation step). In such a case, in order to prevent drying of the biological material, the biological material is preferably preserved in a state where the biological material is immersed in the solution or an equilibrated salt solution such as PBS.

The method in accordance with the present invention may be combined with a clearing method other than the method in accordance with the present invention. For example, it is possible to carry out the delipidation step and the decoloring step in accordance with the method of the present invention and carry out refractive index adjustment in accordance with a clearing method (e.g., SeeDB method) other than the clearing method of the present invention.

On a biological material having been made transparent, a step of observation (observation step) with use of, for example, an optical microscope is performed. On a biological material to be subjected to the observation step, a visualizing treatment step such as staining or marking may as necessary be performed (i) before the clearing treatment of the present invention or (ii) after the clearing treatment and before the observation step. For example, in a case where the visualizing treatment step involves use of a fluorescent protein, a fluorescent protein gene is introduced into a living biological material before the clearing treatment so that the fluorescent protein will be expressed therein. In a case where the visualizing treatment step is (i) injection of fluorescent chemical (small) molecules (which is not a fluorescent protein) into a biological material or (ii) staining of a biological material with use of fluorescent chemical (small) molecules, the visualizing treatment step is preferably performed before the clearing treatment. However, the visualizing treatment step may be performed after the clearing treatment. Alternatively, the visualizing treatment step may be staining of a biological material with use of a chemical substance which is not fluorescent chemical molecules.

The observation step can be performed with use of any type of optical microscope. For example, the observation step can be performed with use of a light-sheet microscope, a two-photon laser microscope, a confocal microscope, and/or the like. The method in accordance with the present invention is particularly suitably applicable to a high-throughput analysis of multiple samples at a low-magnification.

[3. Kit]

The present invention provides a kit which includes a composition for preparing a biological material having an excellent light-transmitting property.

The term "kit" as used in the present specification refers to a package including a container (for example, a bottle, a plate, a tube, a dish, or the like) containing a particular material (for example, a constituent component). The kit is preferably provided with a manual for use of each material. Various forms of the verb "include" as used in the present specification to describe an aspect of the kit refer to a state in which the material is contained in any of the individual containers constituting the kit. A kit in accordance with the present invention may be a single package containing a plurality of different compositions. The compositions may each be contained in one of a plurality of different containers in a case where the compositions are each in the form of a solution. The kit in accordance with the present invention may include its constituent elements either (i) in a single container as the constituent elements are mixed with each other or (ii) in separate containers. The "manual" may be printed or written on a medium such as paper or an electronic medium such as a magnetic tape, a computer-readable disc or tape, or a CD-ROM. The manual shows a procedure for achieving the purpose of the kit. The kit in accordance with the present invention may further include a container containing a diluent, a solvent, a cleaning fluid, or another reagent. In addition, the kit in accordance with the present invention may include an instrument and a reagent that are necessary to carry out the procedure for achieving the purpose of the kit.

In one example, the kit may include two or more kinds of the above-described composition. For example, in a case of performing the delipidation step and the decoloring step separately, the kit may include a composition containing (A) and a composition containing (B). In one embodiment, the kit includes at least two (two, three, four, or five) of a composition containing (A), a composition containing (B), a composition containing (C), a composition containing (D), and a composition containing (E). In another embodiment, the kit includes at least (i) a composition containing at least two (two, three, four, or five) of (A) to (E) and (ii) a composition containing at least another one (one, two, three, four, or five) of (A) to (E).

The following will provide Examples to more specifically describe embodiments of the present invention. As a matter of course, the present invention is not limited to Examples provided below, and details of the present invention can be realized in various manners. Further, the present invention is not limited to the embodiments described above, and it may be varied in various ways within the scope of the appended claims. Thus, an embodiment based on a proper combination of technical means disclosed in different embodiments is encompassed in the technical scope of the present invention. In addition, the present specification encompasses the contents of the specification and/or drawings of Japanese Patent Application No. 2016-092025, to which the present application claims priority. Furthermore, all of the publications and patents cited in the present specification are incorporated herein by reference in their entirety.

Examples

[1. Search for Clearing Reagent]

An experiment technique was developed for high-throughput evaluation of a library of 1619 water-soluble compounds to identify a good compound in terms of each of the following five parameters that are required in clearing: (A) delipidation ability, (B) biochrome decoloring ability, (C) decalcification ability, (D) refractive index adjusting ability, and (E) tissue swelling ability.

(A. Delipidation Ability)

The library of 1619 water-soluble compounds was screened for compounds having a delipidation ability, with use of an assay method involving solubilization of fixed brain tissue described in Susaki et al., Cell, 157, 726-739, 2014.

Figure 2:
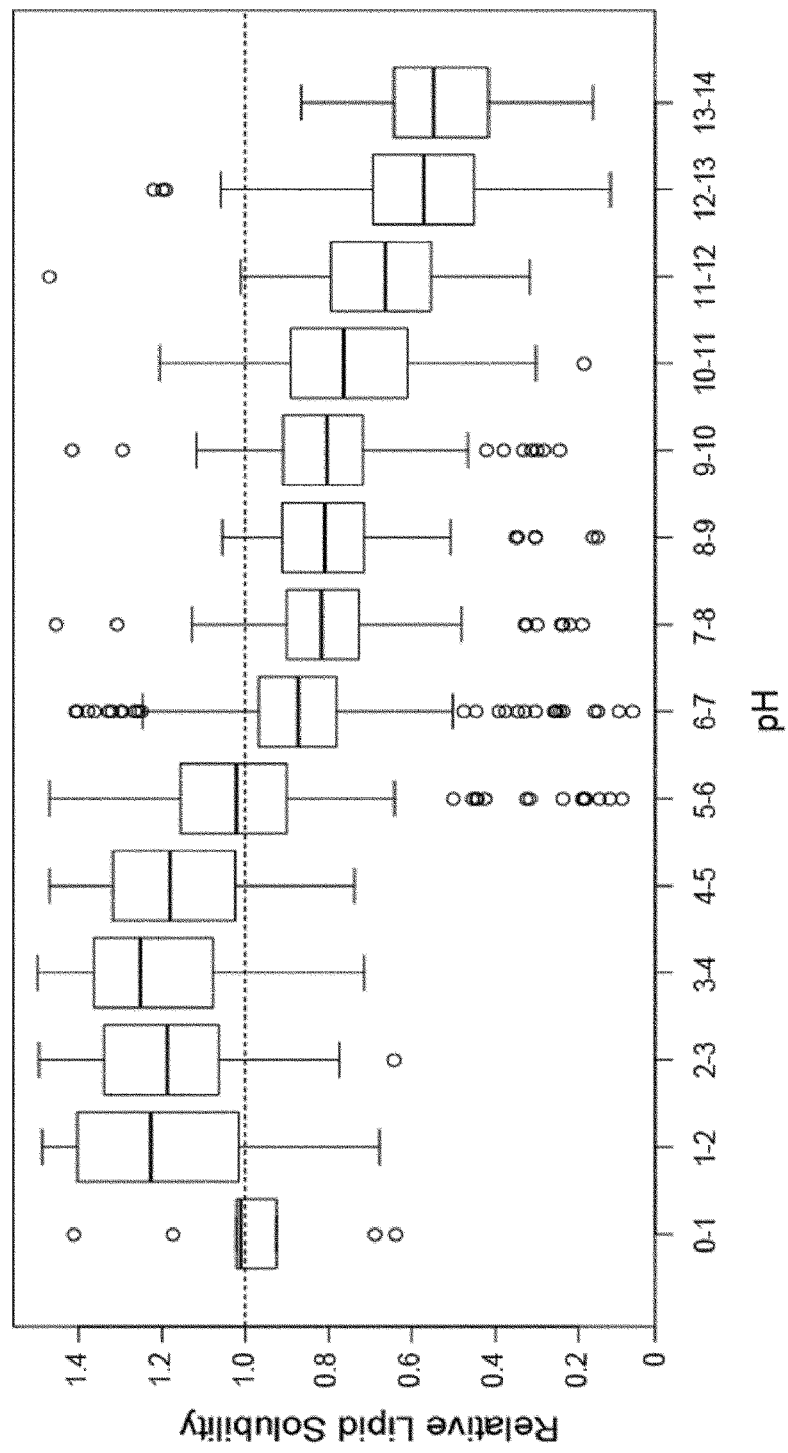
FIG. 2 is a view showing a correlation between delipidation activity and pH in an Example of the present invention.

Specifically, brains taken out of mice were sheared with a utility knife and then were disrupted by ultrasonication. To each of the resultant suspensions, an equal volume of 8% PFA solution was added to perform fixation at 4° C. for 1 hour. The resultant mixture was centrifuged to remove the supernatant, and the fixed brain tissue was washed with PBS for 3 times. PBS was added so as to obtain 2 mL of a fixed brain tissue suspension per brain. The fixed brain tissue suspension was diluted by 3.5 folds. To 20 μL of the resultant suspension, 130 μL of each 10 wt % chemical was added and was shaken at 37° C. overnight. Thus obtained mixed solutions were subjected to absorbance (turbidity) measurement at 600 nm. It is expected that a chemical solution which reduces the turbidity of a fixed brain suspension allows reducing light scattering by solubilizing lipids, which act as a scattering factor, in the brain tissue. Top 50 chemicals contributing to turbidity reduction were categorized by chemical properties, and it was thus revealed that detergents, aminoalcohols, aliphatic amines, and pyridines were effective (FIG. 30/Table. 1 and FIG. 1). Further, the reduction in turbidity of a fixed brain suspension was correlated with the pH of the solution, and the reduction in turbidity was more significant as the basicity of the solution increased (FIG. 2).

Figure 3:
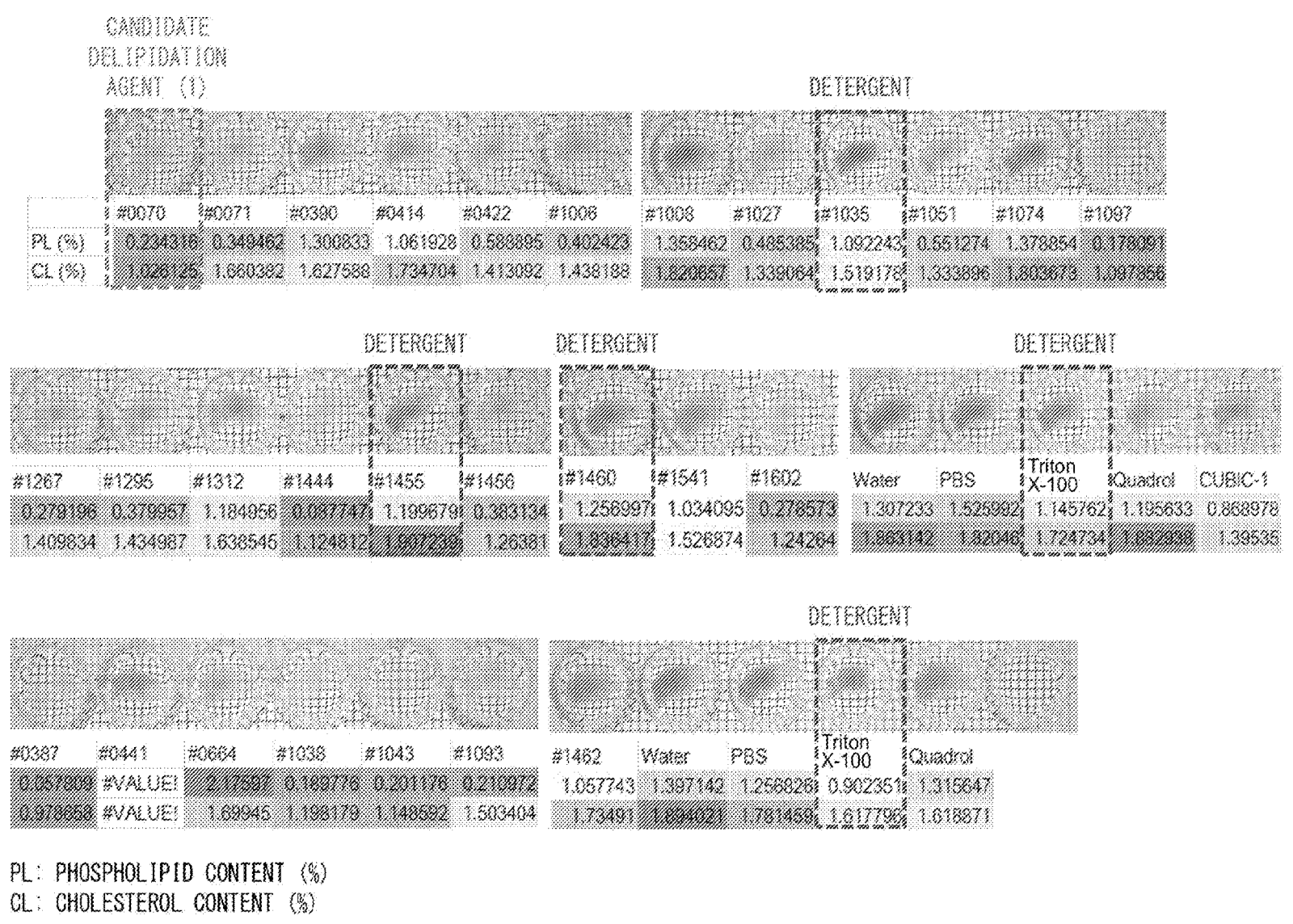
Figure 4:
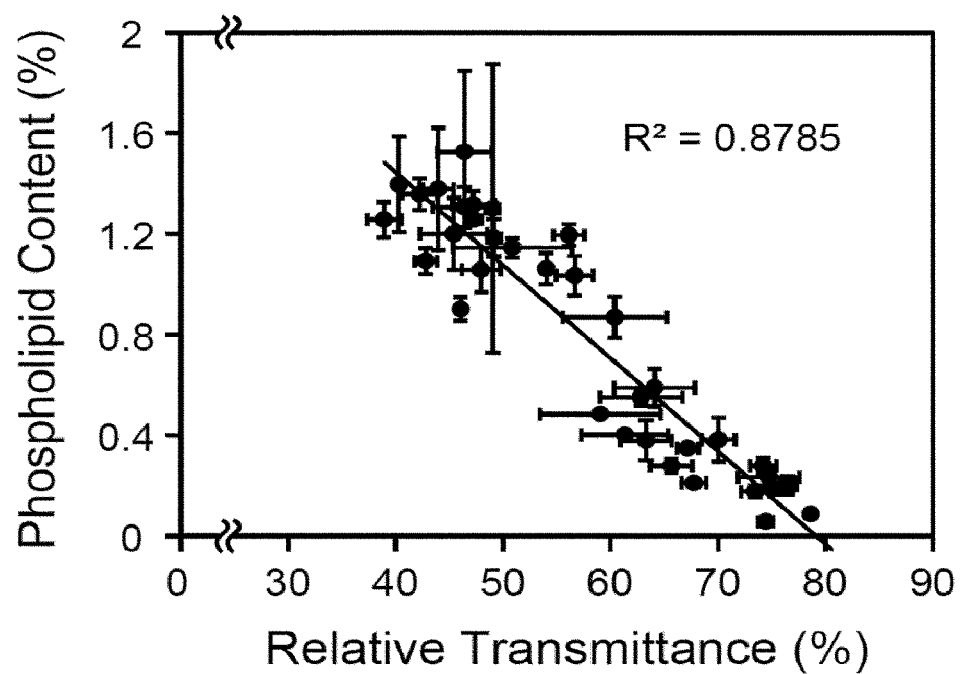
FIG. 4 is a view showing a correlation between transparency and phospholipid content of a mouse hemisphere in an Example of the present invention.

Subsequently, the delipidation efficiency of the series of compounds in mammalian tissue was examined. A mouse hemisphere was treated with use of each 10 wt % chemical solution at 37° C. for 3 days, washed with PBS, and then subjected to refractive index adjustment with CUBIC-2A (22.5 wt % sucrose, 22.5 wt % antipyrine, 25 wt % urea, and 10 wt % triethanolamine). The transmittance of the brain tissue was measured, and then the brain tissue was washed with PBS and was disrupted. The lipid content (phospholipid content and cholesterol content) of the resultant suspension was quantified (FIG. 3), in which a close correlation between a residual phospholipid content and tissue transmittance was observed (FIG. 4). This indicates that the lower the phospholipid content is, the higher the tissue transparency is. This result directly verifies that delipidation contributes to transparency. Importantly, as compared with the detergents typified by #1035, #1455, #1460, and TRITON™ X-100 (2-[4-(2,4,4-trimethylpentan-2-yl)phenoxy]ethanol), higher degrees of delipidation and clearing were observed with basic chemicals such as aminoalcohols and aliphatic amines and with some neutral chemicals such as #1051. It was thus shown that the above basic chemicals and some neutral chemicals were better than the detergents from the viewpoint of permeability with respect to tissue. Among the obtained basic chemicals, #0070 (1,3-bis(aminomethyl)cyclohexane) was selected from the viewpoint of price and odor of a reagent.

Figure 5:
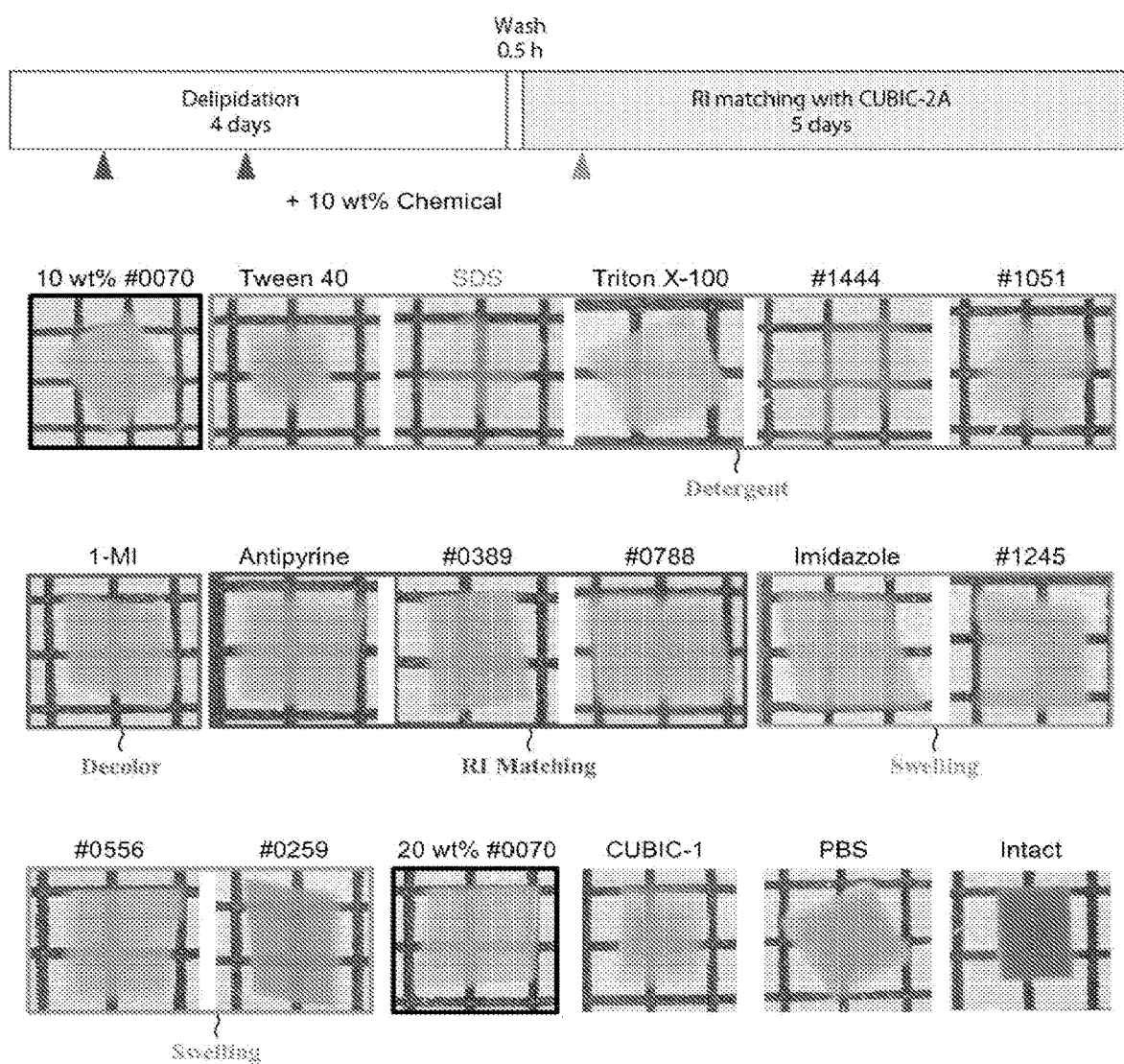
FIG. 5 is a view showing a comparison of clearing of human brain white matter with use of 10 wt % #0070+each 10 wt % chemical in an Example of the present invention.

A study was conducted to identify a combination of #0070 and another chemical which combination would synergistically contribute to delipidation so as to maximize delipidation activity (FIG. 5). A small piece of human brain white matter was treated with use of a cocktail of 10 wt % #0070+each 10 wt % chemical at 37° C. for 4 days. The small piece was washed with PBS and then subjected to refractive index adjustment with CUBIC-2A. It was thus revealed that a combination of #0070 and SDS, which is a detergent, was the best from the viewpoint of allowing high-level clearing without damage to tissue.

Figure 6:
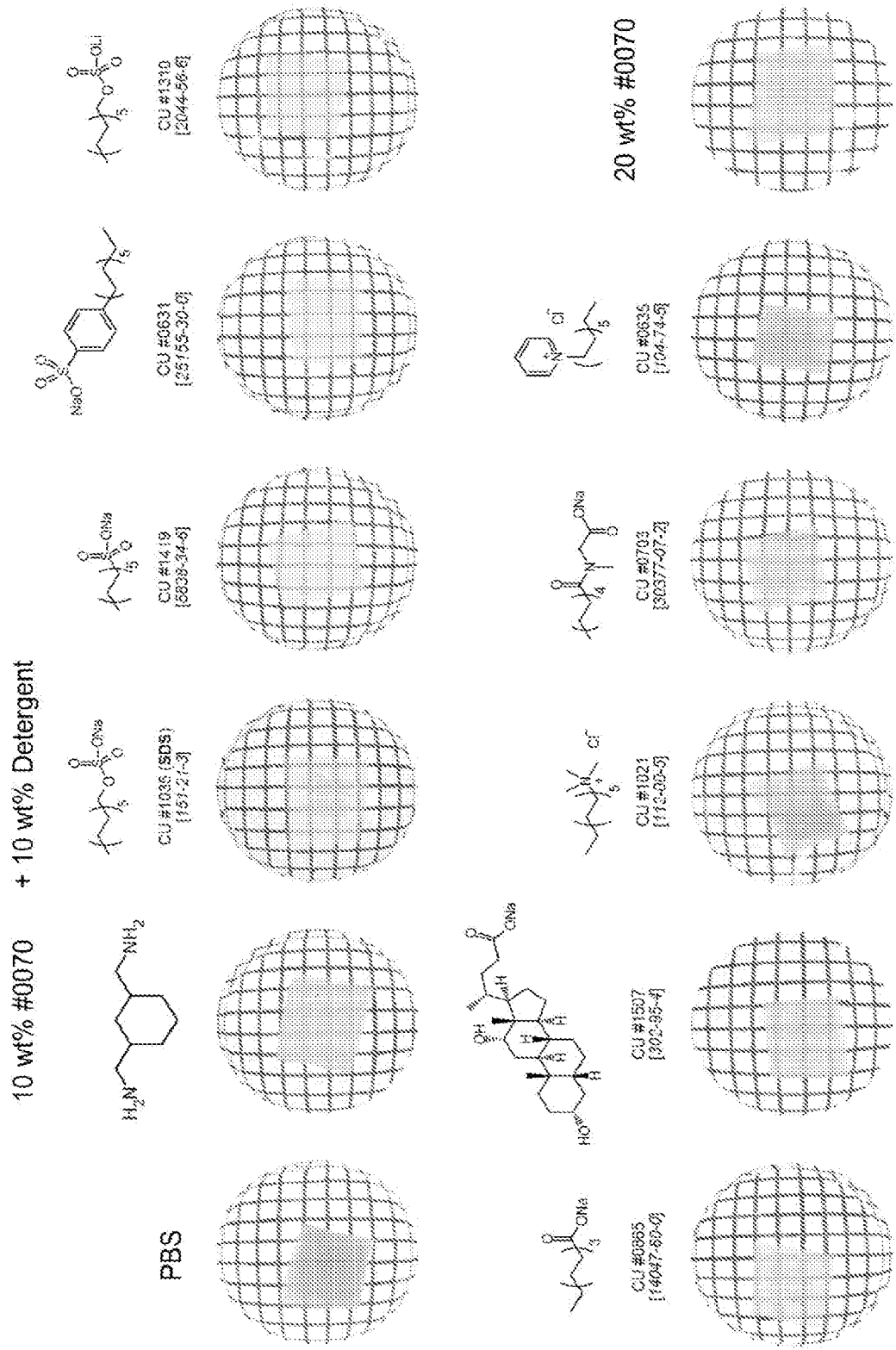
FIG. 6 is a view showing a comparison of clearing of human brain white matter caused with use of 10 wt % #0070+each 10 wt % detergent in an Example of the present invention.

Further, in order to search for an optimal detergent, various cocktails of 10 wt % #0070+10 wt % detergent were prepared and compared with each other in terms of clearing of human brain white matter (FIG. 6). It was thus revealed that a cocktail of 10 wt % #0070+10 wt % #0631 is an optimal combination.

Figure 7:
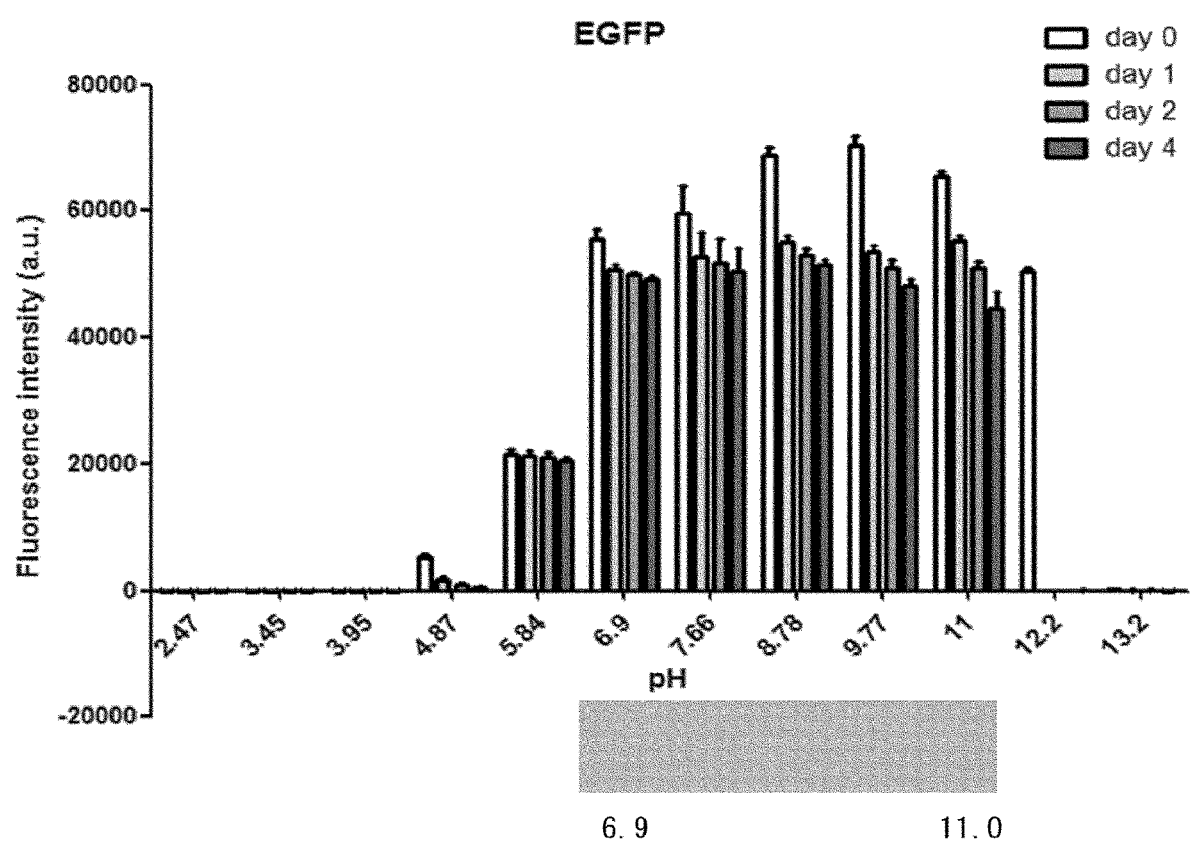
FIG. 7 is a view showing a correlation between fluorescence intensity of EGFP and pH in an Example of the present invention.
Figure 8:
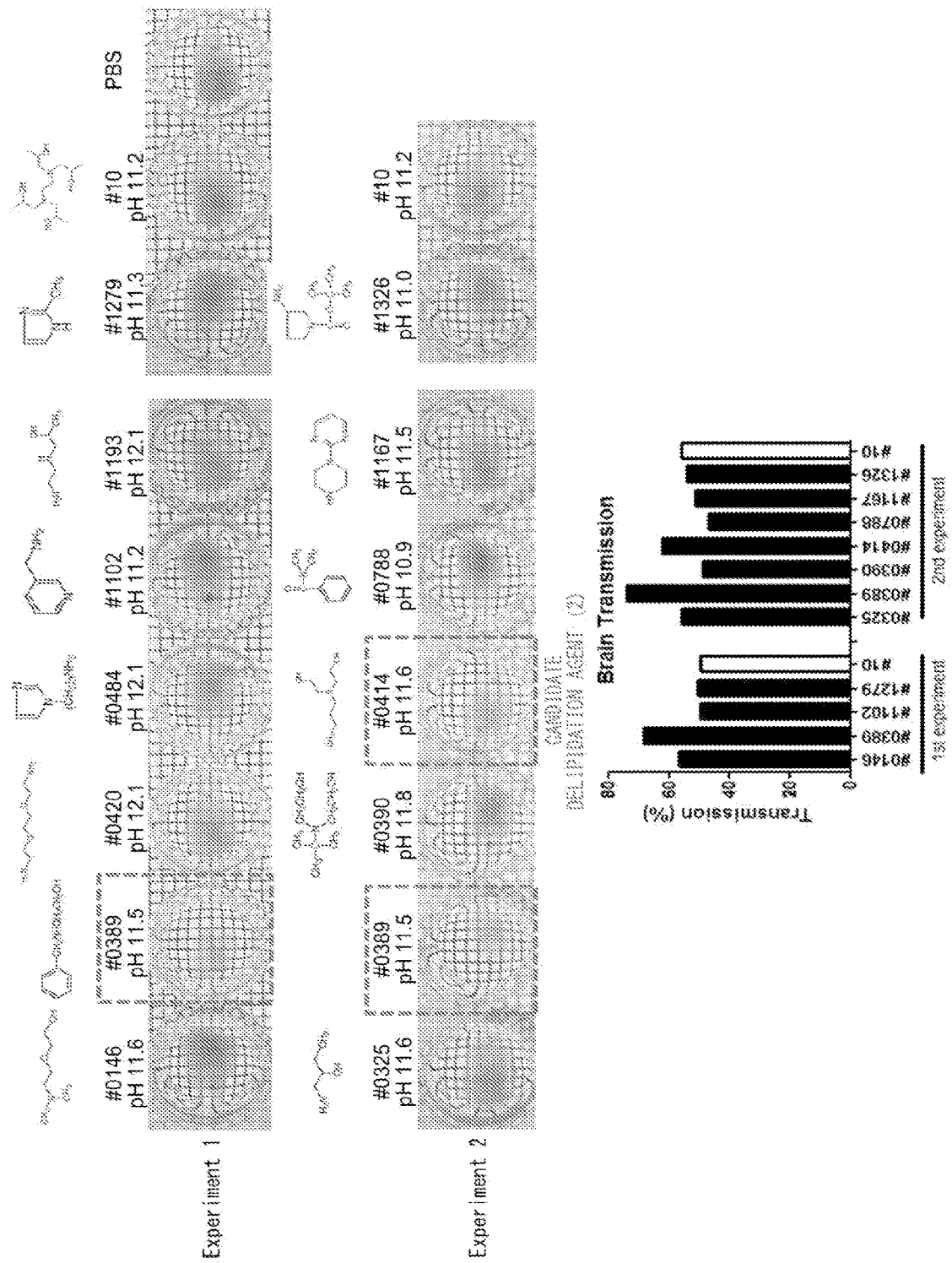
FIG. 8 is a view showing a comparison of transparency of a mouse hemisphere in a case of using each basic chemical in an Example of the present invention.

It was shown that fluorescence of EGFP, which is a typical fluorescent protein, is quenched at a pH of 12 or more at 37° C. (FIG. 7). As such, only those basic chemicals which had a pH of 11 to 12 were subjected to comparison in terms of transparency of mouse hemispheres (FIG. 8). A mouse hemisphere was treated with use of each 10 wt % chemical solution at 37° C. for 3 days, and was washed with PBS. Subsequently, the mouse hemisphere was subjected to refractive index adjustment with CUBIC-2A. From results obtained, #0389 and #0414 were selected. However, various studies which were thereafter conducted showed superiority of #0414 in terms of organ transparency. Accordingly, #0414 (N-butyldiethanolamine) was selected as a highly-efficient delipidation chemical.

Figure 10:
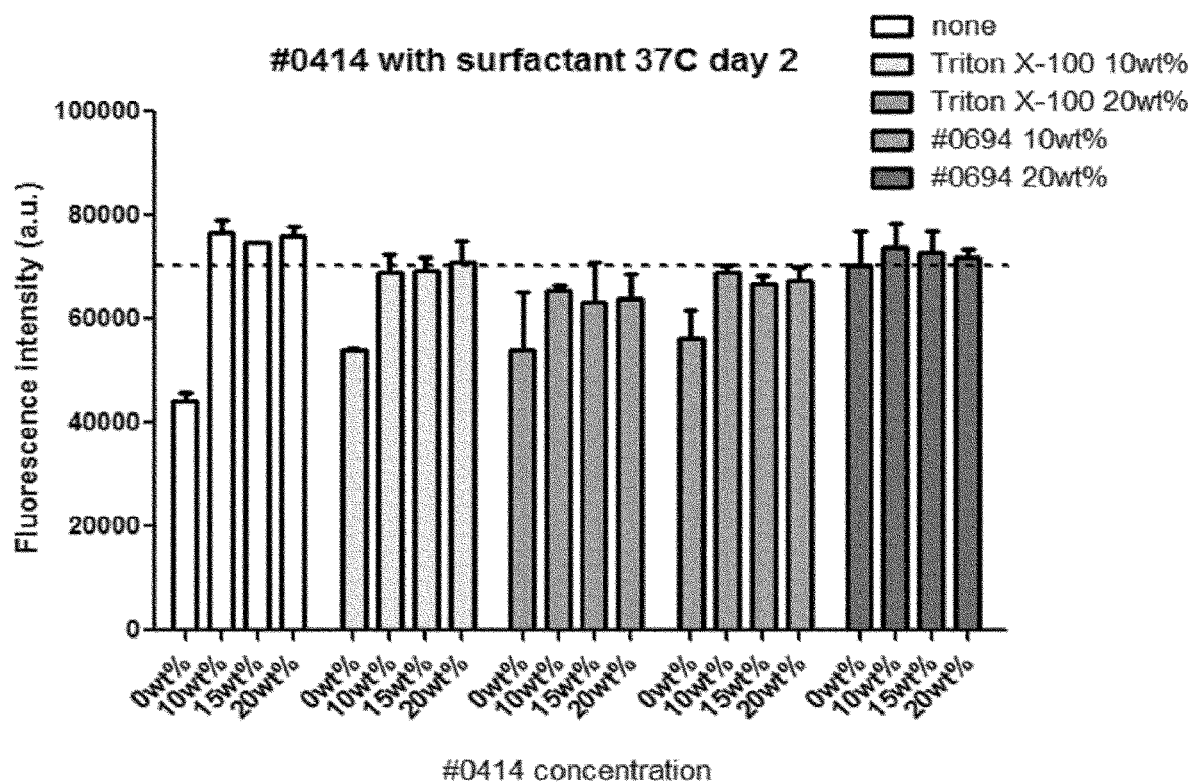
FIG. 10 is a view showing efficiency of quenching of EGFP in a case of using each #0414 cocktail in an Example of the present invention.

Subsequently, a study was conducted to identify a combination of #0414 and another chemical which combination would synergistically contribute to delipidation so as to maximize delipidation activity (FIG. 9). A mouse kidney was treated with use of a cocktail of 10 wt % #0414+each 10 wt % chemical at 37° C. for 1 day, washed with PBS, and then subjected to refractive index adjustment with CUBIC-2A. It was thus revealed that a combination of #0414 and TRITON™ X-100 (2-[4-(2,4,4-trimethylpentan-2-yl)phenoxy]ethanol) is optimal in terms of both delipidation activity and transparency. It was also revealed that the cocktail of #0414+TRITON™ X-100 (2-[4-(2,4,4-trimethylpentan-2-yl)phenoxy]ethanol) does not induce quenching of EGFP (FIG. 10). A mouse whole brain was treated with use of a cocktail of 10 wt % #0414+10 wt % TRITON™ X-100 (2-[4-(2,4,4-trimethylpentan-2-yl)phenoxy]ethanol) at 37° C. for 3 days, washed with PBS, and then subjected to refractive index adjustment with CUBIC-2A. It was thus confirmed that the cocktail of #0414+TRITON™ X-100 (2-[4-(2,4,4-trimethylpentan-2-yl)phenoxy]ethanol) yields significant improvements in transparency and delipidation efficiency as compared with a conventional CUBIC-1 reagent (FIG. 11).

(B. Biochrome Decoloring Ability)

A high-throughput screening system for evaluating the decoloring ability of various compounds was constructed. The screening system involved adding an aqueous solution of each compound to bovine coagulated blood and then measuring the absorbance of heme collected in the supernatant. The screening system was used to screen the library of 1619 water-soluble compounds for a compound having a biochrome decoloring ability.

Specifically, to bovine blood, an equal amount of 8% PFA solution was added, and reacted at 4° C. overnight. The mixed liquid was centrifuged at 1500×g for 5 minutes, and the supernatant containing PFA was discarded. Then, the same amount of PBS as the original volume of blood was added to prepare a coagulated blood sample. To 150 μL of 10 wt % aqueous solution of each compound, 50 μL of the coagulated blood sample was added, and reacted at 37° C. overnight. The reaction solution was centrifuged at 1500×g for 5 minutes, and then 100 μL of the supernatant was added to a plate so as to be subjected to absorbance measurement. A sample which is suspended in water instead of being dissolved in the water has a weak decoloring effect, but none the less has a high absorbance value. In view of this, the OD720 and OD420 of the supernatant were measured as a scattering index and a heme elution index, respectively. OD420-OD700 was defined as decoloring activity of each chemical, and chemicals exhibiting a decoloring activity higher than that of an aminoalcohol (N,N,N',N'-tetrakis(2-hydroxypropyl)ethylenediamine), which had been already known to exhibit a decoloring activity, were identified (FIG. 31/Table. 2). This screening allowed identifying, as a group of compounds having a notably high decoloring activity, (i) detergents typified by alkyl imidazole and a salt of pyridinium and (ii) bases such as alkylamine.

In order to examine the decoloring efficiency of the series of compounds in mammalian tissue, a mouse spleen was treated at 37° C. overnight with use of 10 wt % solution of each chemical which solution would not induce quenching of EGFP. Subsequently, the OD420 of the supernatant was measured, and a transmissive image of the organ was captured (FIG. 12). The results showed that #0938 (1-ethylimidazole) had the highest mouse spleen decoloring activity. Since this reagent is expensive (176 yen per gram), 1-methylimidazole (25.8 yen per gram) was selected as an alternative having an equivalent decoloring activity. In hemoglobin, heme is coordinate-bonded to oxygen and histidine. 1-alkyl imidazole has a skeleton similar to that of histidine, and is thus assumed to have high affinity for heme. This seems to be a factor that allowed the 1-alkyl imidazole to exhibit a high decoloring activity. Meanwhile, little decoloring activity was observed with respect to imidazoles whose nitrogen atom at the position 1 was not alkylated. It is thus understood that alkylation of a nitrogen atom at the position 1 improves affinity for heme.

(C. Decalcification Ability)

For comprehensive screening of the library of 1619 water-soluble compounds for a compound having a decalcification activity, a screening system involving use of hydroxyapatite, which is a main component of bone tissue, was constructed. Hydroxyapatite (200 mg/mL) was suspended in 40 v/v % glycerol, and mixed with an aqueous solution of each compound. Then, the turbidity of the mixed solution was measured. Specifically, 20 μL of a 200 mg/mL hydroxyapatite-40 v/v % glycerol suspension was dispensed to each well of a 96-well plate reader. 130 μL of each reagent was added to the well, and was shaken and stirred at 37° C. overnight. Then, the OD600 of each mixture was measured to evaluate the decalcification activity of the mixture. With respect to an OD600 value (defined as score 1.0) obtained in a case where the treatment was performed with use of water, the score of each compound aqueous solution was calculated. The closer the score of a chemical is to 0, the higher the decalcification activity of the chemical is. Decalcification is commonly known to progress quickly in the presence of a strong acid such as hydrochloric or nitric acid. Under such a condition, it is not possible to observe signals of a fluorescent protein. Meanwhile, EDTA, which is in a neutral range, allows maintaining signals of a fluorescent protein. However, EDTA has a decalcification ability lower than those of strong acids, and thus requires long hours of decalcification operation. Development was conducted in the present invention to obtain a solution which would exhibit a significant decalcification activity when combined with the EDTA in the neutral range. Screening results showed that most of the compounds having a pH of less than 2.0 had a score 0. Accordingly, a group of compounds having a pH of 2.0 or more is listed in Table. 4, in which the compounds are sorted in accordance with characteristics of their structure formulae. Among the group of compounds, those compounds having a low score are shown in boxes.

In order to examine whether or not these compounds are effective for decalcification, a cocktail was prepared by neutralizing a mixed solution of 10 wt % EDTA+each 10 wt % decalcification-candidate compound to a pH of 7 to 8 with use of a solution of #0070, which had been found to be useful as a delipidation reagent. A mouse femur was treated with use of (i) an EDTA-Na solution with a pH adjusted to 7 to 8 using NaOH or (ii) an EDTA—each decalcification candidate compound—#0070 solution. Then, a change in transmittance of the femur was measured (this experiment was conducted twice independently). It was thus discovered that the EDTA—decalcification candidate compound—#0070 solutions exhibited a significantly improved decalcification activity as compared with the conventional EDTA-Na solutions (FIG. 13). Further, no quenching of GFP was observed. From the results of FIG. 13, it was revealed that an EDTA—#1165-#0070 solution and an EDTA—#1300-#0070 solution were the most effective decalcification reagents.

Subsequently, an attempt was made to study how to optimize the basic chemical which had been used for the pH adjustment. Since an experimental system using a femur would create significant experimental errors, an evaluation system using hydroxyapatite was used in the study in order to conduct more detailed optimization of the decalcification activity of EDTA. Specifically, 20 μL of a 60 mg/mL or 200 mg/mL hydroxyapatite-40 v/v % glycerol suspension was dispensed to each well of a 96-well plate reader. 130 μL of each reagent was added to the well, and was shaken and stirred at 37° C. overnight. Then, the OD600 of each mixture was measured to evaluate the decalcification activity of the mixture. A cocktail was prepared by neutralizing 10 wt % EDTA to a pH of approximately 8 with use of a basic amine typified by #0070, #0390, #0414, #1027, #1439, and #1456, which had been found to be useful as a delipidation reagent. The evaluation conducted with use of the prepared cocktails showed that 10 wt % EDTA—#0414 exhibited the most effective decalcification action (FIG. 14).

With respect to a cocktail obtained by neutralizing 10 wt % EDTA with use of #0414 (EDTA—#0414) and a cocktail obtained by neutralizing 10 wt % #0414 with use of EDTA (#0414—EDTA), pH dependency of the decalcification activity of these cocktails was examined. Remarkably higher decalcification activities of these cocktails as compared with those of conventional EDTA-NaOH solutions were confirmed at a pH of approximately 8 (FIG. 15). Studies of temperature dependency and EDTA concentration dependency showed that (i) the decalcification activity increased as the temperature increased and (ii) the decalcification activity was maximized at an EDTA concentration of approximately 10 wt % (FIG. 16). On the basis of these conditions, clearing was conducted on a mouse femur, around which tissues had been dissolved with use of sodium hydrate. Efficient progress of decalcification was observed in the clearing.

Figure 17:
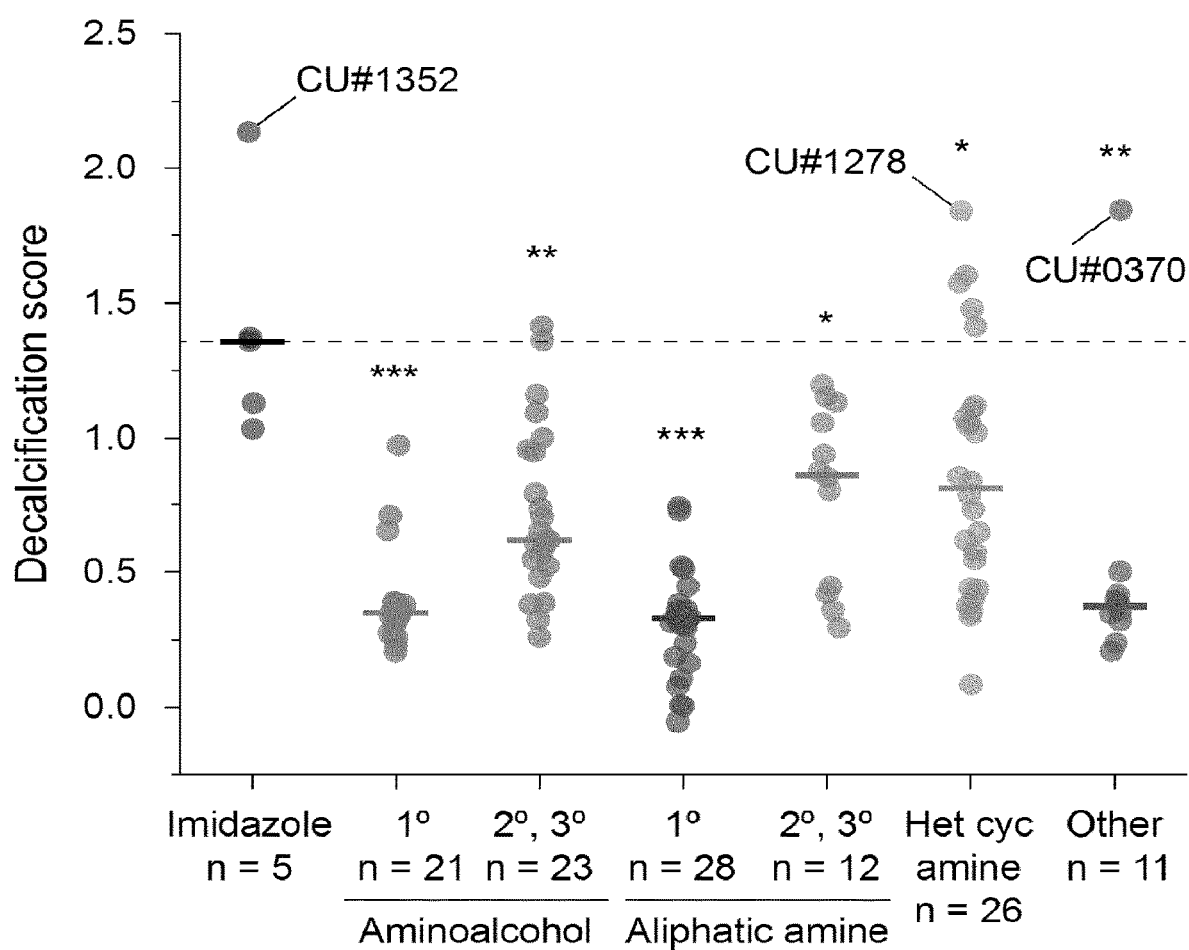
FIG. 17 is a view showing a comparison of decalcification activity in a case of using 10 wt % EDTA+each basic chemical in an Example of the present invention.

Further, comprehensive search for a basic chemical was conducted with use of an evaluation system involving use of hydroxyapatite. Specifically, 20 μL of a 150 mg/mL hydroxyapatite-40 v/v % glycerol suspension was dispensed to each well of a 96-well plate reader. 130 μL of each reagent was added to the well, and was shaken and stirred at 37° C. overnight. Then, the OD600 of each mixture was measured to evaluate the decalcification activity of the mixture. A cocktail was prepared by neutralizing 10 wt % EDTA to a pH of approximately 8 with use of a basic chemical having a pH of 11 or more. With use of the prepared cocktail, a decalcification treatment was conducted (FIG. 17). Comparison of relative decalcification activities showed that imidazole analogs had decalcification activities superior to those of the other categories. In particular, a cocktail neutralized by #1352 (imidazole) exhibited the highest decalcification. Also, a cocktail neutralized by #1278 (4-methylmorpholine), which is a heterocyclic amine, and a cocktail neutralized by #0370 (2-amino-6-methylpyridine) having a pyridine skeleton, exhibited high decalcification activities.

(D. Refractive Index Adjusting Ability)

The refractive index of an aqueous solution is commonly known to increase in a solute concentration-dependent manner, and the refractive index of a reagent per unit weight of the reagent varies among individual reagents. Accordingly, two properties are required in order to prepare a high refractive index aqueous solution: (1) an extremely high water-solubility and (2) a solvent which allows achieving a high refractive index in a low-concentration aqueous solution. In order to conduct a comprehensive search of the library of 1619 water-soluble compounds for a reagent satisfying the above (2), the refractive index at 589 nm of 10 wt % aqueous solution of each compound was measured so as to screen for compounds having a high refractive index. In order to further select a compound having a high water-solubility from among these compounds, 60 wt % to 80 wt % aqueous solution was prepared, and a group of compounds having a refractive index of 1.47 to 1.50 was identified (FIG. 32/Table. 3).

From the viewpoint of preventing shrinkage, a comparison was made of 7 salt-free compounds among the group of compounds in terms of refractive index adjusting effect. Specifically, a kidney of an 8-week old male mouse was shaken in a 10 wt % #0414+10 wt % TRITON™ X-100 (2-[4-(2,4,4-trimethylpentan-2-yl)phenoxy]ethanol) mixed solution at 37° C. for 4 days, and then washed with PBS. Further, the kidney was shaken in a 2-fold diluted high refractive index solution at 37° C. overnight. Subsequently, the kidney was further shaken in an undiluted high refractive index solution at 37° C. overnight. Then, a transmissive image of the kidney was captured, and the transmittance of tissue of the kidney was measured (FIG. 18). Note that CUBIC-2A solution, 70 wt % Histodenz solution, and 70 wt % sucrose solution were used as controls. The measurement results showed that, as compared with the high-concentration Histodenz solution and the high-concentration sucrose solution which had been already reported, #0587, #0640, #1102, and #1283 achieved better results in terms of both the appearance and transmittance of the organ.

Subsequently, in order to search for high-level refractive index adjusting agents with use of cocktails of these chemicals, various 46 wt %/30 wt % mixed solutions were prepared. A lung of an 8-week old male mouse was shaken in a 10 wt % #0414+10 wt % TRITON™ X-100 (2-[4-(2, 4,4-trimethylpentan-2-ylphenoxy]ethanol) mixed solution at 37° C. for 4 days, and then washed with PBS. Further, the lung was shaken at 37° C. overnight in a 2-fold diluted high refractive index solution. Subsequently, the lung was further shaken in an undiluted high refractive index solution at 37° C. overnight. Then, a transmissive image of the lung was captured, and the transmittance of tissue of the lung was measured (FIG. 19). The measurement results showed that all of the cocktails achieved good transparency, and particularly a cocktail of 46 wt % #0640+30 wt % #1283, a cocktail of 46 wt % #0640+30 wt % nicotinamide (#0855), and a cocktail of 46 wt % Histodenz+30 wt % #1283 had the highest transparencies.

(E. Tissue Swelling Ability)

It is commonly known that causing tissue to swell allows increasing the transparency of the tissue. A high correlation between a swelling-shrinking behavior of a brain and a swelling-shrinking behavior of gelatin was confirmed, and a screening system involving use of gelatin was established. 9% gelatin aqueous solution and 0.8% paraformaldehyde solution were mixed together. 200 μL of the mixed solution was dispensed to each well of a 96-well plate, and then incubated at 4° C. for 16 hours. To the gelatin plate thus gelated, 170 μL of 10 wt % aqueous solution of each compound from the library of 1619 water-soluble compounds was dispensed, and was incubated at room temperature for 72 hours. Then, the gelatin plate was washed with use of pure water approximately 3 times. The water was thoroughly wiped off, and the absorbance of the gelatin at 975 nm, which is one of the absorption wavelengths of water, was measured. The library of 1619 water-soluble compounds was screened for a group of compounds each having a swelling activity score higher than that (score 1) of urea. As a result, water-soluble compounds having a swelling activity were identified (FIG. 20).

In order to verify that the identified compounds actually had an activity of swelling a mouse brain, a brain which had been subjected to a delipidation treatment with use of CUBIC-1 was shaken, in a solution containing #1352 among the compounds, for 3 days while replacing the liquid every 12 hours. As a result, a high-degree of swelling was observed (FIG. 21). Further, in order to verify that the swollen brain actually exhibits high transparency, the brain which had been swollen with use of #1352 was shaken in a 55 wt % #0640+5 wt % #1352 mixed solution which had a high refractive index adjusting ability. A brain sample which had very high transparency while in a swollen state was successfully produced (FIG. 22).

[2. Example Use of Clearing Reagent]

(1. Clearing of Mouse Liver and Tissue Including Human Brain White Matter)

Clearing of a mouse liver and tissue including human brain white matter can be performed, for example, in accordance with the following procedure.

(1) A liver of a mouse which has been subjected to perfusion fixation with use of 4% paraformaldehyde solution or human brain tissue which has been fixed with use of formalin is immersed in PBS.

(2) The mouse liver or the human brain tissue is immersed in a permeabilization solution (Sol. PE: 10 wt % 1,3-bis(aminomethyl)cyclohexane, 10 wt % sodium dodecylbenzenesulfonate or sodium dodecyl sulfate) at 37° C. for 2 days to 4 days.

(3) The mouse liver or the human brain tissue is washed with PBS several times for several hours per washing.

(4) The mouse liver or the human brain tissue is immersed in a clearing solution (Sol. CL: 22.5 wt % sucrose, 22.5 wt % antipyrine, 10 wt % triethanolamine, 25% urea) at 50° C. for approximately 2 days to 4 days.

(5) The mouse liver or the human brain tissue is washed with PBS again as necessary, and preserved.

Results of clearing actually performed in accordance with the above procedure are shown in FIG. 23.

(2. Decoloring of Mouse Spleen)

Decoloring of a mouse spleen can be performed, for example, in accordance with the following procedure.

(1) Spleen tissue of a mouse which has been subjected to perfusion fixation with use of a 4% paraformaldehyde solution is immersed in PBS.

(2) The spleen tissue is immersed in 10 wt % #0441 (benzethonium chloride), #0484 (1-(3-aminopropyl) imidazole), #0651 (decyldimethyl(3-sulfopropyl)ammonium hydroxide intramolecular salt), #0938 (1-ethylimidazole), or #1283 (N-methylnicotinamide) at 37° C. for approximately 2 days to 4 days. As controls, spleen tissue is immersed in #10 (N,N,N',N'-tetrakis(2-hydroxypropyl)ethylenediamine), CUBIC-1, or PBS at 37° C. for approximately 2 days to 4 days.

(3) An image of each spleen tissue thus decolored is captured. Heme eluted into a supernatant is quantified by measuring the absorbance of the spleen at 420 nm.

Results of decoloring actually performed in accordance with the above procedure are shown in FIG. 12.

(3. Clearing of Mouse Brain Tissue)

Clearing of mouse brain tissue can be performed, for example, in accordance with the following procedure.

(1) Brain tissue of a mouse which has been subjected to perfusion fixation with use of 4% paraformaldehyde solution is immersed in PBS, and cut into brain hemispheres.

(2) Each brain hemisphere is immersed in a brain delipidation solution (10 wt % N-butyldiethanolamine, 10 wt % TRITON™ X-100 (2-[4-(2,4,4-trimethylpentan-2-yl)phenoxy]ethanol)) at 37° C. for approximately 2 days to 4 days.

(3) The brain hemisphere is washed with PBS several times for several hours per washing.

(4) The brain hemisphere is immersed in a clearing solution (Sol. CL: 22.5 wt % sucrose, 22.5 wt % antipyrine, 10 wt % triethanolamine, 25% urea) at 37° C. for approximately 1 day.

(5) The brain hemisphere is washed with PBS again as necessary, and preserved.

Figure 24:
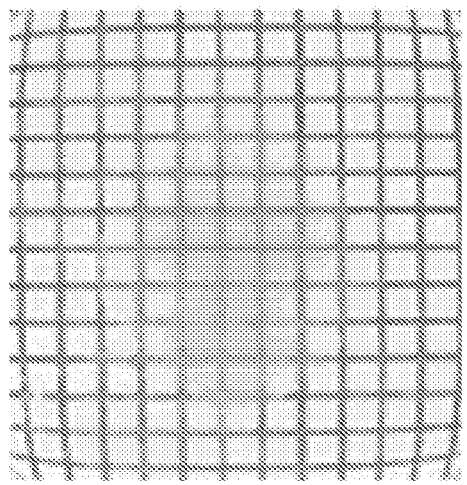
FIG. 24 is a view showing clearing of mouse brain tissue in an Example of the present invention.

A result of clearing actually performed in accordance with the above procedure is shown in FIG. 24.

(4. Adjustment of Refractive Index of Delipidated Tissue)

Adjustment of the refractive index of delipidated tissue can be performed, for example, in accordance with the following procedure.

(1) Brain tissue of a mouse which has been subjected to perfusion fixation with use of 4% paraformaldehyde solution is subjected to post-fixation with use of 4% paraformaldehyde solution. Then, the mouse brain tissue is immersed in PBS, and cut into brain hemispheres.

(2) Each brain tissue thus cut is immersed in CUBIC-1 at 37° C. for approximately 3 days to 5 days.

(3) The brain tissue is immersed in PBS for approximately 1 day.

(4) The brain tissue is immersed in 70 wt % #0389 (N-benzylethanolamine), 60 wt % #0640 (antipyrine), or 70 wt % #0788 (N,N-dimethylbenzamide) at room temperature for approximately 1 day.

Figure 25:
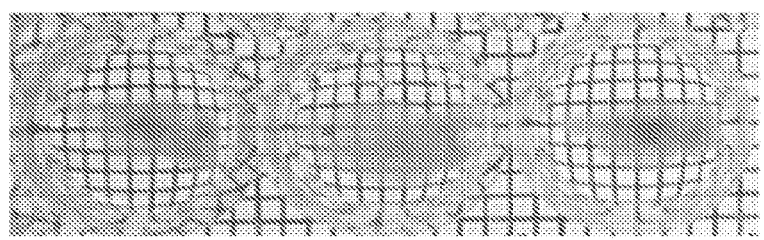
FIG. 25 is a view showing a refractive index adjustment on delipidated tissue in an Example of the present invention.

Results of refractive index adjustment actually performed in accordance with the above procedure are shown in FIG. 25.

(5. Clearing of Various Mouse Organs)

Clearing of various organs (brain, heart, lung, liver, and kidney) of a mouse can be performed, for example, in accordance with the following procedure.

(1) An organ of a mouse which has been subjected to perfusion fixation with use of 4% paraformaldehyde solution is taken out, and subjected to post-fixation with use of 4% paraformaldehyde solution at 4° C. overnight.

(2) The mouse organ is washed with PBS several times for several hours per washing.

(3) The mouse organ is immersed in a permeabilization CUBIC-L solution (Sol. PE CUBIC-L: 10 wt % N-butyldiethanolamine, 10 wt % TRITON™ X-100 (2-[4-(2,4,4-trimethylpentan-2-yl)phenoxy]ethanol)) at 37° C. for approximately 2 days to 4 days.

(4) The mouse organ is washed with PBS several times for several hours per washing.

(5) The mouse organ is immersed, at room temperature overnight, in a clearing CUBIC-R solution (Sol. CL CUBIC-R: 46 wt % antipyrine, 30 wt % nicotinamide) which has been diluted by two folds with use of distilled water.

(6) The mouse organ is immersed in undiluted Sol. CL CUBIC-R for 2 days.

Figure 26:
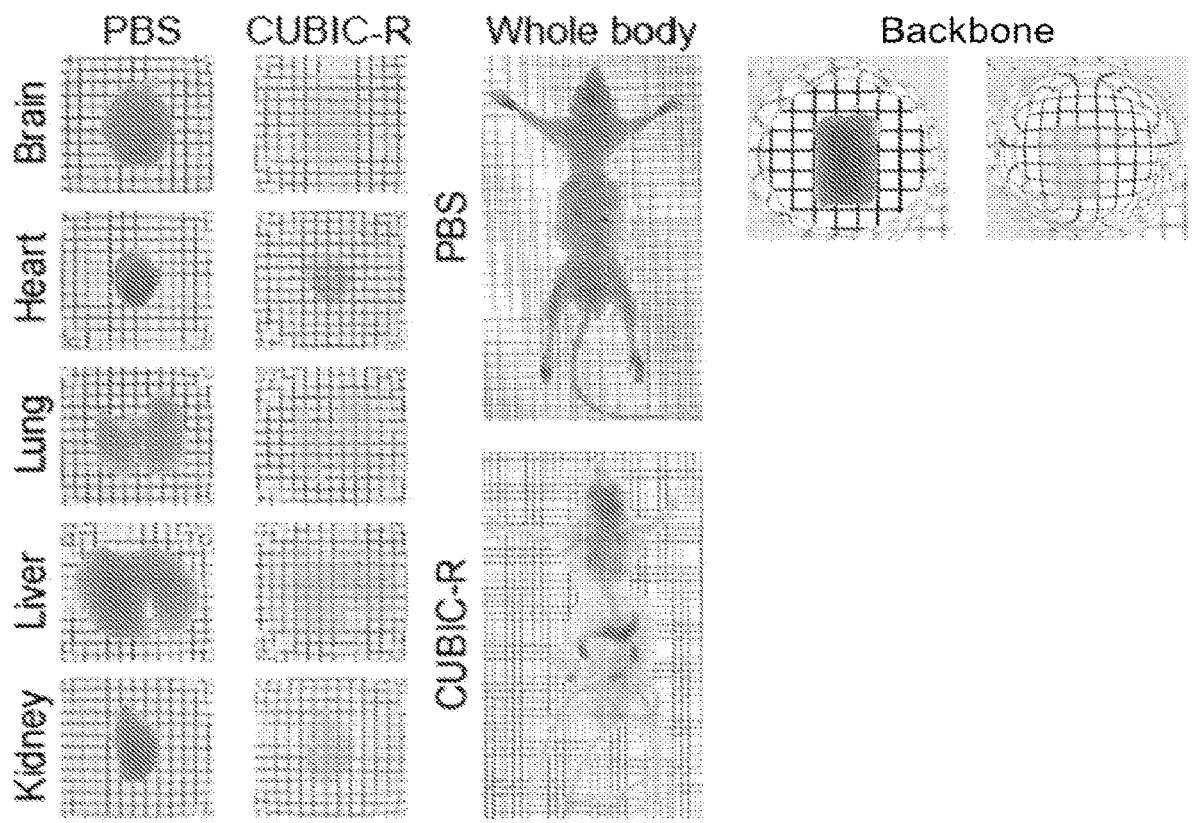
FIG. 26 is a view showing clearing of mouse organs and a mouse whole body in an Example of the present invention.

Results of clearing actually performed are shown on the left hand side of FIG. 26.

Results of clearing actually performed are shown on the left hand side of FIG. 26.

(6. Clearing of Mouse Whole Body)

Clearing of the whole body of a mouse can be performed, for example, in accordance with the following procedure.

(1) A mouse whole body is subjected to perfusion fixation with use of 4% paraformaldehyde solution, and then perfused with 100 mL to 200 mL of Sol. PE CUBIC-L.

(2) The mouse whole body is immersed in Sol. PE CUBIC-L at 37° C. for 7 days, during which the liquid is replaced once every 2 days.
(3) The mouse whole body is washed with PBS several times for several hours per washing, and immersed in PBS at room temperature overnight.
(4) The mouse whole body is immersed, at room temperature overnight, in Sol. CL CUBIC-R which has been diluted by 2 folds with use of distilled water.
(5) The mouse whole body is immersed in undiluted Sol. CL CUBIC-R for 2 days.

Results of clearing actually performed are shown at the center of FIG. 26.

(7. Clearing of Mouse Backbone)

Clearing of the backbone of a mouse can be performed, for example, in accordance with the following procedure.
(1) A backbone of a mouse which has been subjected to perfusion fixation with use of 4% paraformaldehyde solution is taken out, and subjected to post-fixation with use of 4% paraformaldehyde solution at 4° C. overnight.
(2) The mouse backbone is washed with PBS several times for several hours per washing.
(3) The mouse backbone is immersed in Sol. PE CUBIC-L at 37° C. for 3 days.
(4) The mouse backbone is washed with PBS several times for several hours per washing.
(5) The mouse backbone is immersed in a decalcification CUBIC-B solution (Sol. DC CUBIC-B: 10 wt % EDTA, 15 wt % imidazole) at 37° C. for 6 days.
(6) The mouse backbone is washed with PBS several times for several hours per washing.
(7) The mouse backbone is immersed in Sol. PE CUBIC-L at 37° C. for 3 days.
(8) The mouse backbone is washed with PBS several times for several hours per washing.
(9) The mouse backbone is immersed, at room temperature overnight, in Sol. CL CUBIC-R which has been diluted by two folds with use of distilled water.
(10) The mouse backbone is immersed in undiluted Sol. CL CUBIC-R for 2 days.

Results of clearing actually performed are shown on the right hand side of FIG. 26.

(8. Clearing of Human Tissue)
(1) Human tissue is fixed with use of formalin, immersed in PBS, washed several times for several hours per washing, and immersed in PBS at room temperature overnight.
(2) The human tissue is immersed in Sol. PE at 37° C. for approximately 5 days to 10 days.
(3) The human tissue is washed with PBS several times for several hours per washing, and immersed in PBS at room temperature overnight.
(4) The human tissue is immersed, at room temperature overnight, in Sol. CL CUBIC-R which has been diluted by 2 folds with use of distilled water.
(5) The human tissue is immersed in undiluted Sol. CL CUBIC-R for 2 days.

Figure 27:
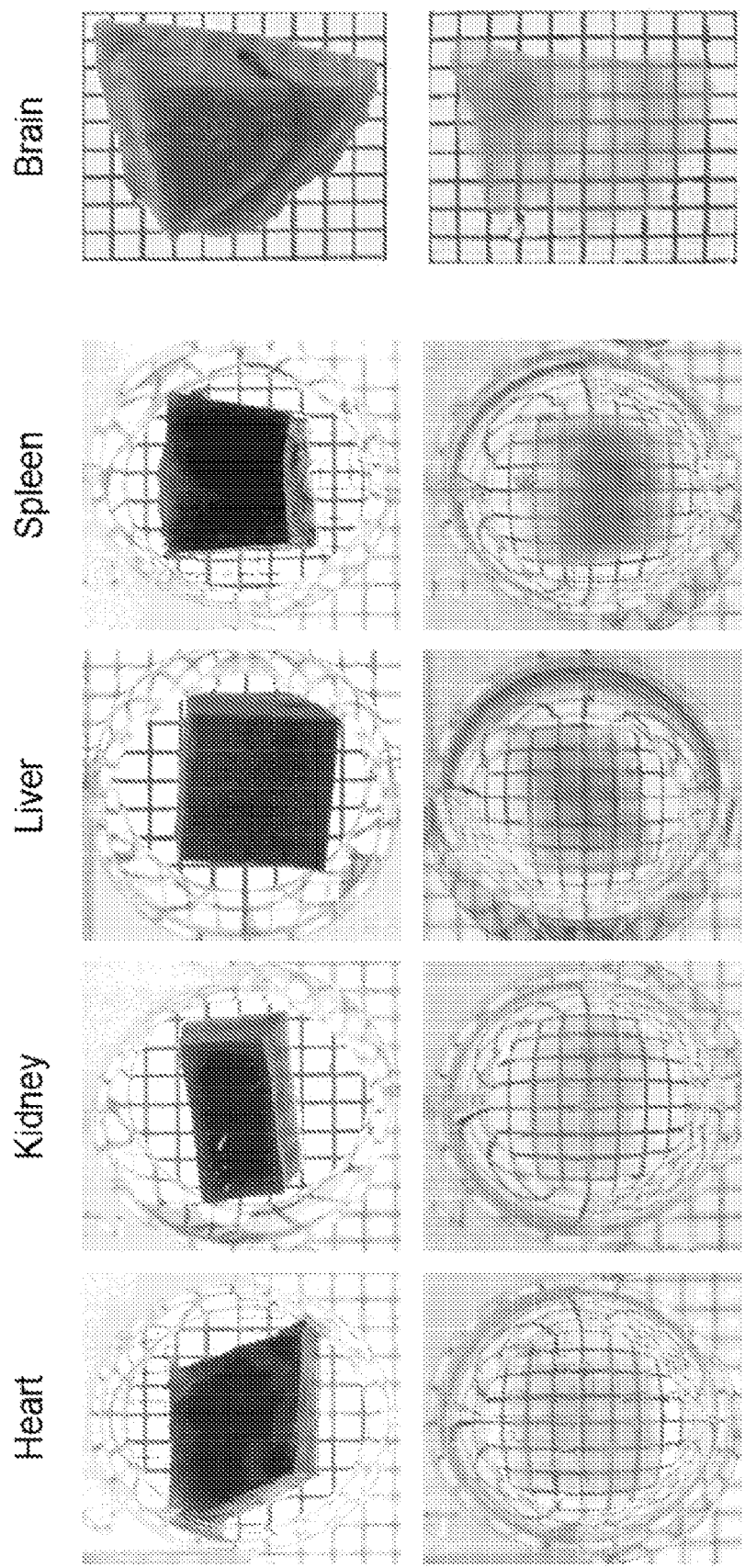
FIG. 27 is a view showing clearing of human tissue in an Example of the present invention.

Results of clearing actually performed are shown in FIG. 27.

(8. Clearing of Human Brain Tissue)
(1) Human tissue is fixed with use of formalin, immersed in PBS, washed several times for several hours per washing, and immersed in PBS at room temperature overnight.
(2) The human tissue is immersed in Sol. PE CUBIC-HBL solution (Sol. PE CUBIC-HBL: 10 wt % N-butyldiethanolamine, 10 wt % TRITON™ X-100 (2-[4-(2,4,4-trimethylpentan-2-yl)phenoxy]ethanol), 15 wt % imidazole) at 37° C. for approximately 5 days to 10 days.
(3) The human tissue is washed with PBS several times for several hours per washing, and immersed in PBS at room temperature overnight.
(4) The human tissue is immersed, at room temperature overnight, in Sol. CL CUBIC-R which has been diluted by 2 folds with use of distilled water.
(5) The human tissue is immersed in undiluted Sol. CL CUBIC-R for 2 days.

Figure 28:
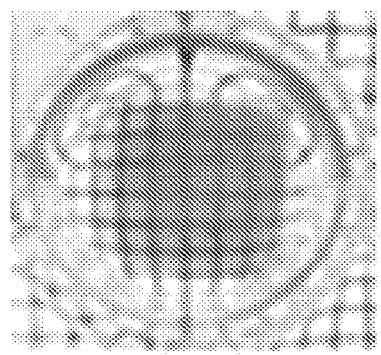
FIG. 28 is a view showing clearing of human brain tissue in an Example of the present invention.

A result of clearing actually performed is shown in FIG. 28.

A result of clearing actually performed is shown in FIG. 28.

(10. Clearing of Marmoset Brain)
(1) A brain of a marmoset which has been subjected to perfusion fixation with use of 4% paraformaldehyde solution is taken out, and subjected to post-fixation with use of 4% paraformaldehyde solution at 4° C. overnight.
(2) The marmoset brain is washed with PBS several times for several hours per washing.
(3) The marmoset brain is immersed in Sol. PE CUBIC-L at 37° C. for approximately 21 days, during which the liquid is replaced once every 2 days.
(4) The marmoset brain is immersed in PBS (hereinafter referred to as "AzidoPBS") containing 0.01% sodium azide at room temperature for 1 week, during which the liquid is replaced every day.
(5) The marmoset brain is immersed in PBS containing 10 μg/mL propidium iodide and 1.5 M NaCl at 37° C. for 12 days.
(6) The marmoset brain is washed by being immersed in AzidoPBS for 2 days, during which the liquid is replaced once every half a day.
(7) The marmoset brain is immersed, at room temperature overnight, in Sol. CL CUBIC-R which has been diluted by 2 folds with use of distilled water.
(8) The marmoset brain is immersed in undiluted Sol. CL CUBIC-R for 4 days.
(9) The marmoset brain is washed by being immersed in AzidoPBS for 2 days, during which the liquid is replaced once every half a day.
(10) The marmoset brain is immersed in 10 wt % imidazole aqueous solution at room temperature for 2 days, during which the liquid is replaced once every half a day.
(11) The marmoset brain is immersed, at room temperature for 4 days, in Sol. CL CUBIC-R (hereinafter referred to as "Sol. CL CUBIC-R2") which contains 1 wt % #0414 and has been diluted by two folds with use of distilled water.
(12) The marmoset brain is immersed in Sol. CL CUBIC-R2 at room temperature for 7 days, during which the liquid is replaced once.
(13) The marmoset brain is washed by being immersed in AzidoPBS for 2 days, during which the liquid is replaced once every half a day.
(14) The marmoset brain is immersed in Sol. PE CUBIC-L at room temperature for 3 days, then at 37° C. for 2 weeks, and further at 45° C. for 1 week. During this sequence of steps, the liquid is replaced once every 2 days.

(15) The marmoset brain is washed by being immersed in AzidoPBS for 2 days, during which the liquid is replaced once every half a day.
(16) The marmoset brain is immersed in PBS containing 10 μg/mL propidium iodide and 1.5M NaCl at 37° C. for 7 days.
(17) The marmoset brain is washed by being immersed in AzidoPBS for 2 days, during which the liquid is replaced once every half a day.
(18) The marmoset brain is immersed in 10 wt % imidazole aqueous solution at room temperature for 2 days, during which the liquid is replaced once every half a day.
(19) The marmoset brain is immersed, at room temperature for 3 days, in Sol. CL CUBIC-R2 which has been diluted by 2 folds with use of distilled water.
(20) The marmoset brain is immersed in Sol. CL CUBIC-R2 at room temperature for 7 days, during which the liquid is replaced once.

Figure 29:
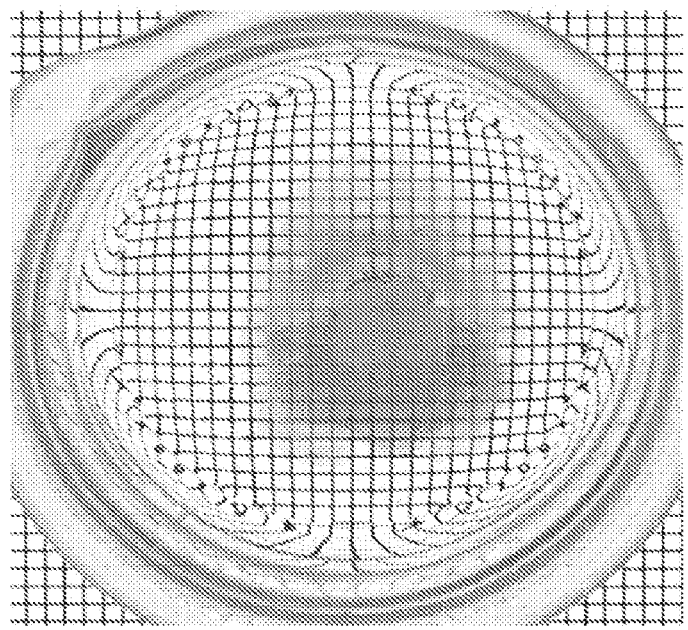
FIG. 29 is a view showing clearing of a marmoset brain in an Example of the present invention.

Results of clearing actually performed are shown at the center of FIG. 29.

TABLE 4

Group 1: Halogenated monocarboxylic acid

0062
5-Chlorovaleric acid

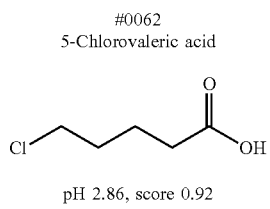

pH 2.86, score 0.92

0074
5-Bromovaleric acid

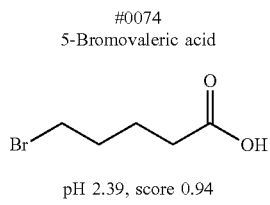

pH 2.39, score 0.94

1162
Ammonium pentadecafluoro-octanoate

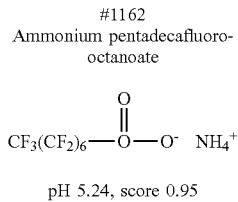

pH 5.24, score 0.95

1577
Dichloroacetic acid

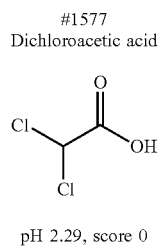

pH 2.29, score 0

TABLE 4-continued

Group 2: Hydroxymonocarboxylic acid

0155
3-Hydroxypropionic acid

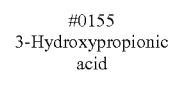

pH 3.66, score 0.91

0175
3-Hydroxycyclohexane carboxylic acid

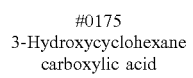

pH 4.22, score 0.92

1307
DL-Lactic acid

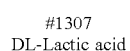

pH 2.14, score 0.78

Group 3: Aliphatic monocarboxylic acid

0073
3-Butenoic acid

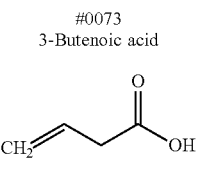

pH 3.43, score 0.82

1569
Cyanoacetic acid

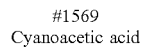

pH 2.61, score 0.52

Group 4: Alkyl amino monocarboxylic acid

0454
Betaine hydrochloride

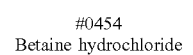

pH 2.07, score 0.31

TABLE 4-continued

0702
3-(Dimethylamino)
propionic acid hydrochloride

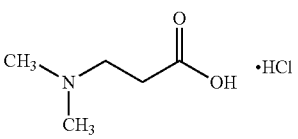

pH 2.17, score 0.91

Group 5: Acetylamino monocarboxylic acid

0346
N-Acetyl-
L-cysteine

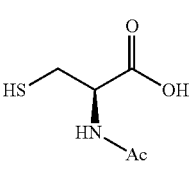

pH 2.86, score 0.94

0360
N-Acetyl-
DL-methionine

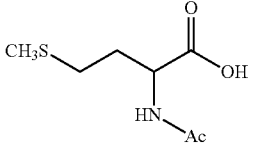

pH 2.75, score 0.94

0350
N-Acetyl-
L-methionine

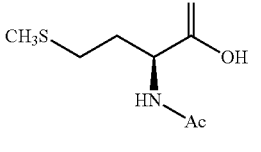

pH 2.74, score 0.94

0741
N-Chloroacetyl
glycine

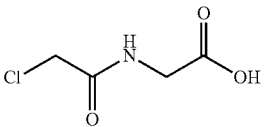

pH 2.43, score 0.87

TABLE 4-continued

0965
DL-Pyro
glutamic acid

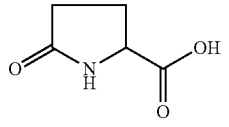

pH 2.33, score 0.86

1071
L-Pyro
glutamic acid

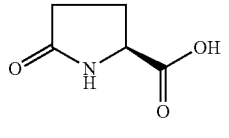

pH 3.01, score 0.86

Group 6: Other monocarboxylic acids

0473
1-Aminocyclobutanecarboxylic
acid hydrochloride

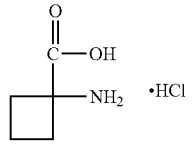

pH 2.18, score 0.84

0534
4-Chloro-DL-mandelic acid

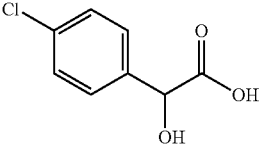 [SMILES: O=C(O)C(O)c1ccc(Cl)cc1]

pH 2.49, score 0.62

0712
Cetirizine dihydrochloride

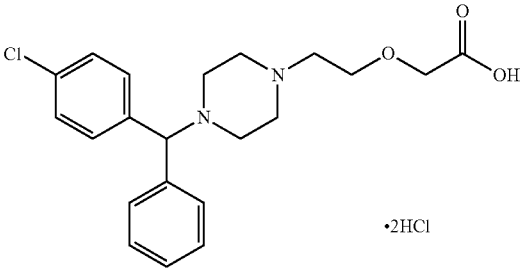 [SMILES: O=C(O)COCCN1CCN(C(c2ccccc2)c2ccc(Cl)cc2)CC1]

pH 3.59, score 0.95

TABLE 4-continued

0746
2-Chloro-L-mandelic acid

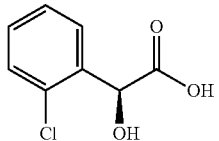 [SMILES: O=C(O)[C@@H](O)c1ccccc1Cl]

pH 2.14, score 0.91

0916
4-[(4-Methyl-1-piperazinyl)
methyl]benzoic acid dihydrochloride

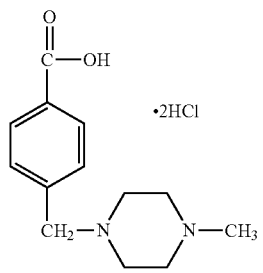 [SMILES: CN1CCN(Cc2ccc(C(=O)O)cc2)CC1]

pH 2.80, score 0.93

0942
N-Formylglycine

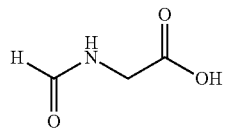

pH 2.67, score 0.77

1108
Ozagrel hydrochloride
hydrate

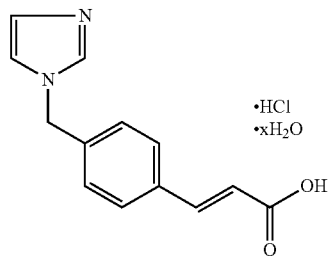 [SMILES: O=C(O)/C=C/c1ccc(Cn2ccnc2)cc1]

pH 4.92, score 0.88

1249
4-Guanidino benzoic
acid hydrochloride

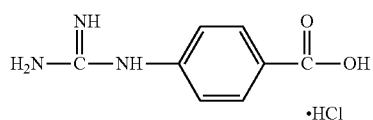

pH 4.22, score 0.91

TABLE 4-continued

1328
3-Bromopyruvic acid

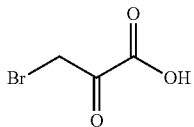

pH 2.13, score 0.67

Group 7: Dicarboxylic acid

1305
Malonic acid

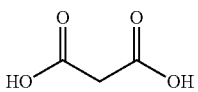

pH 2.33, score 0.32

Group 8: Malic acid

1300
DL-Malic acid

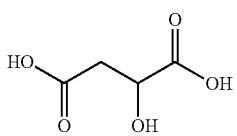

pH 2.34, score 0.42

Group 9: Thiodicarboxylic acid

1302
Thiomalic acid

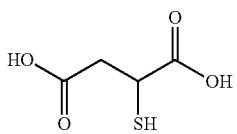

pH 2.68, score 0.85

Group 10: Tartaric acid

0621
2-(Dimethylamino)ethanol
L-(+)-bitartrate

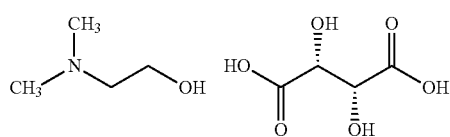

pH 4.43, score 0.93

TABLE 4-continued

0749
L-Carnitine L-tartrate

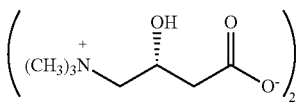

pH 4.65, score 0.93

1428
DL-Tartaric acid

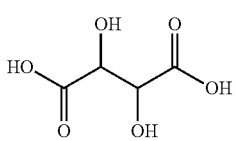

pH 2.18, score 0.49

1594
Nicotine bi-L-(+)-tartrate dihydrate

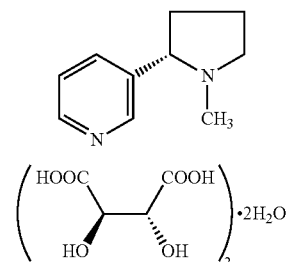

pH 4.84, score 0.71

Group 11: Malonic acid

0762
Cyclopentyl malonic acid

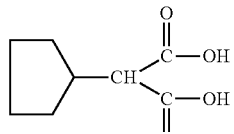

pH 2.74, score 0.53

Group 12: Other dicarboxylic acids

0936
Ethylenediamine-N,N'-dipropionic acid dihydrochloride

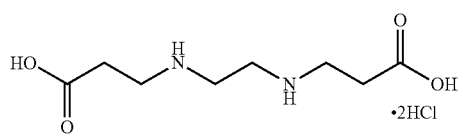 [SMILES: O=C(O)CCNCCNCCC(=O)O]

pH 2.22, score 0.88

TABLE 4-continued

Group 13: Polyvalent carboxylic acid

0692
Diammonium ethylene-diaminetetraacetate monohydrate

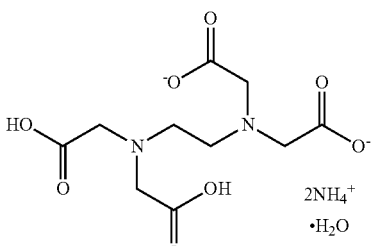

pH 4.97, score 0.92

1094
1,2,3-Propanetri-carboxylic acid

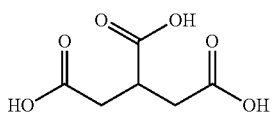

pH 2.69, score 0.91

Group 14: Sugars

0963
D-(+)-Glucono-1,5-lactone

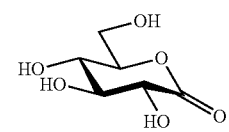

pH 2.69, score 0.88

1010
Lactobionic acid

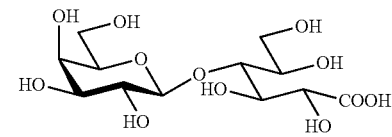

pH 2.63, score 0.95

1203
D-Glucuronic acid

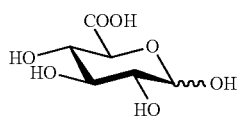

pH 2.04, score 0.70

TABLE 4-continued

1534
Gluconic Acid

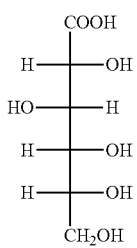

pH 2.60, score 0.91

Group 15: Tetrafluoroborate

1156
Pottasium phenyl
trifloroborate

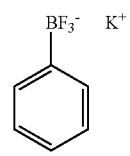

pH 3.60, score 0.35

1562
2-Bromo-1-ethylpyridinium
tetrafluoroborate

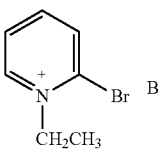

pH 3.92, score 0.50

1598
[(Oxido)phenyl(trifluoromethyl)-λ⁴-
sulfanylidene]dimethylammonium
tetrafluoroborate

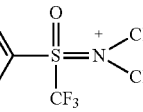

pH 4.52, score 0.93

1608
N-Fluoro-N'-(chloromethyl)
triethylenediamine bis
(tetrafluoroborate)

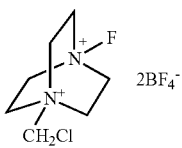

pH 5.19, score 0.26

TABLE 4-continued

1609
Tetraethylammonium
tetrafluoroborate

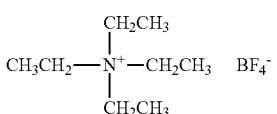

pH 4.03, score 0.45

Group 16: Phosphonic acids

1004
Isopropyl phosphate

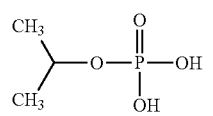

pH 2.40, score 0

Group 17: Sulfonic acids

0745
L-cysteic acid

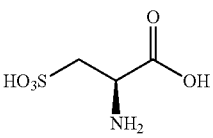

pH 2.11, score 0.44

1165
Pyridine-3-sulfonic acid

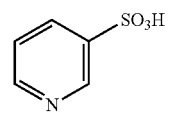

pH 2.21, score 0.89

1213
DL-Homocysteinethiolactone
hydrochloride

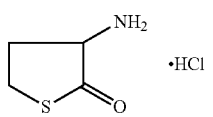

pH 2.31, score 0.94

TABLE 4-continued

Group 18: Hydrocarbon

0216
Ethyl trans-4-hydroxy-
cyclohexanecarboxylate

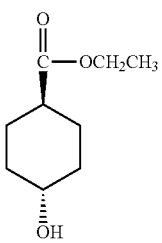

pH 5.68, score 0.94

1109
1,2-Octanediol

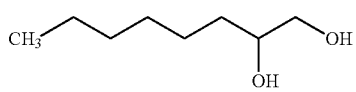

pH 6.00, score 0.95

1365
4-Chloro-1-butanol
(contains tetrahydrofuran)

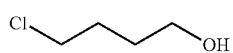

pH 3.08, score 0.87

1366
4-Bromo-1-butanol
(contains tetrahydrofuran)

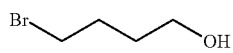

pH 2.31, score 0.63

Group 19: Amines

0071
1,4-Bis(aminomethyl)
cyclohexane

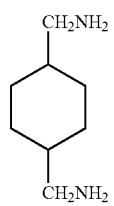

pH 13.27, score 0.94

TABLE 4-continued

0480
1-(2-Aminoethyl)-4-methyl-
piperazine hydrochloride

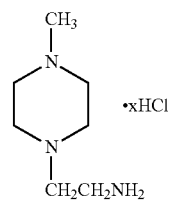

pH 2.67, score 0.63

1390
1,4,7-Triazacyclononane
trihydrochloride

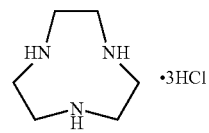

pH 2.08, score 0.89

Group 20: Hydrazine

1280
Methylhydrazine
sulfate
$CH_3NHNH_2 \cdot H_2SO_4$
pH 2.09, score 0.74

Group 21: Aromatic amine

0429
O-Benzylhydroxylamine
hydrochloride

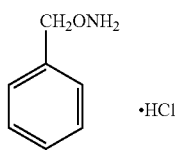

pH 4.10, score 0.24

1610
o-Toluidine hydrochloride

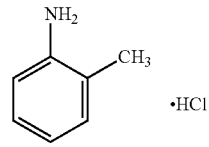

pH 4.23, score 0.94

Base chemical

1439
N,N,N',N'-Tetramethylethylenediamine

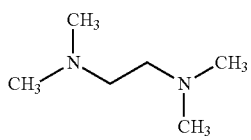

INDUSTRIAL APPLICABILITY

The present invention is applicable, for example, to a high-throughput observation of gene expression, cellular localization, and cell morphology within a whole tissue.

The invention claimed is:

1. A method comprising
preparing a light-transmitting biological material by permeating an aqueous solution into a biological material, wherein the aqueous solution comprises at least one compound selected from the group consisting of benzylamine, 2,3-dimethyl-1-phenyl-5-pyrazolone, xylazine hydrochloride, 2-amino-6-methylpyridine, 2-methylpyridine N-oxide, S-[2-(dimethylamino)ethyl]isothiourea dihydrochloride, diphenhydramine hydrochloride, benzyldimethylphenylammonium chloride, DL-phenylephrine hydrochloride, 4-methylpyridine N-oxide, N-methylnicotinamide, tolperisone hydrochloride, bis(2-dimethylaminoethyl)disulfide dihydrochloride, 3-picolylamine, neostigmine bromide, hydrazine carbonate, N,N-dimethylbenzamide, N-benzylethanolamine, benzyltributylammonium chloride, 1,5-diazabicyclo[4.3.0]-5-nonene, N-(2-aminoethyl)piperazine, N,N-diethylnicotinamide, and pyridine N-oxide.

2. The method as set forth in claim 1, wherein the compound is at least one selected from the group consisting of 2-amino-6-methylpyridine, N-benzylethanolamine, 1,5-diazabicyclo[4.3.0]-5-nonene, N,N-diethylnicotinamide, 2,3-dimethyl-1-phenyl-5-pyrazolone, 3-picolylamine, and N-methylnicotinamide.

3. The method as set forth in claim 1, wherein the compound is at least one selected from the group consisting of benzylamine, 2,3-dimethyl-1-phenyl-5-pyrazolone, N-methylnicotinamide, 1,5-diazabicyclo[4.3.0]-5-nonene, and 3-picolylamine.

4. The method of claim 1, wherein the compound comprises at least one selected from the group consisting of a benzylamine, 3-picolylamine, 2-methylpyridine N-oxide, 4-methylpyridine N-oxide, pyridine N-oxide, N-benzylethanolamine, diphenhydramine hydrochloride, and 3-picolylamine.

5. The method as set forth in claim 1, wherein the compound comprises at least one selected from the group consisting of 4-methylpyridine N-oxide, 2-amino-6-methylpyridine, 2-methylpyridine N-oxide, 2,3-dimethyl-1-phenyl-5-pyrazolone, pyridine N-oxide, and N-(2-aminoethyl)piperazine.

6. The method as set forth in claim 1, wherein the compound comprises hydrazine carbonate.

7. The method as set forth in claim 1, wherein the compound comprises S-[2-(dimethylamino)ethyl]isothiourea dihydrochloride.

8. The method as set forth in claim 1, wherein the compound comprises at least one selected from the group consisting of xylazine hydrochloride, benzyldimethylphenylammonium chloride, DL-phenylephrine hydrochloride, tolperisone hydrochloride, bis(2-dimethylaminoethyl)disulfide dihydrochloride, and benzyltributylammonium chloride.

9. The method as set forth in claim 1, wherein the compound comprises at least one selected from the group consisting of N,N-diethylnicotinamide, N-methylnicotinamide, N,N-dimethylbenzamide, and neostigmine bromide.

10. The method as set forth in claim 1, wherein the compound comprises 1,5-diazabicyclo[4.3.0]-5-nonene.

11. A method comprising
preparing a light-transmitting biological material by permeating an aqueous solution into a biological material, wherein the aqueous solution comprises at least one compound that is soluble at a concentration of 60 wt % or more in water, which the compound is in the aqueous solution at a concentration that is at least one value within a range of 60 wt % to 80 wt %, and the aqueous solution has a refractive index of 1.47 to 1.50,
wherein the compound comprises at least one compound selected from the group consisting of:
2-amino-6-methylpyridine,
N-benzylethanolamine,
1,5-diazabicyclo[4.3.0]-5-nonene,
N,N-diethylnicotinamide,
2,3-dimethyl-1-phenyl-5-pyrazolone,
3-picolylamine,
N-methylnicotinamide, and
benzylamine.

* * * * *